US012708470B2

(12) United States Patent
Yang et al.

(10) Patent No.: US 12,708,470 B2
(45) Date of Patent: Aug. 18, 2026

(54) SYSTEMS AND METHODS OF CONTACT SENSING AND CONTACT REACTION OF ROBOTIC ARMS

(71) Applicant: Auris Health, Inc., Redwood City, CA (US)

(72) Inventors: Bo Yang, Mountain View, CA (US); Munzir Zafar, Santa Clara, CA (US); Pouya Sabetian, Foster City, CA (US); Yanan Huang, Sunnyvale, CA (US); Ying Mao, San Mateo, CA (US)

(73) Assignee: Auris Health, Inc., Santa Clara, CA (US)

( * ) Notice: Subject to any disclaimer, the term of this patent is extended or adjusted under 35 U.S.C. 154(b) by 447 days.

(21) Appl. No.: 18/342,211

(22) Filed: Jun. 27, 2023

(65) Prior Publication Data

US 2023/0346497 A1 Nov. 2, 2023

Related U.S. Application Data

(63) Continuation of application No. PCT/IB2021/061417, filed on Dec. 7, 2021.

(Continued)

(51) Int. Cl.

*A61B 34/00* (2016.01)
*A61B 34/35* (2016.01)
*A61B 90/00* (2016.01)

(52) U.S. Cl.

CPC .............. *A61B 34/77* (2016.02); *A61B 34/35* (2016.02); *A61B 90/06* (2016.02); *A61B 2090/066* (2016.02); *A61B 2090/067* (2016.02)

(58) Field of Classification Search

None
See application file for complete search history.

(56) References Cited

U.S. PATENT DOCUMENTS 9,014,856 B2 4/2015 Manzo et al.
9,415,510 B2 8/2016 Hourtash et al.

(Continued)

FOREIGN PATENT DOCUMENTS

CA 2759545 A1 * 6/2012 ............ A61B 5/287
KR 2020-007334 A 6/2020

(Continued)

OTHER PUBLICATIONS

European Search Report, Extended, and Written Opinion dated Nov. 13, 2024 for Application No. EP 21914796.4, 8 pgs.

(Continued)

*Primary Examiner* — Arslan Azhar
(74) *Attorney, Agent, or Firm* — FBT Gibbons LLP

(57) ABSTRACT

Robotic medical systems can be capable of contact sensing and contact reaction. A robotic medical system can include a robotic arm and one or more sensors. The robotic medical system can be configured to detect, via the one or more sensors, a contact force or torque that is exerted on the robotic arm by an external object. In response to detecting the contact force or torque, and in accordance with a determination that a magnitude of the contact force or torque is between a lower contact force or torque limit and an upper contact force or torque limit, the robotic medical system can enable a first set of controlled movements on the robotic arm in accordance with the detected contact force or torque.

23 Claims, 43 Drawing Sheets

Related U.S. Application Data

(60) Provisional application No. 63/132,463, filed on Dec. 30, 2020.

(56) References Cited

U.S. PATENT DOCUMENTS

| | | | | |
|---|---|---|---|---|
| 10,456,915 | B1 * | 10/2019 | Diankov | G06T 7/73 |
| 11,039,891 | B2 | 6/2021 | Shochat et al. | |
| 2014/0276953 | A1 | 9/2014 | Swarup et al. | |
| 2017/0079727 | A1 | 3/2017 | Crawford et al. | |
| 2017/0296277 | A1 | 10/2017 | Hourtash et al. | |
| 2018/0193102 | A1 * | 7/2018 | Inoue | A61B 1/0016 |
| 2018/0338806 | A1 * | 11/2018 | Grubbs | A61B 34/30 |
| 2020/0030992 | A1 | 1/2020 | Motoyoshi et al. | |
| 2020/0217733 | A1 | 7/2020 | Lin et al. | |
| 2022/0233271 | A1 * | 7/2022 | Peine | A61B 90/06 |

FOREIGN PATENT DOCUMENTS

| | | | |
|---|---|---|---|
| WO | 2014/152418 | A1 | 9/2014 |
| WO | 2019/136039 | A1 | 7/2019 |
| WO | 2020/147078 | A1 | 7/2020 |

OTHER PUBLICATIONS

Japanese First Office Action dated May 27, 2025, for Application No. 2023-540046, 4 pages.

PCT International Search Report; PCT/IB2021/061417; Mar. 8, 2022; 4 pages.

PCT Written Opinion of the International Searching Authority; PCT/IB2021/061417; Mar. 8, 2022; 5 pages.

* cited by examiner 38
36
39
45
60
37
43
46

88
86
87
82
89

85
84
81
83
80

304-4
304-4
304-4
412-3
302-2
412-1
304-3
304-2
304-2
302-1
304-1
412-2

(i) (ii) (iii)

(i) Side view (ii) Front view

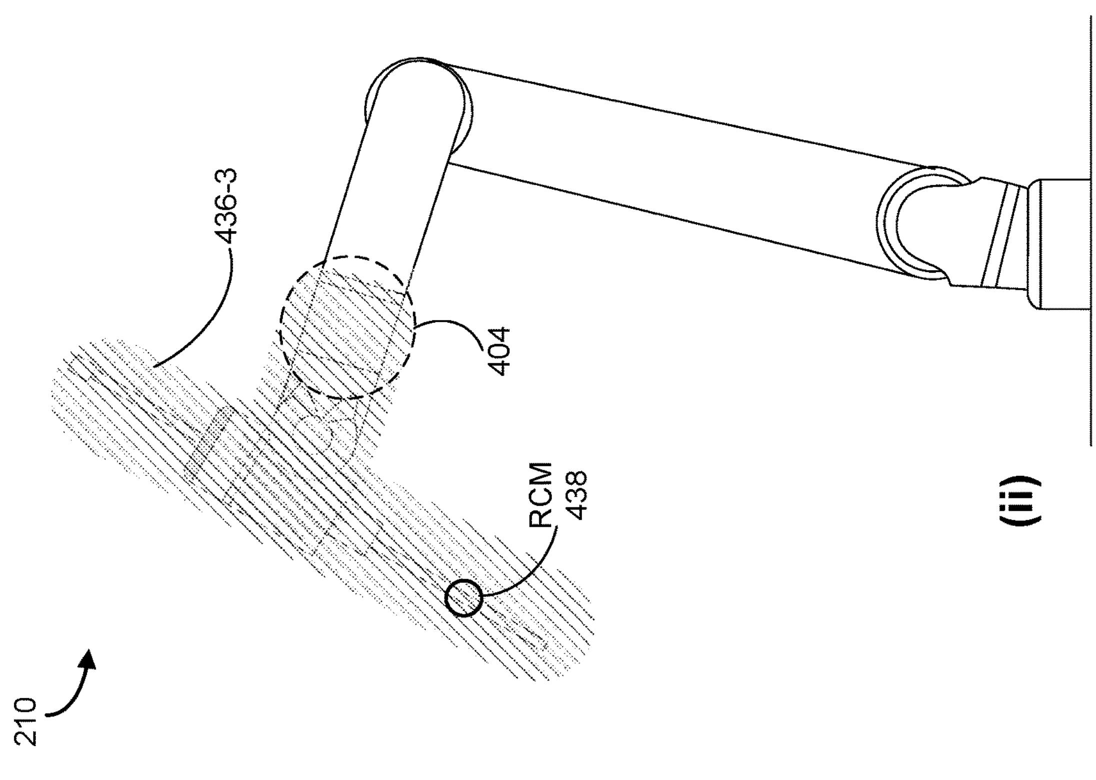
FIG. 24H
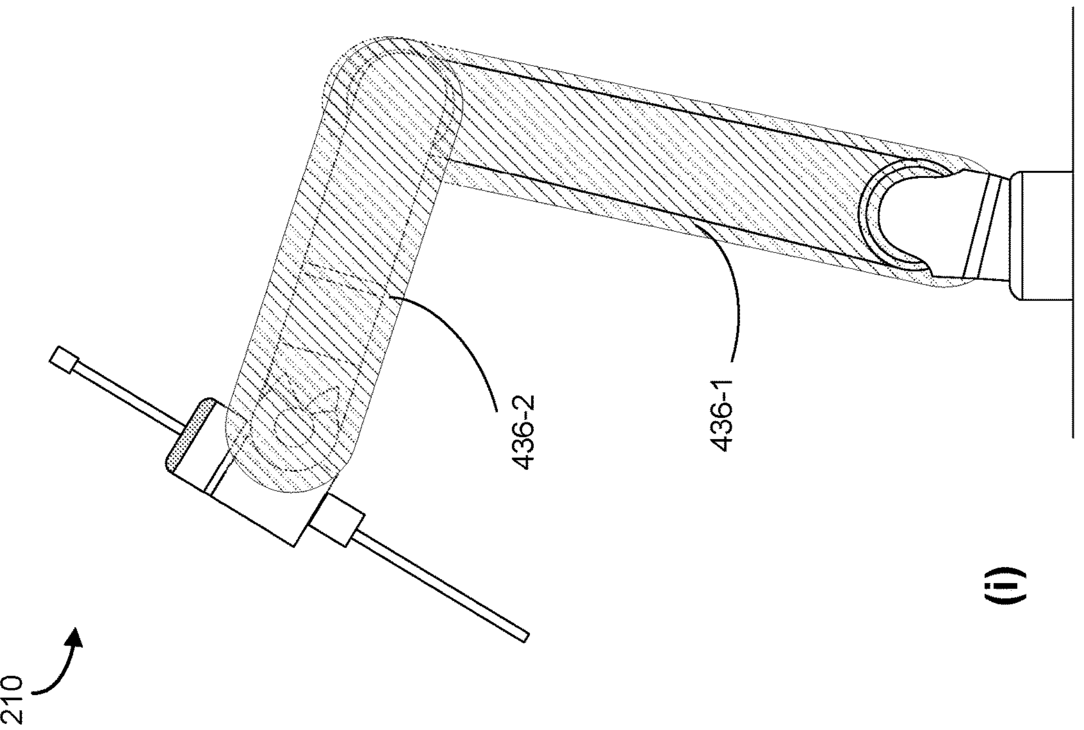

Figure 25B:
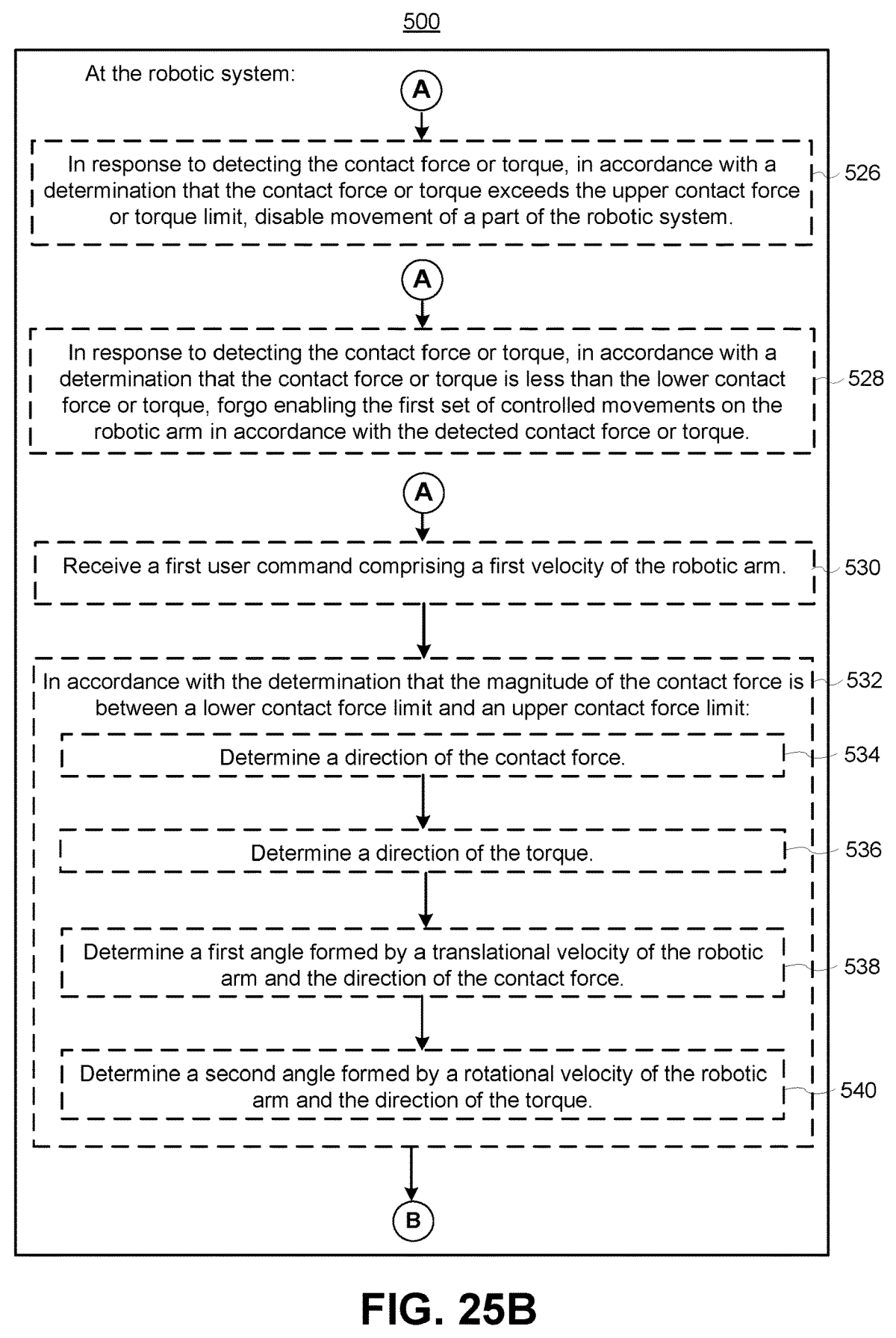

500

At the robotic system:

A

In response to detecting the contact force or torque, in accordance with a determination that the contact force or torque exceeds the upper contact force or torque limit, disable movement of a part of the robotic system. 526

A

In response to detecting the contact force or torque, in accordance with a determination that the contact force or torque is less than the lower contact force or torque, forgo enabling the first set of controlled movements on the robotic arm in accordance with the detected contact force or torque. 528

A

Receive a first user command comprising a first velocity of the robotic arm. 530

In accordance with the determination that the magnitude of the contact force is between a lower contact force limit and an upper contact force limit: 532

Determine a direction of the contact force. 534

Determine a direction of the torque. 536

Determine a first angle formed by a translational velocity of the robotic arm and the direction of the contact force. 538

Determine a second angle formed by a rotational velocity of the robotic arm and the direction of the torque. 540

Figure 27B:
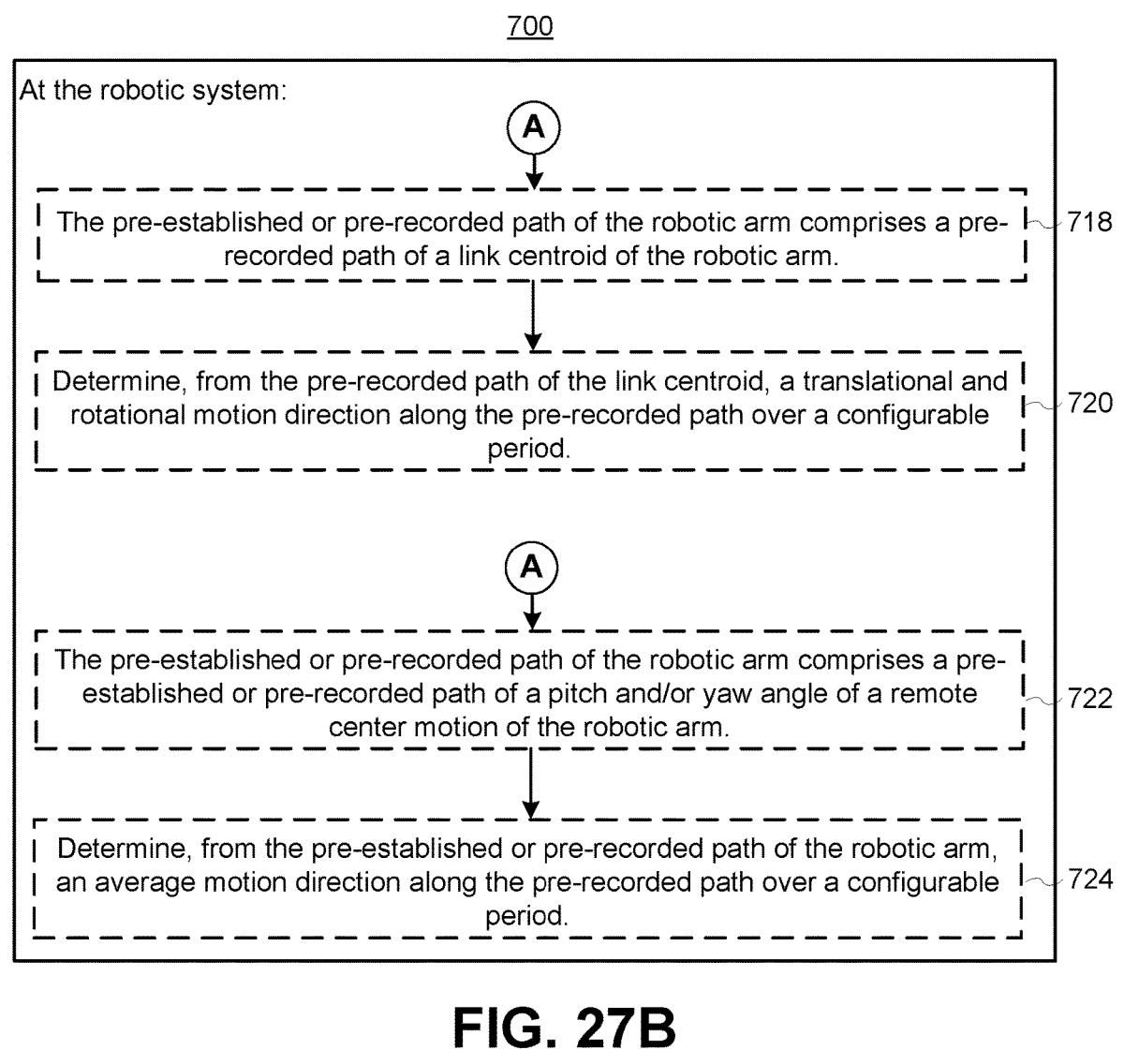

At the robotic system:

A

The pre-established or pre-recorded path of the robotic arm comprises a pre-recorded path of a link centroid of the robotic arm. 718

Determine, from the pre-recorded path of the link centroid, a translational and rotational motion direction along the pre-recorded path over a configurable period. 720

A

The pre-established or pre-recorded path of the robotic arm comprises a pre-established or pre-recorded path of a pitch and/or yaw angle of a remote center motion of the robotic arm. 722

Determine, from the pre-established or pre-recorded path of the robotic arm, an average motion direction along the pre-recorded path over a configurable period. 724

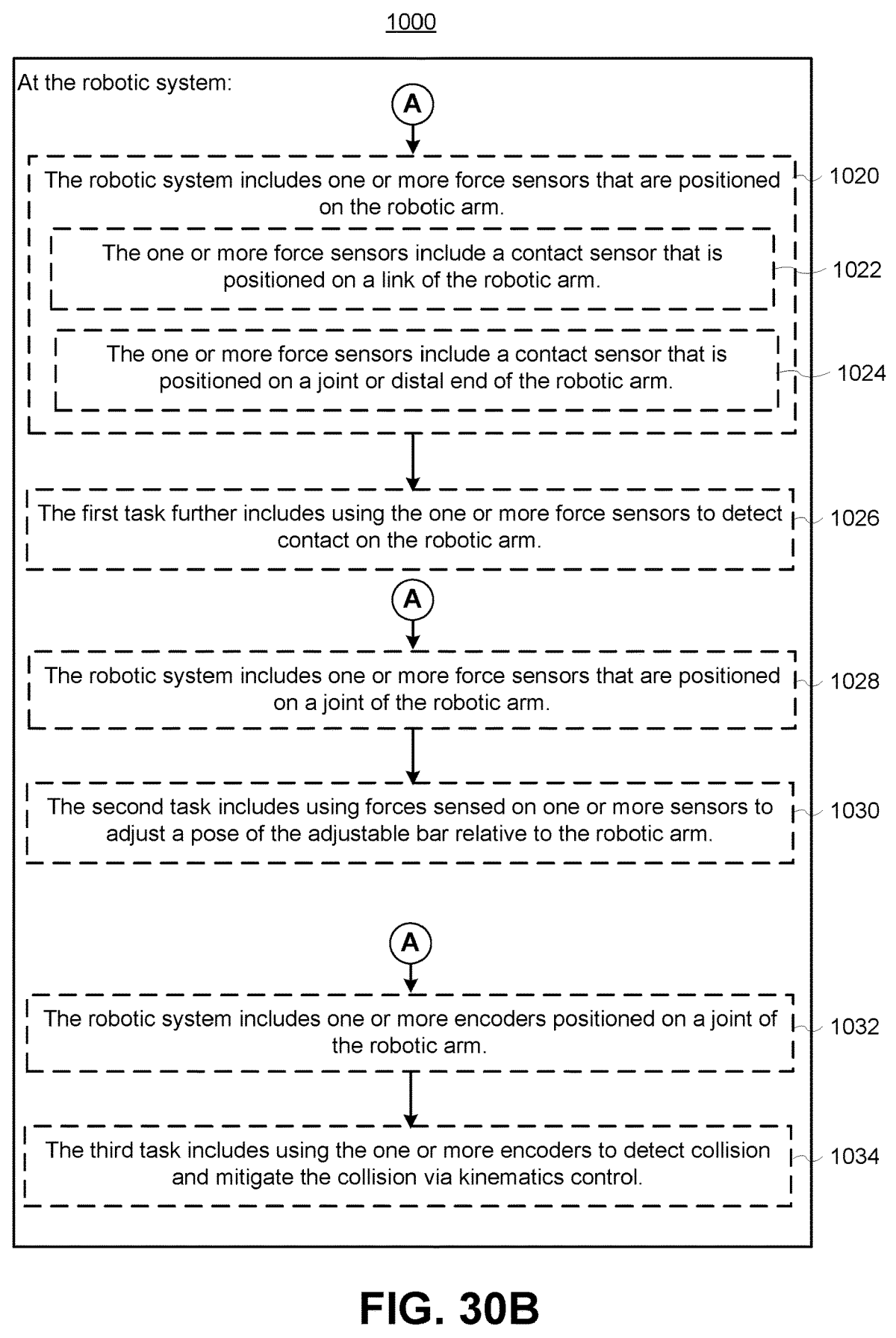

At the robotic system:

A

The robotic system includes one or more force sensors that are positioned on the robotic arm. 1020

The one or more force sensors include a contact sensor that is positioned on a link of the robotic arm. 1022

The one or more force sensors include a contact sensor that is positioned on a joint or distal end of the robotic arm. 1024

The first task further includes using the one or more force sensors to detect contact on the robotic arm. 1026

A

The robotic system includes one or more force sensors that are positioned on a joint of the robotic arm. 1028

The second task includes using forces sensed on one or more sensors to adjust a pose of the adjustable bar relative to the robotic arm. 1030

A

The robotic system includes one or more encoders positioned on a joint of the robotic arm. 1032

The third task includes using the one or more encoders to detect collision and mitigate the collision via kinematics control. 1034

FIG. 30B

SYSTEMS AND METHODS OF CONTACT SENSING AND CONTACT REACTION OF ROBOTIC ARMS

CROSS-REFERENCE TO RELATED APPLICATIONS

This present application is a continuation of International Patent Application PCT/IB2021/061417, filed Dec. 7, 2021 and entitled "SYSTEMS AND METHODS OF CONTACT SENSING AND CONTACT REACTION OF ROBOTIC ARMS," which claims priority to U.S. Provisional Application No. 63/132,463, filed Dec. 30, 2020 and entitled, "SYSTEMS AND METHODS OF CONTACT SENSING AND CONTACT REACTION OF ROBOTIC ARMS," both of which are incorporated herein by reference in their entirety for all purposes.

TECHNICAL FIELD

The systems and methods disclosed herein are directed to robotic medical systems, and more particularly to robotically controlled arms of robotic medical systems.

BACKGROUND

A robotically-enabled medical system is capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

Such robotic medical systems may include robotic arms configured to control the movement of medical tool(s) during a given medical procedure. In order to achieve a desired pose of a medical tool, a robotic arm may be placed into a pose during a set-up process or during teleoperation. Some robotically-enabled medical systems may include an arm support (e.g., a bar) that is connected to respective bases of the robotic arms and supports the robotic arms.

SUMMARY

During robotic surgery, a robotic arm may, e.g., due to movement under teleoperation of the robotic arms, come into contact with adjacent objects such as a patient, medical personnel, or accessories in the operating room, resulting in excessive contact force and/or torque on the patient or the medical personnel. The excessive contact force or torque may cause injury and discomfort to the patient or the medical personnel during surgery. In some circumstances, in response to such contact force and/or torque, one or more joints and/or links of the robotic arm may execute null space motion to maintain a pose (e.g., of a position and/or orientation of a cannula). In some circumstances, the operator may be required to move the patient or to reach for an input control before moving the robotic arm out of the way. However, these actions may pose additional risks of undesirable collisions and contact with the patient or other object in the operating room.

Accordingly, an improved robotic medical system is desirable. In particular, there is a need for a robotic medical system that detects interactions (e.g., forces and/or torques) on a robotic arm (e.g., on linkages, joints, etc. of the robotic arm) and, depending on the characteristics (e.g., magnitude, direction, rate of change, etc.) of detected force and/or torque, take certain appropriate actions such as enabling null space motion of the robotic arm, moving one or more joints and/or links of the robotic arm with suitable speeds, and/or in directions that are selected in accordance with the characteristics (e.g., magnitude, direction, rate of change, etc.) of detected force and/or torque, or disabling teleoperation, etc. This advantageously improves patient and/or operator safety during surgery. It also ensures reduced interruption while the surgeon is driving one or more of the robotic arms during surgery.

In addition, as disclosed herein, sensors are distributed throughout multiple regions of the robotic arm(s) to detect forces and/or torques on the robotic arm(s) and enable controlled movements on the robotic arm in accordance with the detected contact force or torque. Accordingly, the operational burden placed on the medical personnel, to manually adjust the pose of the robotic arm, move the patient, and/or reposition oneself, etc., during teleoperation is reduced.

In another aspect of the present disclosure, a robotic arm may include at least one degree of freedom of redundancy, which can be used for several different objectives while delivering the instrument to the desired pose and holding the remote center of motion (RCM). These objectives may include kinematic collision avoidance, joint limit avoidance, excessive contact avoidance, admittance null space motion for manual arm repositioning and positioning a robot joint at a preferred location. In some circumstances, each of these objectives requests a respective null space motion of the robotic arm. Because the robotic arm has limited degree(s) of freedom available for null space motion, these objectives may conflict each other at times. Accordingly, there is a need to optimize these objectives simultaneously for the robotic arm under various states of the operation and control the null space motion in a balanced, optimal way.

As disclosed herein, a robotic medical system can manage null space motion requests associated with the various objectives by identifying a plurality of tasks for the robotic system that each may request a respective null space motion of the robotic arm. The robotic system can prioritize the tasks according to a unifying scheme (e.g., a selected one of a number of available schemes such as exclusivity, switching or weighting, etc.) and determine a null space velocity of the robotic arm according to the unifying scheme. In some embodiments, the medical robotic system can determine (e.g., generate a "cost function" with suitable weights and quantitative measures) of the "severity" or imperativeness for each null space motion request under the current circumstance and determines a suitable null space joint velocity of the robotic arm by reducing the aggregated "severity" (e.g., optimizing the cost function) of the null space motion requests under the current circumstance. The robotic medical system then executes null space motion of the robotic arm based on the null space joint velocity determined using the unifying scheme, which corresponds to a suitable balance between the competing priorities (e.g., safety, power consumption, efficiency, goals and constraints of different tasks, etc.) under the circumstance.

The systems, methods and devices of this disclosure each have several innovative aspects, no single one of which is solely responsible for the desirable attributes disclosed herein.

In accordance with some embodiments of the present disclosure, a robotic system includes a robotic arm. The robotic system also includes one or more sensors. The robotic system further includes one or more processors and memory. The memory stores instructions that, when executed by the one or more processors, cause the one or more processors to detect, via the one or more sensors, a contact force or torque that is exerted on the robotic arm by an external object. In response to detecting the contact force or torque, in accordance with a determination that a magnitude of the contact force or torque is between a lower contact force or torque limit and an upper contact force or torque limit, the one or more processors enable a first set of controlled movements on the robotic arm in accordance with the detected contact force or torque.

In some embodiments, enabling a first set of controlled movements on the robotic arm includes activating null space motion of the robotic arm.

In some embodiments, the memory further includes instructions that, when executed by the one or more processors, cause the one or more processors to: in response to detecting the contact force or torque, in accordance with a determination that the contact force or torque exceeds the upper contact force or torque limit, disable movement of a part of the robotic system.

In some embodiments, the memory further includes instructions that, when executed by the one or more processors, cause the one or more processors to: in response to detecting the contact force or torque, in accordance with a determination that the contact force or torque is less than the lower contact force or torque, forgo enabling the first set of controlled movements on the robotic arm in accordance with the detected contact force or torque.

In some embodiments, the one or more sensors include one or more contact sensors. The contact force or torque is detected using the one or more contact sensors.

In some embodiments, the one or more contact sensors are located on a link of the robotic arm.

In some embodiments, the link of the robotic arm is a distal link or a proximal link.

In some embodiments, the one or more sensors include a multi-axis load cell. The contact force or torque is detected using the multi-axis load cell.

In some embodiments, the multi-axis load cell includes a six-axis load cell that is located on a distal portion of the robotic arm.

In some embodiments, the memory further includes instructions that, when executed by the one or more processors, cause the one or more processors to receive a first user command comprising a first velocity of the robotic arm. In accordance with the determination that the magnitude of the contact force is between a lower contact force limit and an upper contact force limit, the one or more processors (a) determine a direction of the contact force, (b) determine a direction of the torque, (c) determine a first angle formed by a translational velocity of the robotic arm and the direction of the contact force and (d) determine a second angle formed by a rotational velocity of the robotic arm and the direction of the torque. In accordance with a determination that the first angle is within a first angular threshold and the second angle is within a second angular threshold, the one or more processors enable movement of one or more joints of the robotic arm at the first velocity. In accordance with at least one of: (i) a determination that the first angle exceeds the first angular threshold, or (ii) a determination that the second angle exceeds the second angular threshold, the one or more processors disable movement of the robotic arm.

In some embodiments, the first angular threshold and the second angular threshold are determined according to a measurement uncertainty of one or more contact sensors used to detect the contact force.

In some embodiments, the memory further includes instructions that, when executed by the one or more processors, cause the one or more processors to receive a second user command comprising a requested velocity (e.g., linear or angular) of the robotic arm. In accordance with the determination that the magnitude of the torque is between the lower torque limit and the upper torque limit, the one or more processors determine a direction of the torque. In some embodiments, the one or more processors can determine a third angle formed by the direction of the torque and the requested velocity (e.g., linear or angular) of the robotic arm. In accordance with a determination that the third angle is within a third angular threshold, the one or more processors enable movement the robotic arm at the requested velocity. In accordance with a determination that the third angle exceeds the third angular threshold, the one or more processors disable movement of the robotic arm.

In some embodiments, the magnitude of the torque is determined with respect to a remote center of motion of the robotic arm.

In some embodiments, the third angular threshold is determined according to a measurement uncertainty of a six-axis load cell used to detect the torque.

In accordance with some embodiments of the present disclosure, a robotic system includes a robotic arm. The robotic system also includes one or more sensors. The robotic system further includes one or more processors and memory. The memory stores instructions that, when executed by the one or more processors, cause the one or more processors to detect a contact force or torque exerted on the robotic arm by an external object via the one or more sensors. In response to detecting the contact force or torque, and in accordance with a determination that the contact force or torque is between a lower force or torque limit and an upper contact force or torque limit, the one or more processors enable movement of the robotic arm in a trajectory that is based on a pre-established or pre-recorded path of the robotic arm.

In some embodiments, the one or more sensors include one or more contact sensors.

In some embodiments, the one or more sensors include a six-axis load cell.

In some embodiments, the pre-established or pre-recorded path of the robotic arm includes a pre-recorded path of a link centroid of the robotic arm.

In some embodiments, the memory further includes instructions that, when executed by the one or more processors, cause the one or more processors to determine, from the pre-recorded path of the link centroid, a translational and rotational motion direction along the pre-recorded path over a configurable period.

In some embodiments, the pre-established or pre-recorded path of the robotic arm includes a pre-established or pre-recorded path of a pitch and/or yaw angle of a remote center motion of the robotic arm.

In some embodiments, the memory further includes instructions that, when executed by the one or more processors, cause the one or more processors to determine, from the pre-established or pre-recorded path of the robotic arm, an average motion direction along the pre-recorded path over a configurable period.

In accordance with some embodiments of the present disclosure, a robotic system includes a robotic arm. The robotic system includes one or more sensors. The robotic system also includes one or more processors and memory. The memory stores instructions that, when executed by the one or more processors, cause the one or more processors to detect a contact force or torque on the robotic arm exerted by an external object via the one or more sensors. In accordance with a determination that the contact force or torque is greater than or equal to a lower reaction force or torque limit, the one or more processors reduce a velocity of the robotic arm.

In some embodiments, the robotic arm includes one or more joints. Reducing the velocity of the robotic arm includes reducing a respective velocity for each of the one or more joints of the robotic arm.

In some embodiments, reducing the respective velocity for each of the one or more joints includes reducing velocities of all the joints by a same scale.

In some embodiments, reducing the velocity of the robotic arm includes reducing an angular velocity at a remote center motion of the robotic arm.

In some embodiments, the one or more sensors include one or more contact sensors.

In some embodiments, the one or more sensors include a six-axis load cell.

In accordance with another aspect of the present disclosure, a robotic system includes a user console. The robotic system also includes a robotic arm. The robotic system also includes an adjustable bar coupled to the robotic arm. The robotic system further includes one or more processors and memory. The memory stores instructions that, when executed by the one or more processors, cause the one or more processors to control null space motion of the robotic arm and/or the adjustable bar based on inputs from two or more tasks of a plurality of tasks for execution by the robotic system. The plurality of tasks include: a first task comprising contact detection and reaction of the robotic arm, a second task comprising optimization of the adjustable bar, a third task comprising collision and/or joint limit handling via kinematics, a fourth task comprising robotic arm null space and/or bar pose jogging, and a fifth task comprising motion toward preferred joint position.

In some embodiments, the robotic system further includes one or more force sensors that are positioned on the robotic arm. The first task further includes using the one or more force sensors to detect contact on the robotic arm.

In some embodiments, the one or more force sensors include a contact sensor that is positioned on a link of the robotic arm.

In some embodiments, the one or more force sensors include a contact sensor that is positioned on a joint or distal end of the robotic arm.

In some embodiments, the robotic system further includes one or more force sensors that are positioned on a joint of the robotic arm. The second task includes using forces sensed on one or more sensors to adjust a pose of the adjustable bar relative to the robotic arm.

In some embodiments, the robotic system further includes one or more encoders positioned on a joint of the robotic arm. The third task includes using the one or more encoders to detect collision and mitigate the collision via kinematics control.

In some embodiments, the memory further includes instructions that, when executed by the one or more processors, cause the one or more processors to prioritize one or more tasks of the plurality of tasks based on preset mutual exclusivity between tasks in the plurality of tasks.

In some embodiments, the memory further includes instructions that, when executed by the one or more processors, cause the one or more processors to assign a respective weight to each of the plurality of tasks. The memory also includes instructions that, when executed by the one or more processors, cause the one or more processors to prioritize one or more tasks of the plurality of tasks based on relative magnitudes of the respective weights of the plurality of tasks.

In some embodiments, the memory further includes instructions that, when executed by the one or more processors, cause the one or more processors to switch between distinct sets of one or more tasks in the plurality of tasks based on a current state of the robotic system.

In some embodiments, the robotic arm has at least one degree of freedom of redundancy.

In some embodiments, controlling the null space motion of the robotic arm includes moving one or more joints of the robotic arm to a desired pose at an optimum null space joint velocity.

In some embodiments, the memory further includes instructions that, when executed by the one or more processors, cause the one or more processors to execute the null space motion of the robotic arm while allowing an end effector of the robotic arm to follow a command.

In accordance with another aspect of the present disclosure, a method is performed at a robotic system. The robotic system includes a robotic arm, an adjustable bar coupled to the robotic arm, one or more processors, and memory. The memory stores one or more programs configured for execution by the one or more processors. The method includes identifying a first plurality of tasks for the robotic system. Each task of the first plurality of tasks requests a respective null space motion of the robotic arm having a corresponding null space joint velocity. The first plurality of tasks include two or more of: a first task comprising kinematic collision avoidance; a second task comprising joint limit avoidance; a third task comprising contact avoidance and admittance null space motion; and a fourth task comprising motion toward a preferred joint position. The method includes executing null space motion of the robotic arm based on a first null space joint velocity of the robotic arm that is determined by reducing a cost function that includes a first cost corresponding to optimization of the adjustable bar and/or robotic arm null space and/or bar pose jogging and a plurality of second costs corresponding to each task of the first plurality of tasks.

In some embodiments, the method includes reducing the cost function using a gradient descent algorithm with a successive step-size reduction.

In some embodiments, the method includes moving one or more joints of the robotic arm to a desired pose at the first null space joint velocity.

In some embodiments, the execution of the null space motion of the robotic arm occurs while allowing an end effector of the robotic arm to follow a command.

In some embodiments, the method further includes assigning a first weight for the first cost, and assigning a respective second weight for each of the plurality of second costs.

In some embodiments, at least one of the second costs has a respective second weight of zero.

In some embodiments, assignment of the respective second weight to each of the plurality of second costs is performed in accordance with a state of operation of the robotic system.

In some embodiments, a robotic system includes a robotic arm, an adjustable bar coupled to the robotic arm, one or more processors, and memory. The memory stores one or more programs that, when executed by the one or more processors, cause the one or more processors to perform any of the methods described herein.

Note that the various embodiments described above can be combined with any other embodiments described herein. The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIGS. 24A to 24H illustrate sensors of a robotic arm 210 according to some embodiments.

FIGS. 25A to 25C illustrate a flowchart diagram of a method for detecting and responding to contact forces and/or torques according to some embodiments.

FIGS. 27A and 27B illustrate flowchart diagram of another method for detecting and responding to contact forces and/or torques according to some embodiments.

FIGS. 30A to 30C illustrate a flowchart diagram of a method of controlling null space motion of a robotic arm according to some embodiments.

DETAILED DESCRIPTION

1. Overview

Aspects of the present disclosure may be integrated into a robotically-enabled medical system capable of performing a variety of medical procedures, including both minimally invasive, such as laparoscopy, and non-invasive, such as endoscopy, procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other embodiments of the disclosed concepts are possible, and various advantages can be achieved with the disclosed embodiments. Headings are included herein for reference and to aid in locating various sections. These headings are not intended to limit the scope of the concepts described with respect thereto. Such concepts may have applicability throughout the entire specification.

A. Robotic System—Cart.

Figure 1:
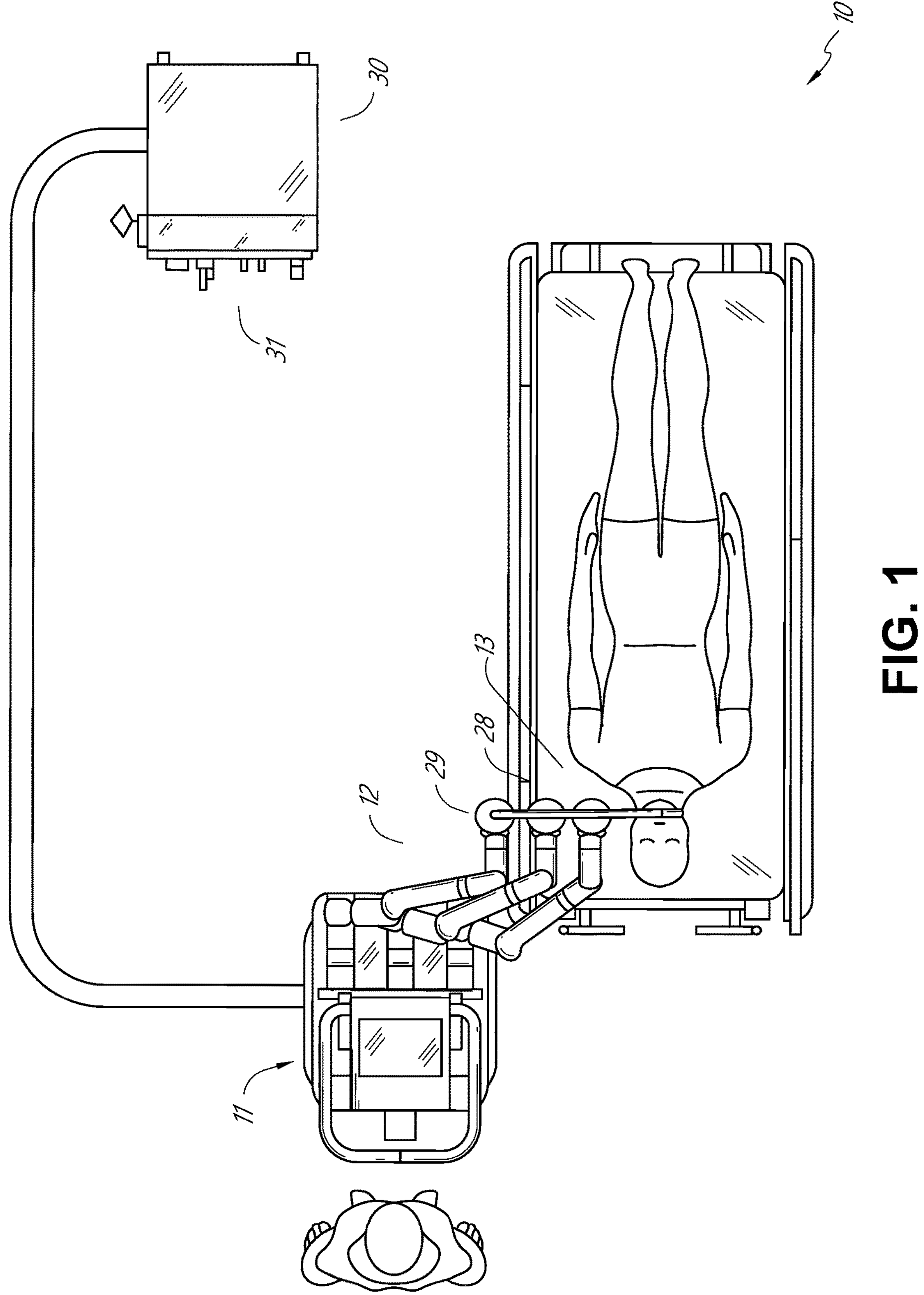
FIG. 1 illustrates an embodiment of a cart-based robotic system arranged for diagnostic and/or therapeutic bronchoscopy procedure(s).
Figure 2:
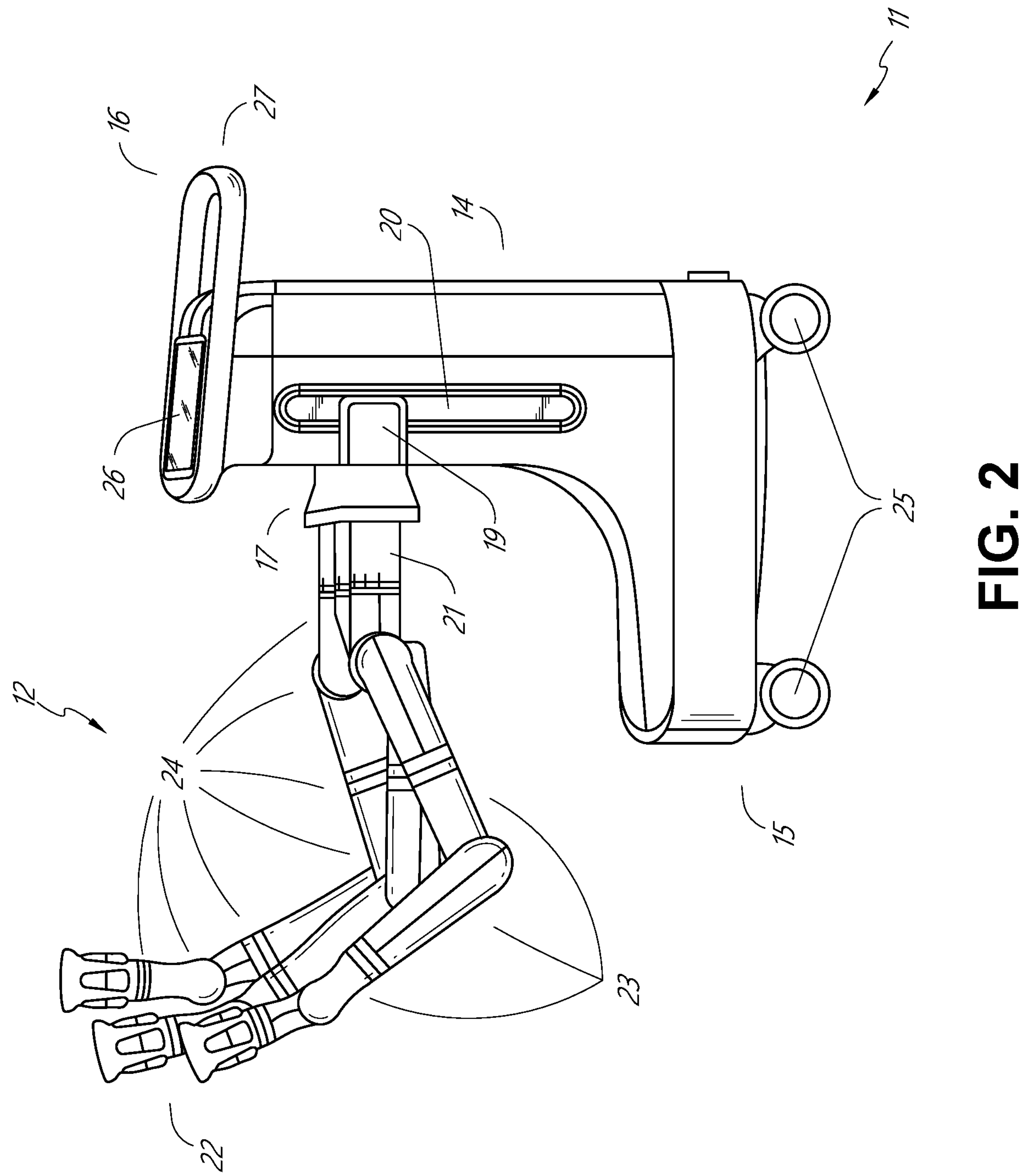
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy procedure. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independent of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include opto-electronics equipment for detecting, receiving, and processing data received from the optical sensors or cameras throughout the robotic system 10. In combination with the control system, such opto-electronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in system 10 are generally designed to provide both robotic controls as well as pre-operative and real-time information of the procedure, such as navigational and localization information of the endoscope 13. When the console 31 is not the only console available to the physician, it may be used by a second operator, such as a nurse, to monitor the health or vitals of the patient and the operation of system, as well as provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart, the support for controls, optics, fluidics, and/or navigation may be provided through a separate cable.

FIG. 2 provides a detailed illustration of an embodiment of the cart from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm. Each of the arms 12 have seven joints, and thus provide seven degrees of freedom. A multitude of joints result in a multitude of degrees of freedom, allowing for "redundant" degrees of freedom. Redundant degrees of freedom allow the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and arms 12 over the floor. Accordingly, the cart base 15 houses heavier components, such as electronics, motors, power supply, as well as components that either enable movement and/or immobilize the cart. For example, the cart base 15 includes rollable wheel-shaped casters 25 that allow for the cart to easily move around the room prior to a procedure. After reaching the appropriate position, the casters 25 may be immobilized using wheel locks to hold the cart 11 in place during the procedure.

Positioned at the vertical end of column 14, the console 16 allows for both a user interface for receiving user input and a display screen (or a dual-purpose device such as, for example, a touchscreen 26) to provide the physician user with both pre-operative and intra-operative data. Potential pre-operative data on the touchscreen 26 may include pre-operative plans, navigation and mapping data derived from pre-operative computerized tomography (CT) scans, and/or notes from pre-operative patient interviews. Intra-operative data on display may include optical information provided from the tool, sensor and coordinate information from sensors, as well as vital patient statistics, such as respiration, heart rate, and/or pulse. The console 16 may be positioned and tilted to allow a physician to access the console from the side of the column 14 opposite carriage 17. From this position, the physician may view the console 16, robotic arms 12, and patient while operating the console 16 from behind the cart 11. As shown, the console 16 also includes a handle 27 to assist with maneuvering and stabilizing cart 11.

Figure 3:
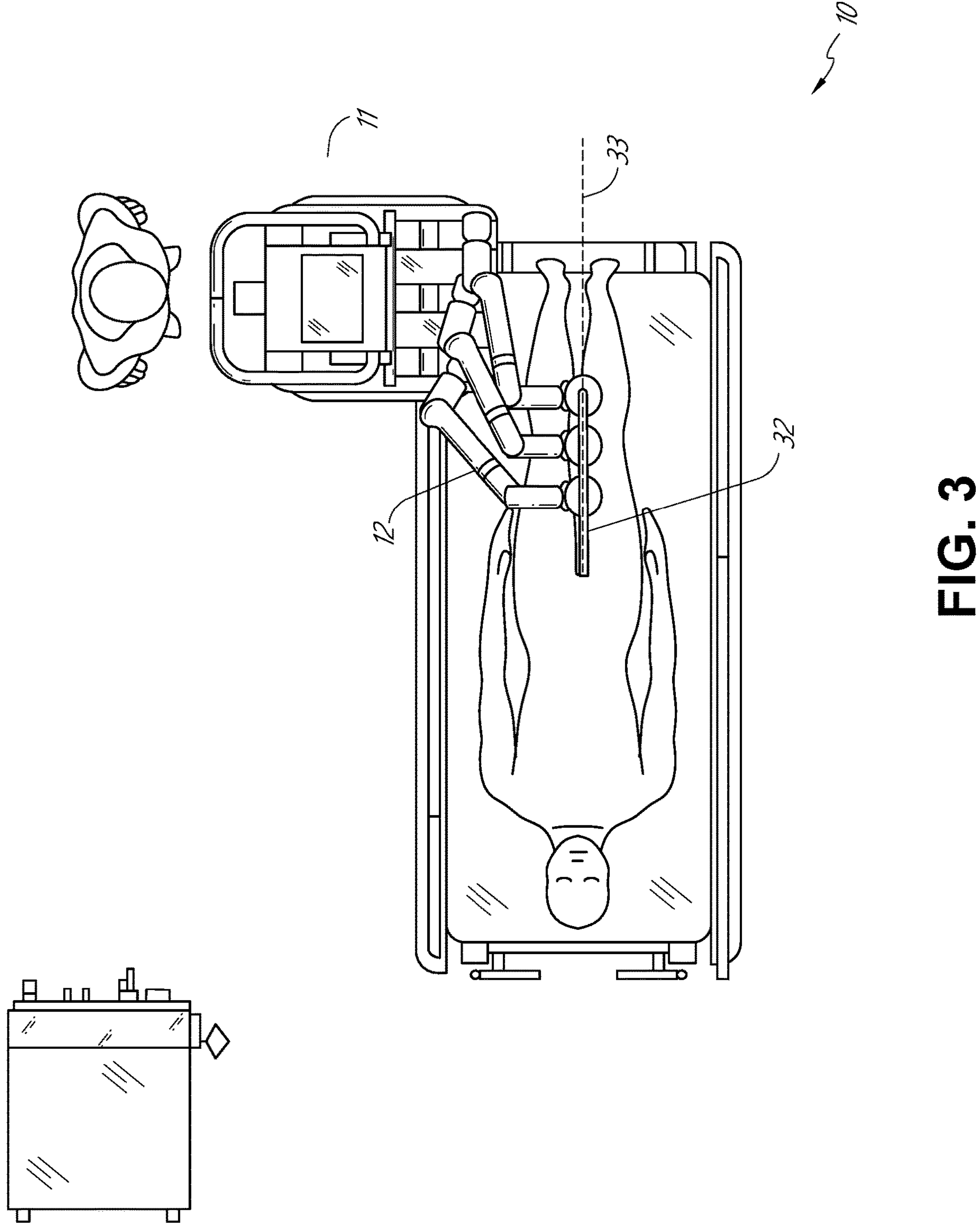
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
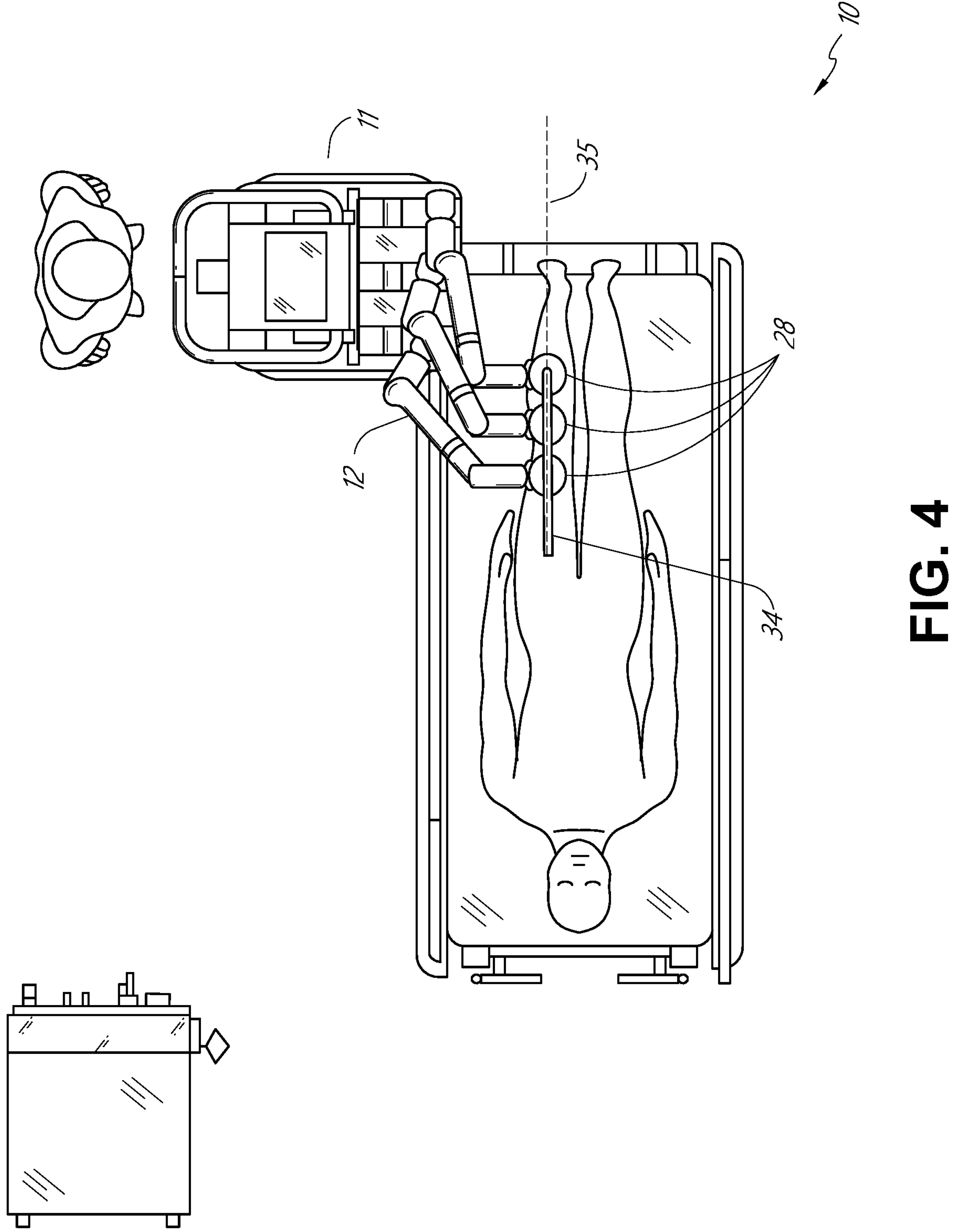
FIG. 4 illustrates an embodiment of the robotic system of FIG. 1 arranged for a vascular procedure.

FIG. 4 illustrates an embodiment of a robotically-enabled system similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
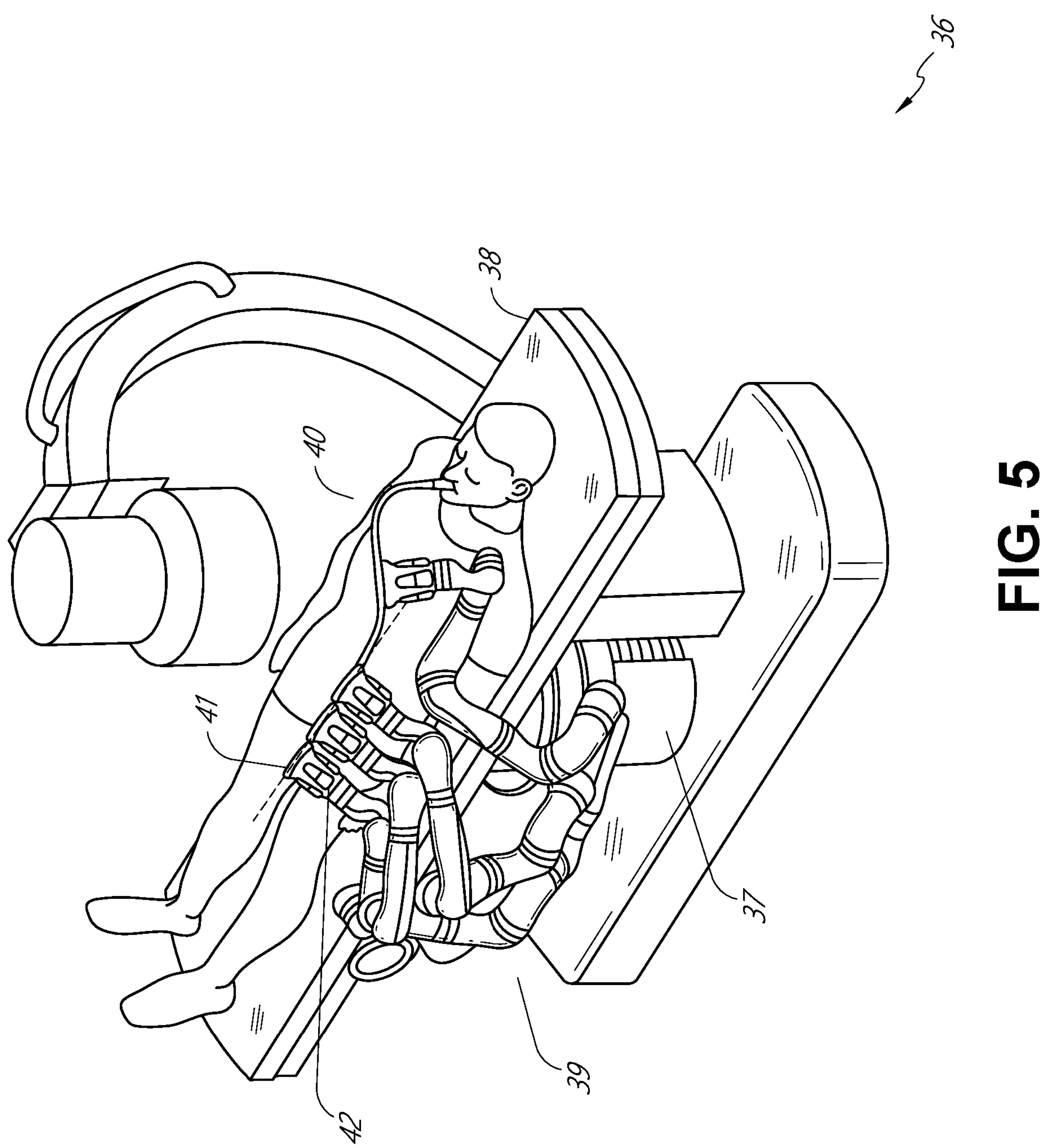
FIG. 5 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopy procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around table 38.

Figure 6:
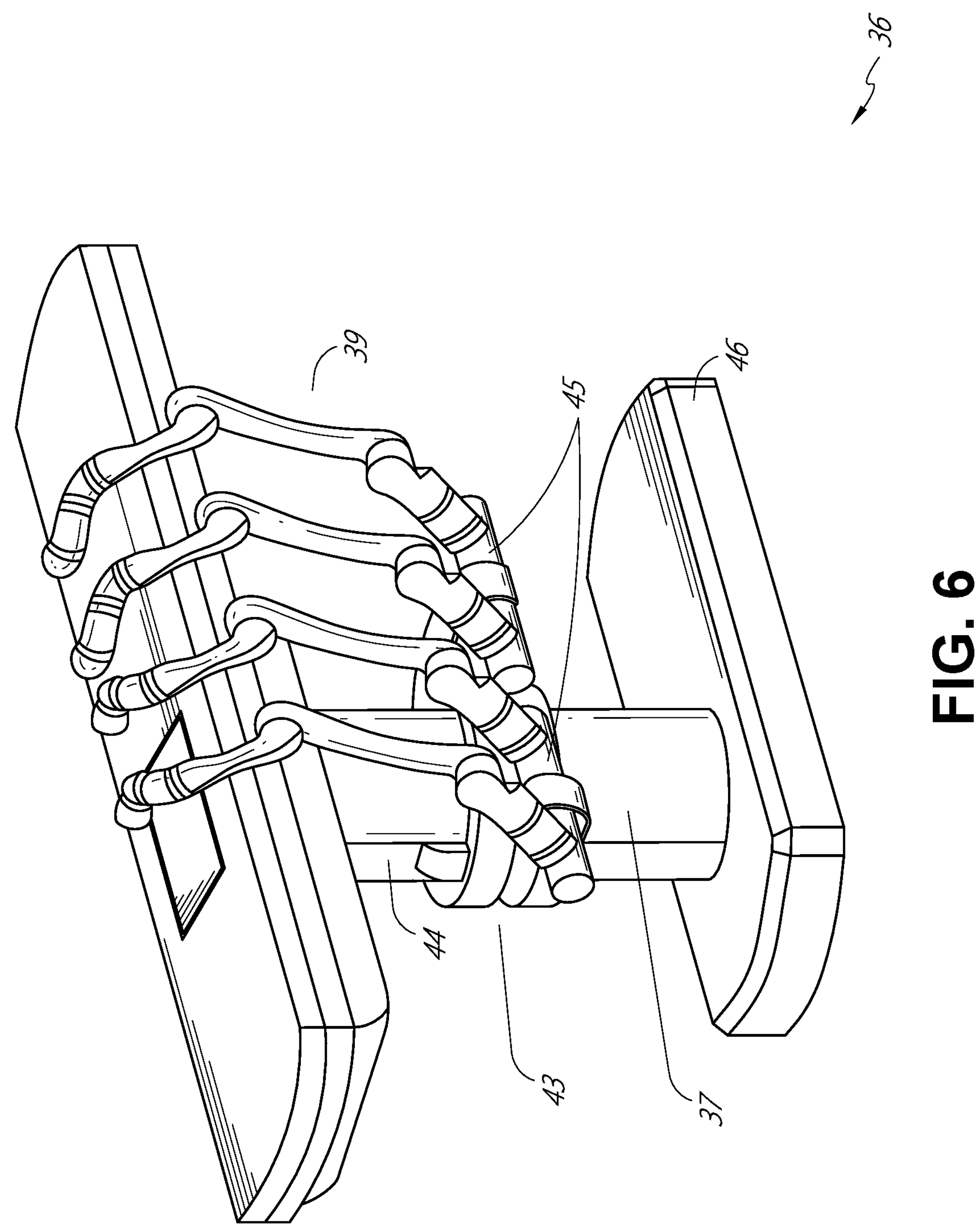
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independent of the other carriages. While carriages 43 need not surround the column 37 or even be circular, the ring-shape as shown facilitates rotation of the carriages 43 around the column 37 while maintaining structural balance. Rotation and translation of the carriages 43 allows the system to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
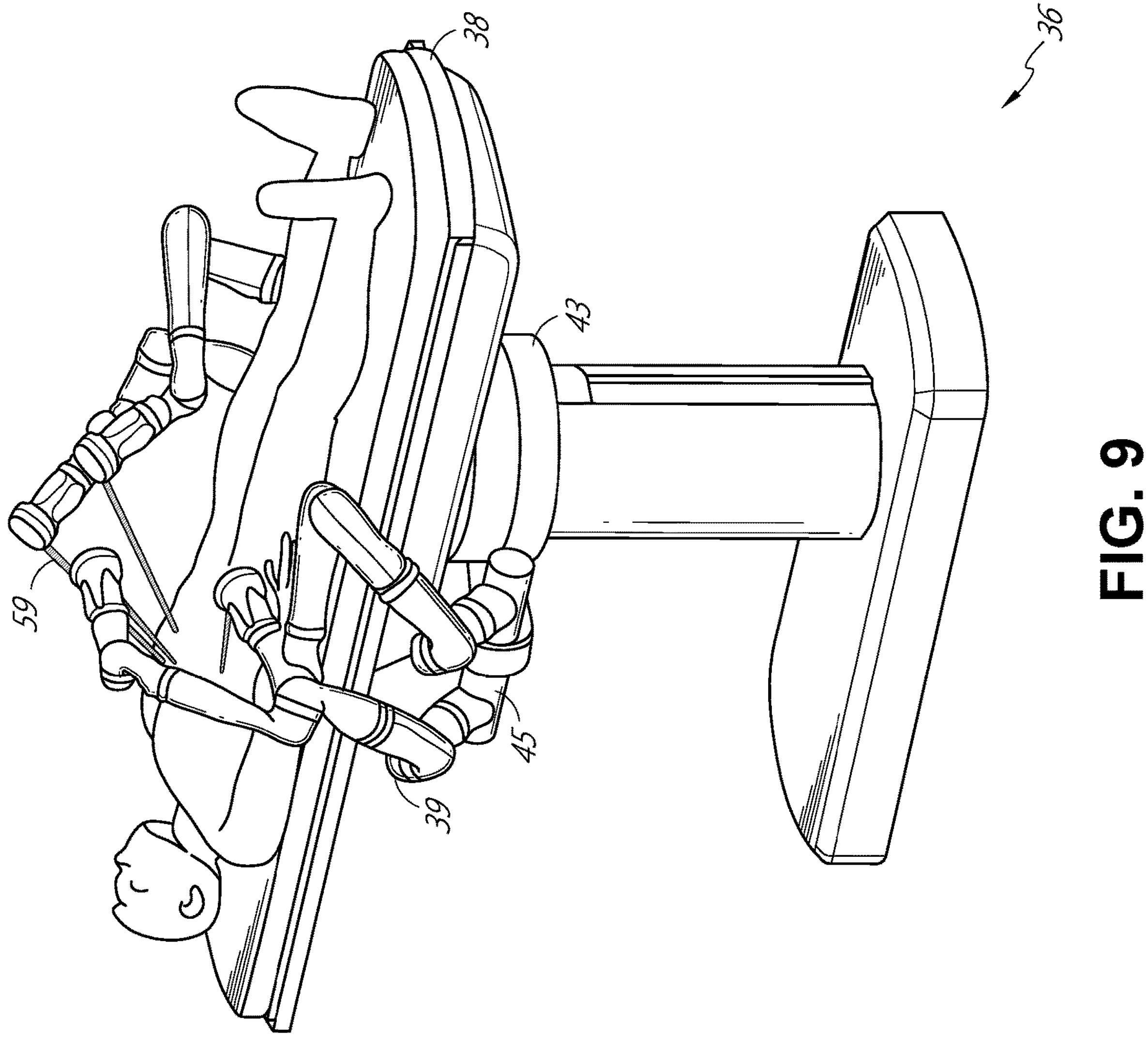
FIG. 9 illustrates an embodiment of a table-based robotic system configured for a laparoscopic procedure.

The arms 39 may be mounted on the carriages through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of table 38 (as shown in FIG. 6), on opposite sides of table 38 (as shown in FIG. 9), or on adjacent sides of the table 38 (not shown).

The column 37 structurally provides support for the table 38, and a path for vertical translation of the carriages. Internally, the column 37 may be equipped with lead screws for guiding vertical translation of the carriages, and motors to mechanize the translation of said carriages based the lead screws. The column 37 may also convey power and control signals to the carriage 43 and robotic arms 39 mounted thereon.

The table base 46 serves a similar function as the cart base 15 in cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

Continuing with FIG. 6, the system 36 may also include a tower (not shown) that divides the functionality of system 36 between table and tower to reduce the form factor and bulk of the table. As in earlier disclosed embodiments, the tower may provide a variety of support functionalities to table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base for potential stowage of the robotic arms. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 7:
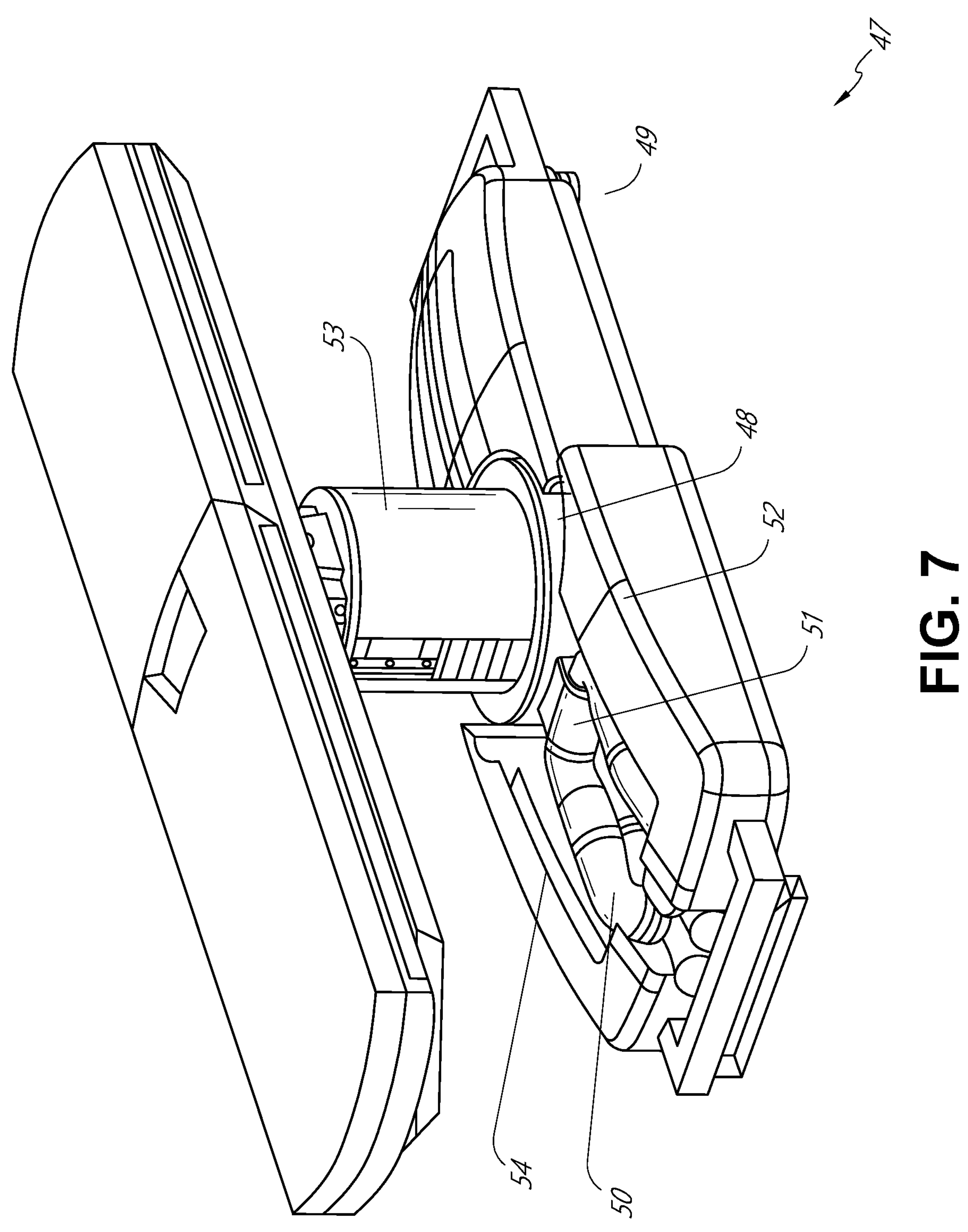
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and arms 50 around column 53, and closed to stow to protect them when not in use. The base covers 52 may be sealed with a membrane 54 along the edges of its opening to prevent dirt and fluid ingress when closed.

Figure 8:
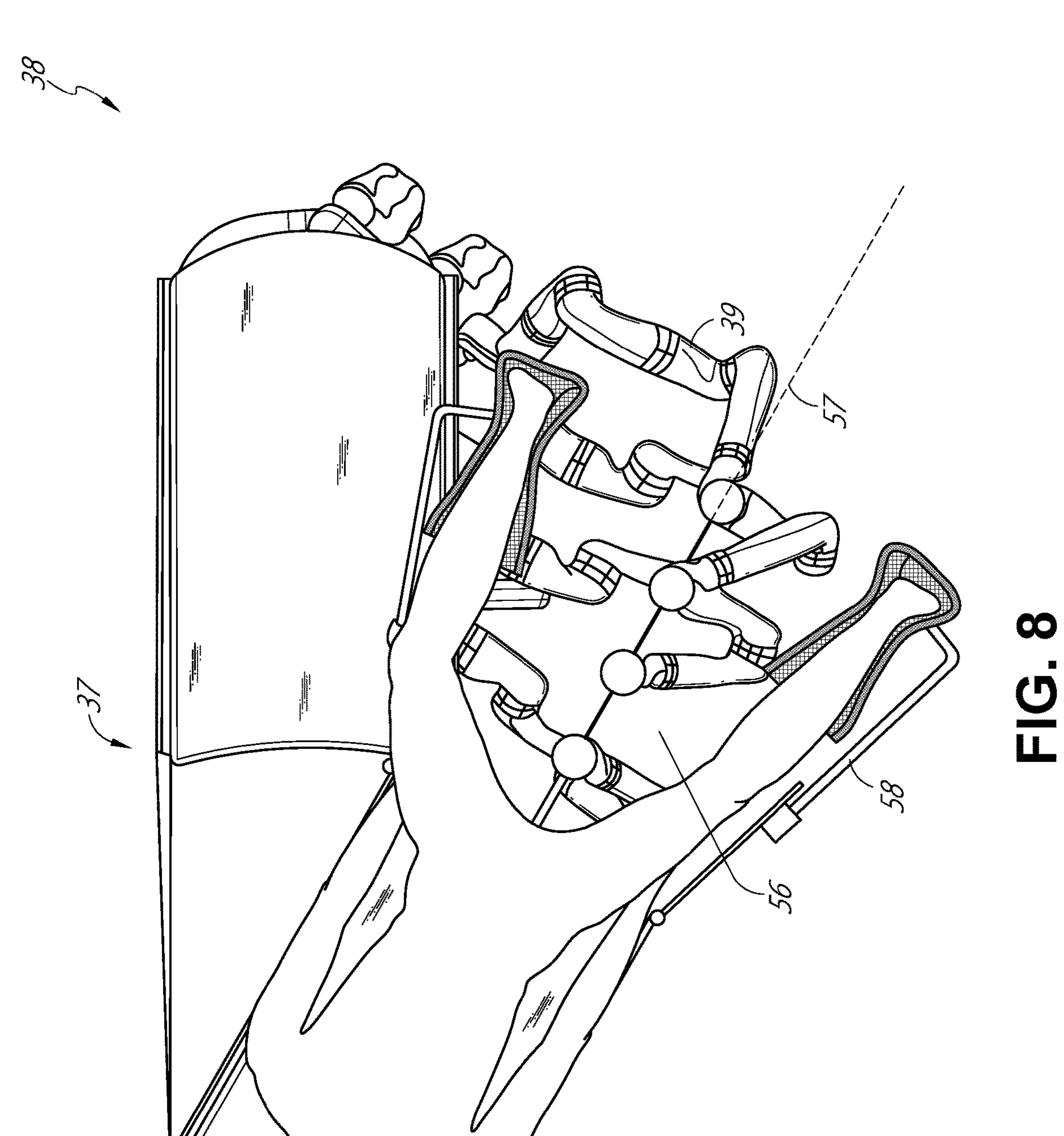
FIG. 8 illustrates an embodiment of a table-based robotic system configured for a ureteroscopy procedure.

FIG. 8 illustrates an embodiment of a robotically-enabled table-based system configured for a ureteroscopy procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
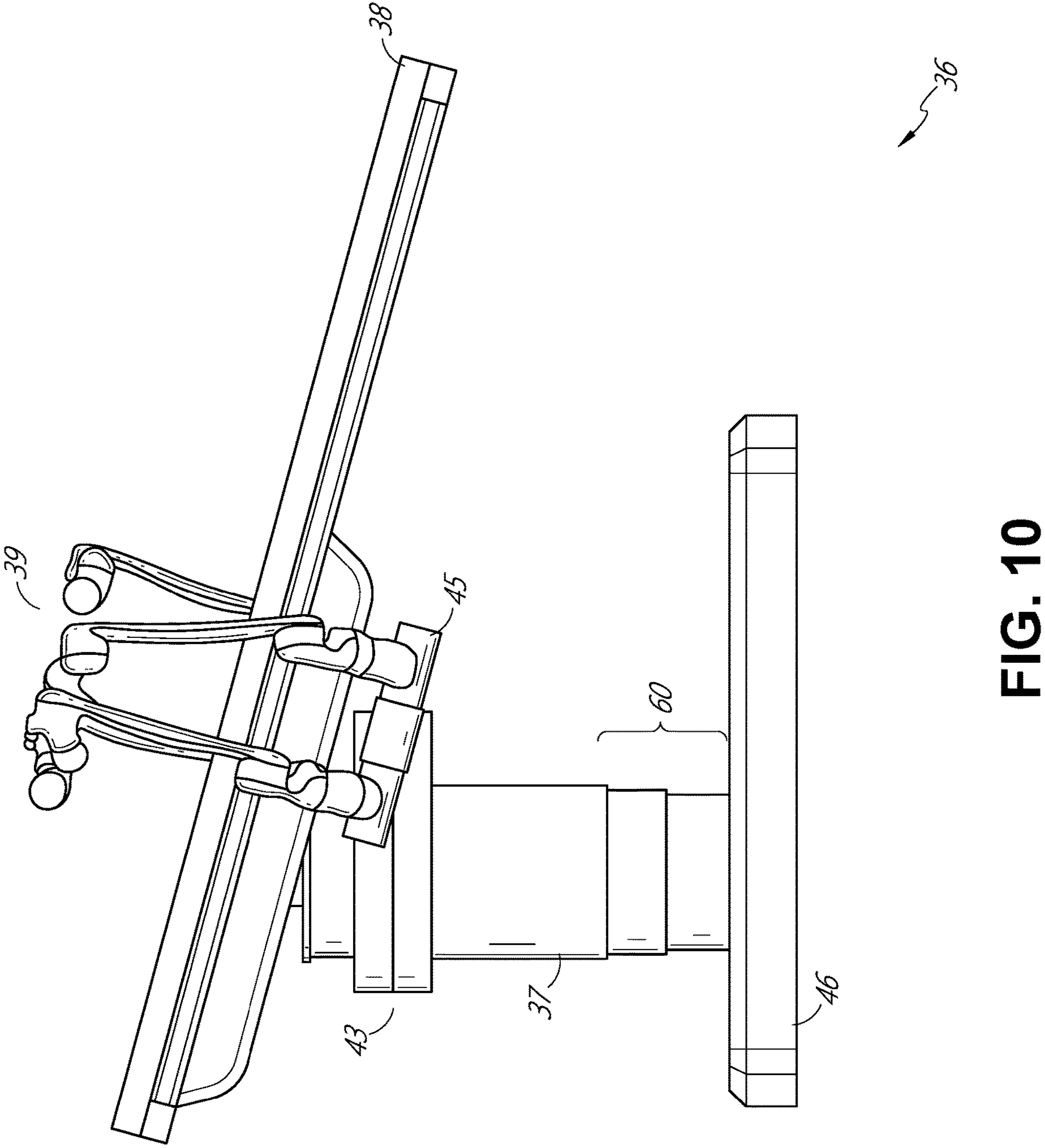
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the arms 39 maintain the same planar relationship with table 38. To accommodate steeper angles, the column 37 may also include telescoping portions 60 that allow vertical extension of column 37 to keep the table 38 from touching the floor or colliding with base 46.

Figure 11:
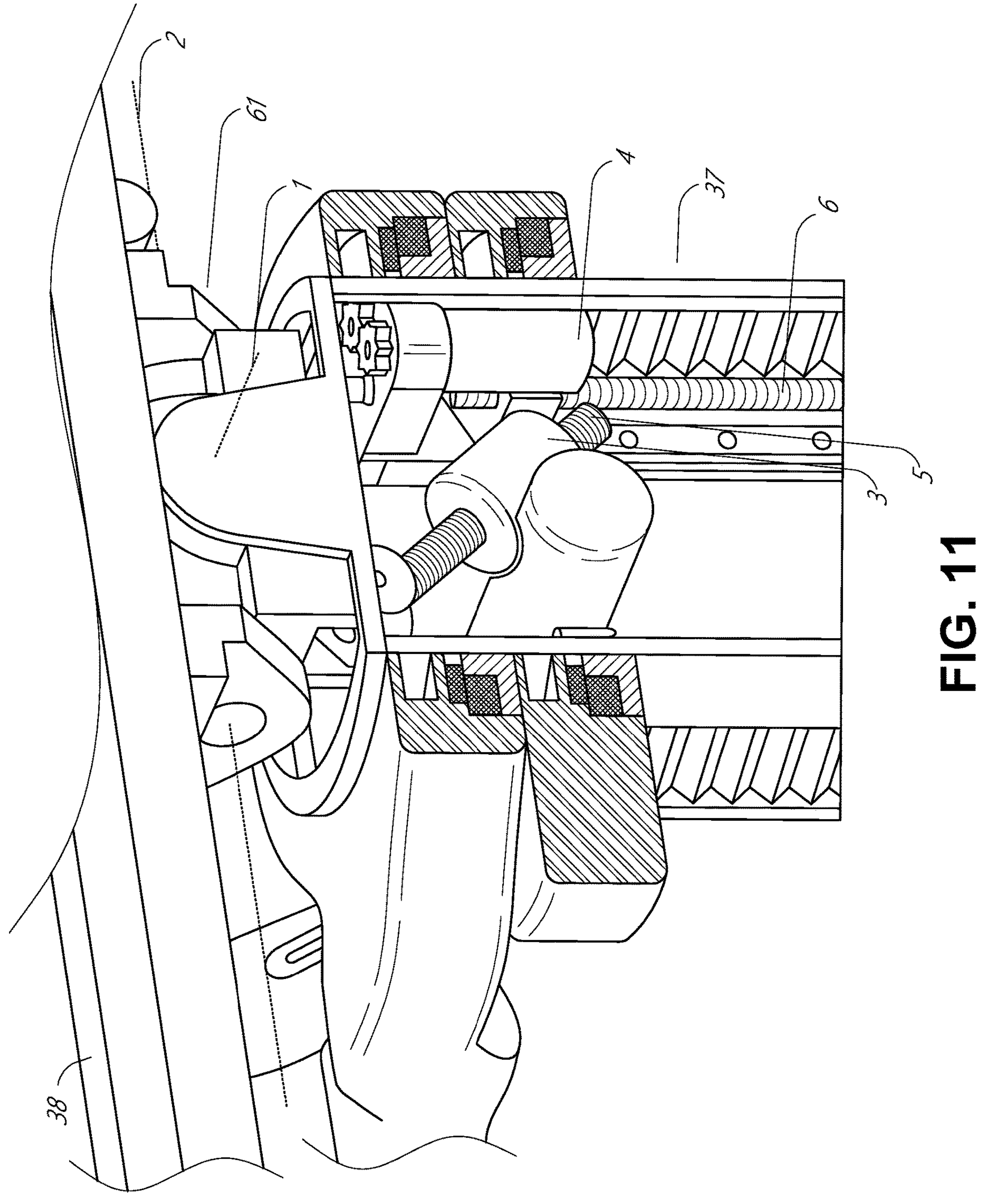
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
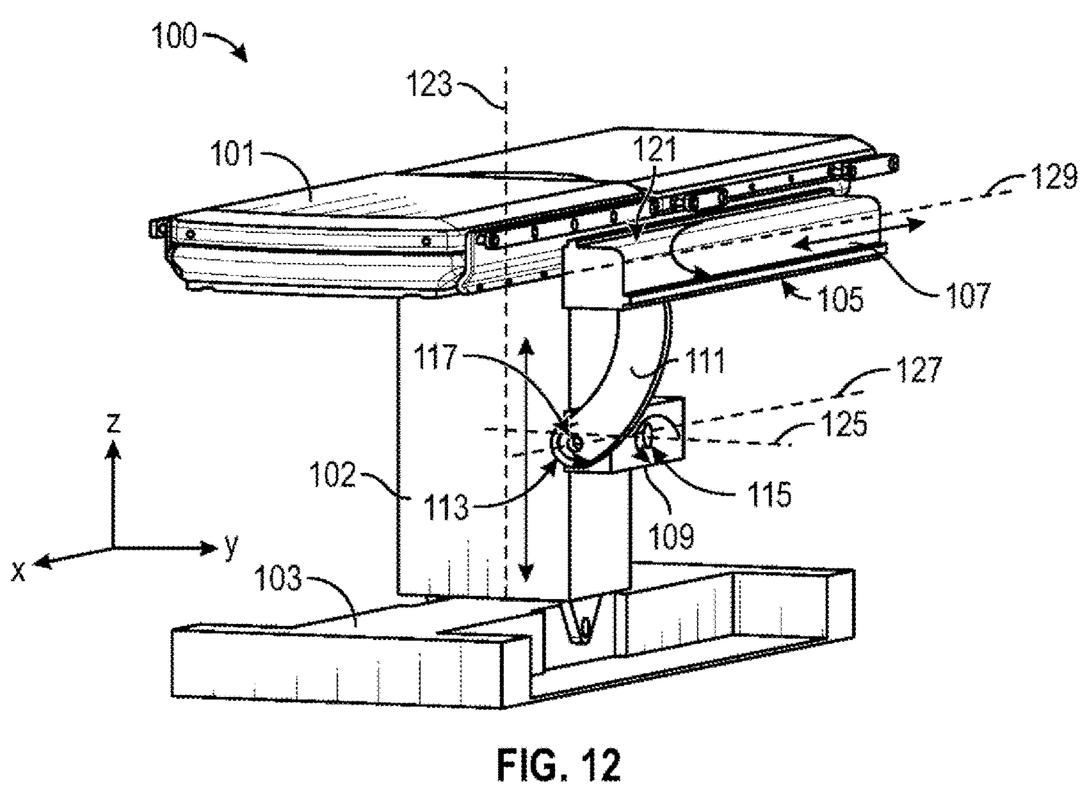
FIG. 12 illustrates an alternative embodiment of a table-based robotic system.
Figure 13:
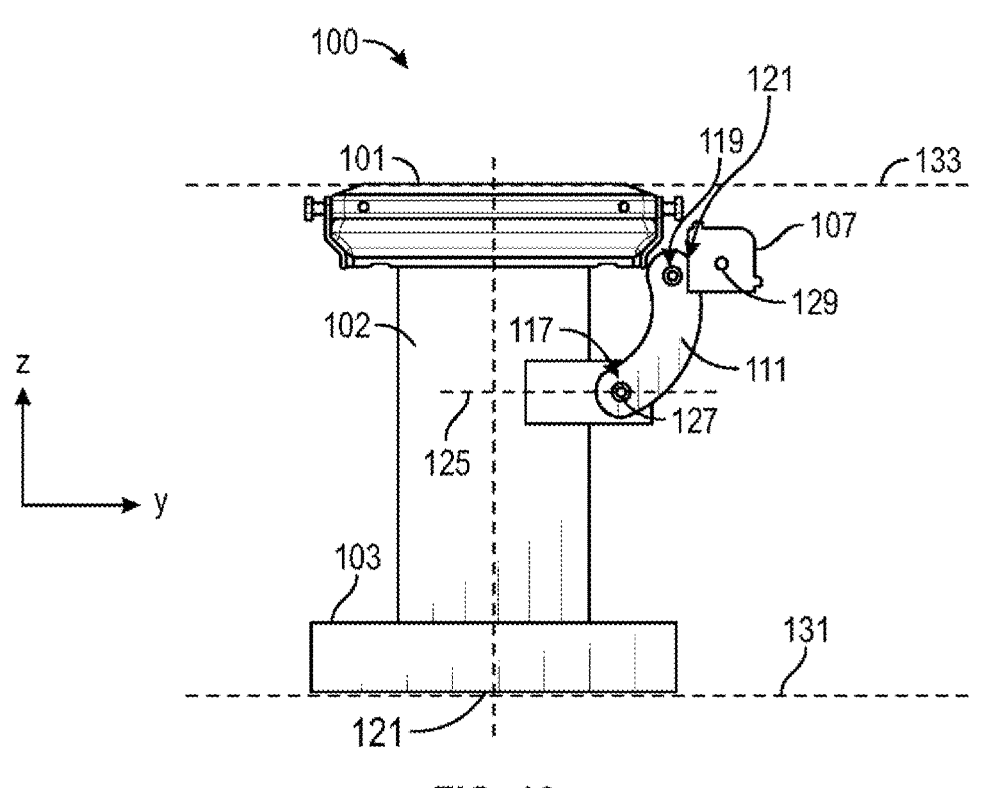
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
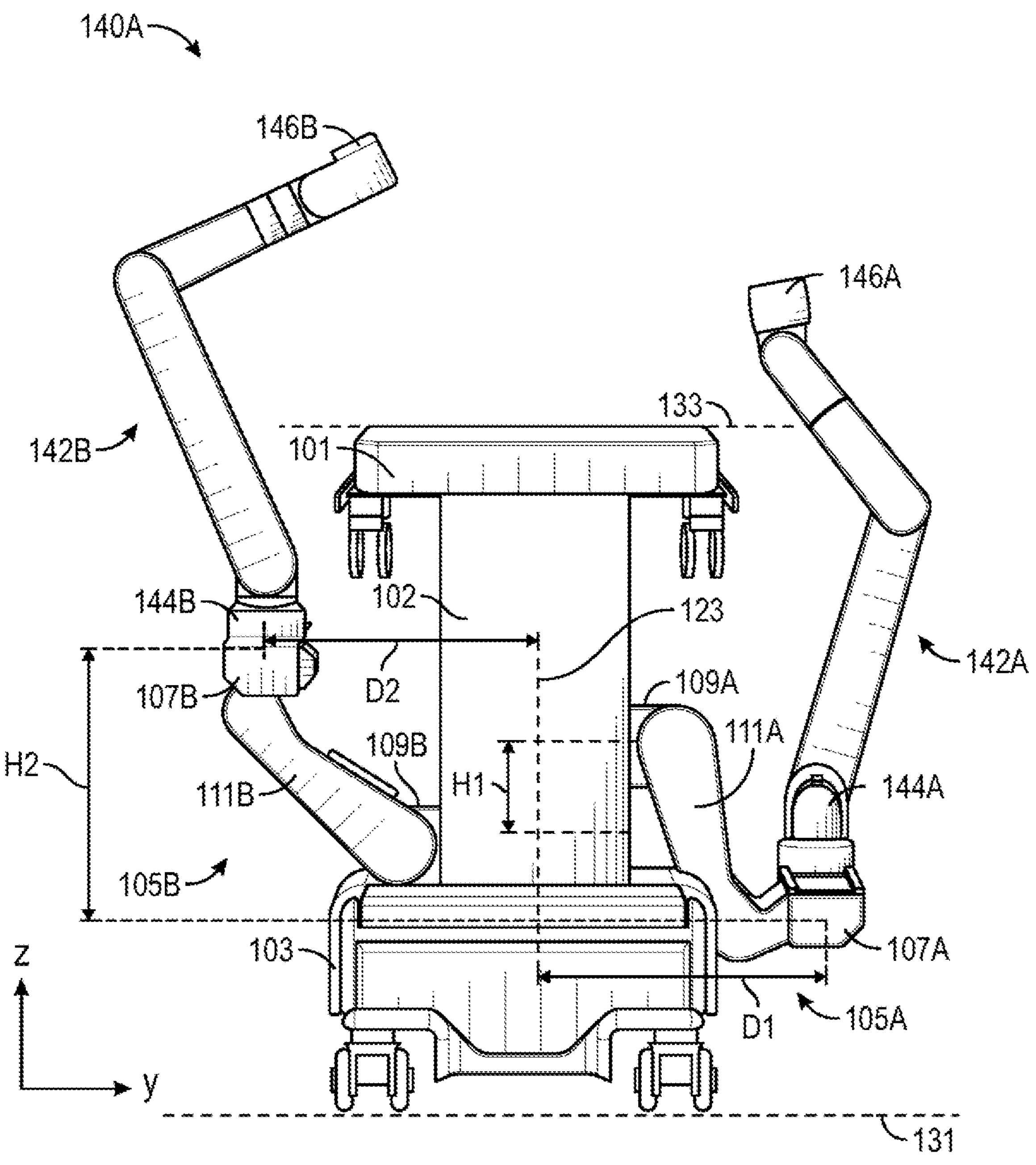
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms comprise (i) an instrument driver (alternatively referred to as "instrument drive mechanism" or "instrument device manipulator") that incorporate electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
FIG. 15 illustrates an exemplary instrument driver.
Figure 15:
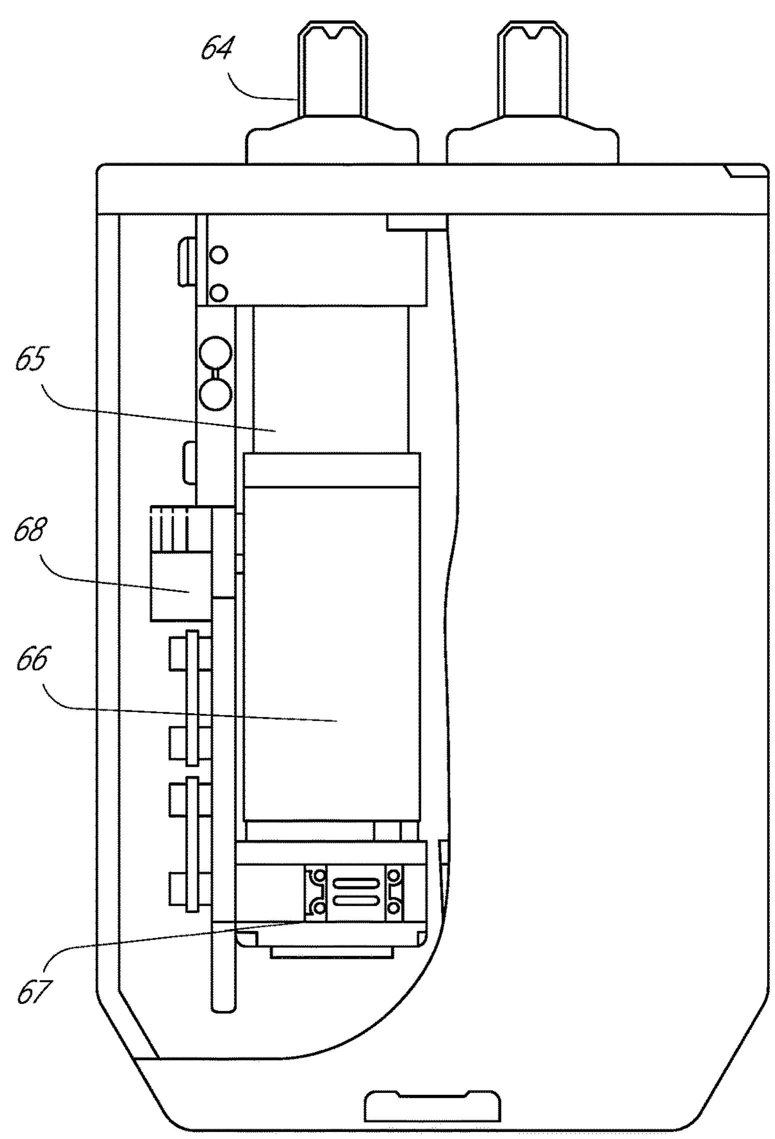
Figure 15:

FIG. 15 illustrates an example instrument driver. Positioned at the distal end of a robotic arm, instrument driver 62 comprises of one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independent controlled and motorized, the instrument driver 62 may provide multiple (four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
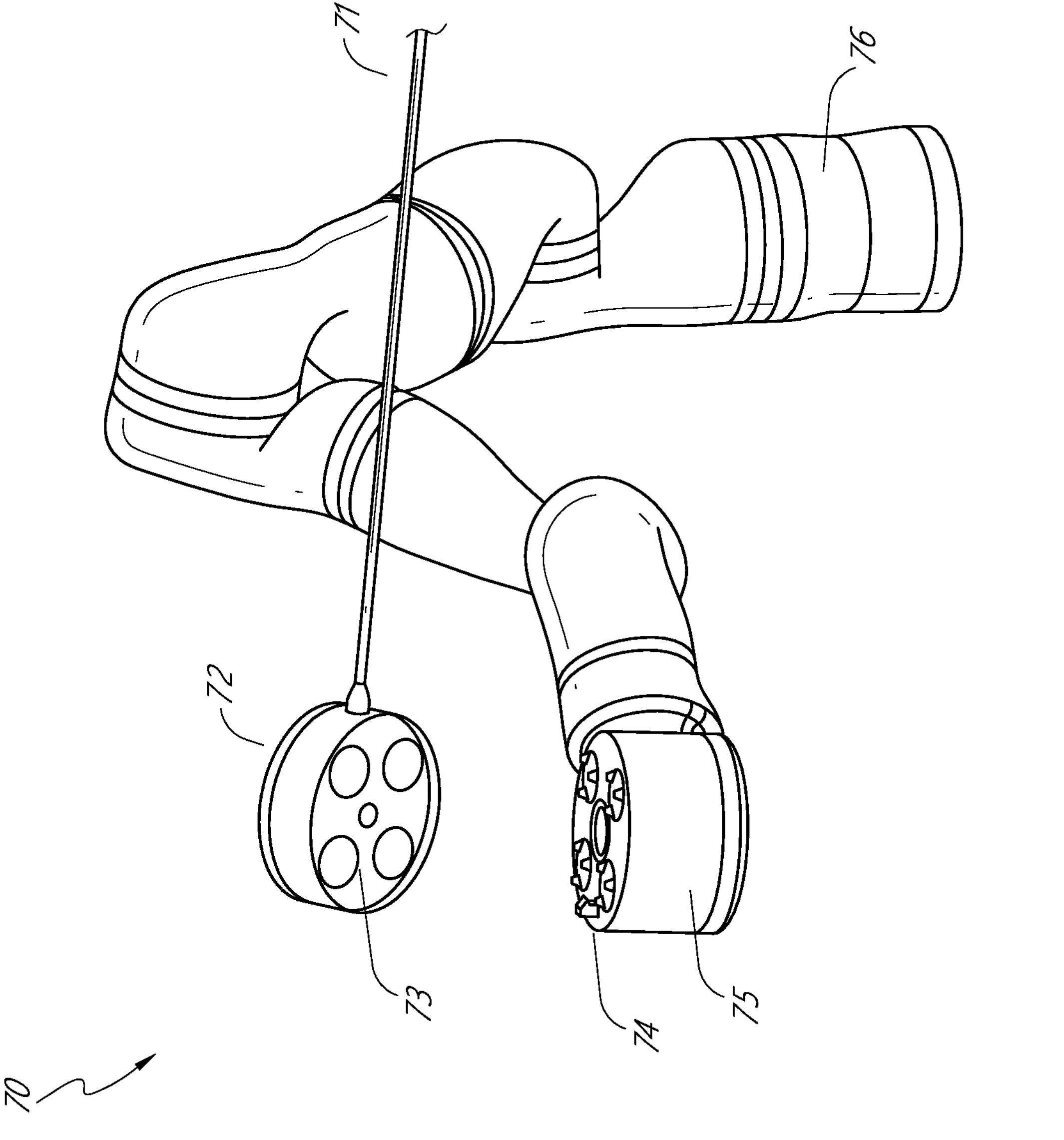
FIG. 16 illustrates an exemplary medical instrument with a paired instrument driver.

FIG. 16 illustrates an example medical instrument with a paired instrument driver Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of instrument base 72 may share axes of rotation with the drive outputs 74 in the instrument driver 75 to allow the transfer of torque from drive outputs 74 to drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 71, where tension from the tendon cause the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endo scope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft may comprise of a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include of an optical camera. The shaft 71 may also accommodate optical fibers to carry light from proximally-located light sources, such as light emitting diodes, to the distal end of the shaft.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft during an endoscopic procedure.

Figure 17:
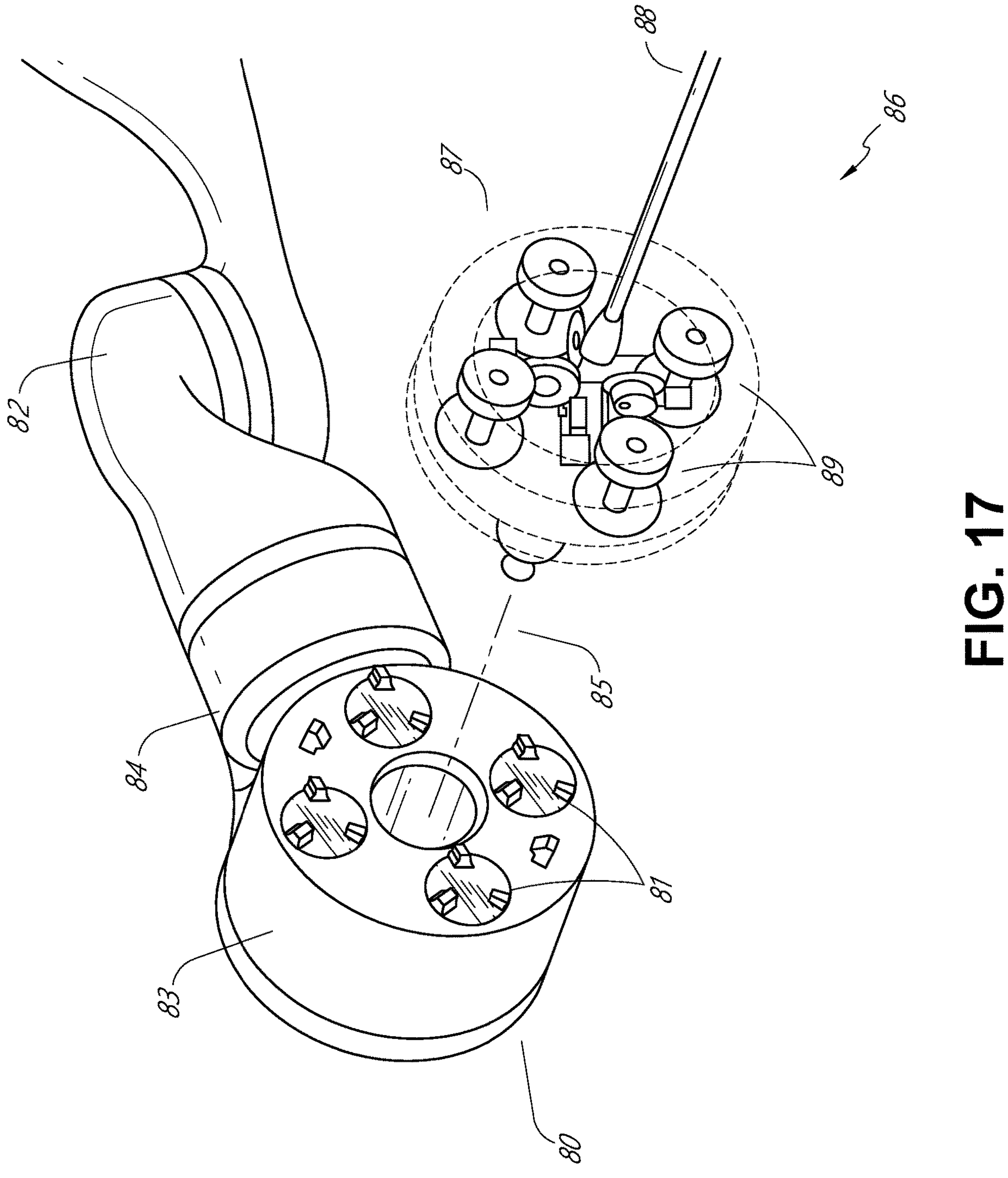
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver. Power and controls signals may be communicated from the non-rotational portion 84 of the instrument driver 80 to the rotational assembly 83 through electrical contacts and may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, instrument shaft 88 extends from the center of instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
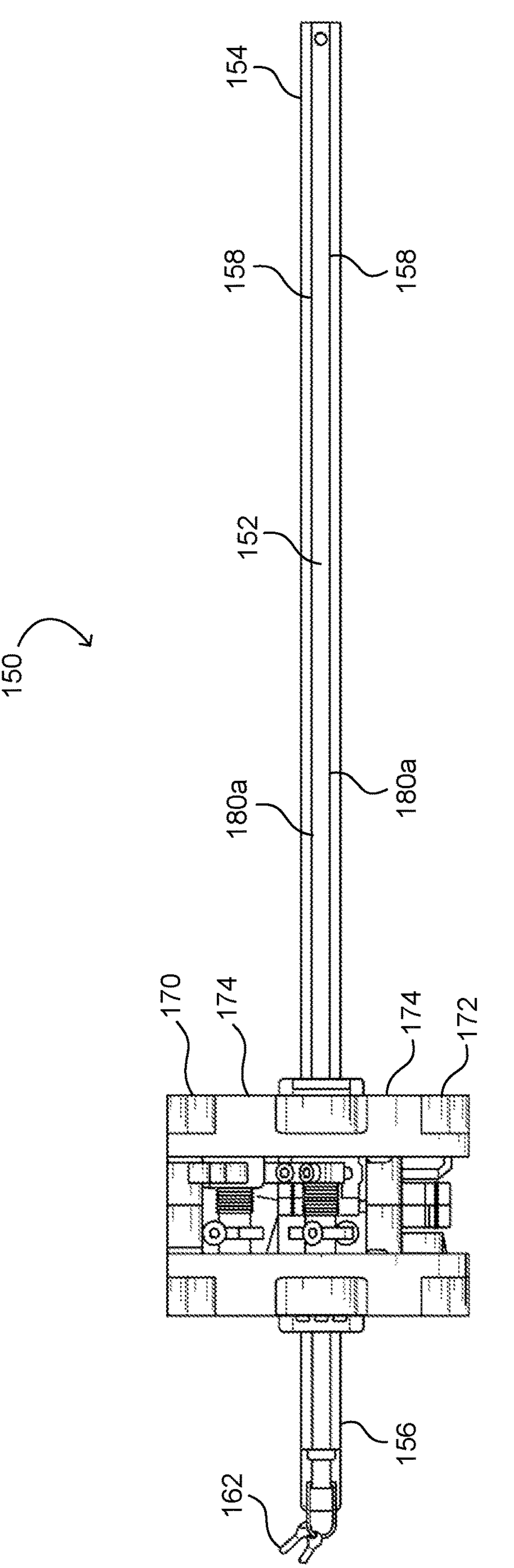
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
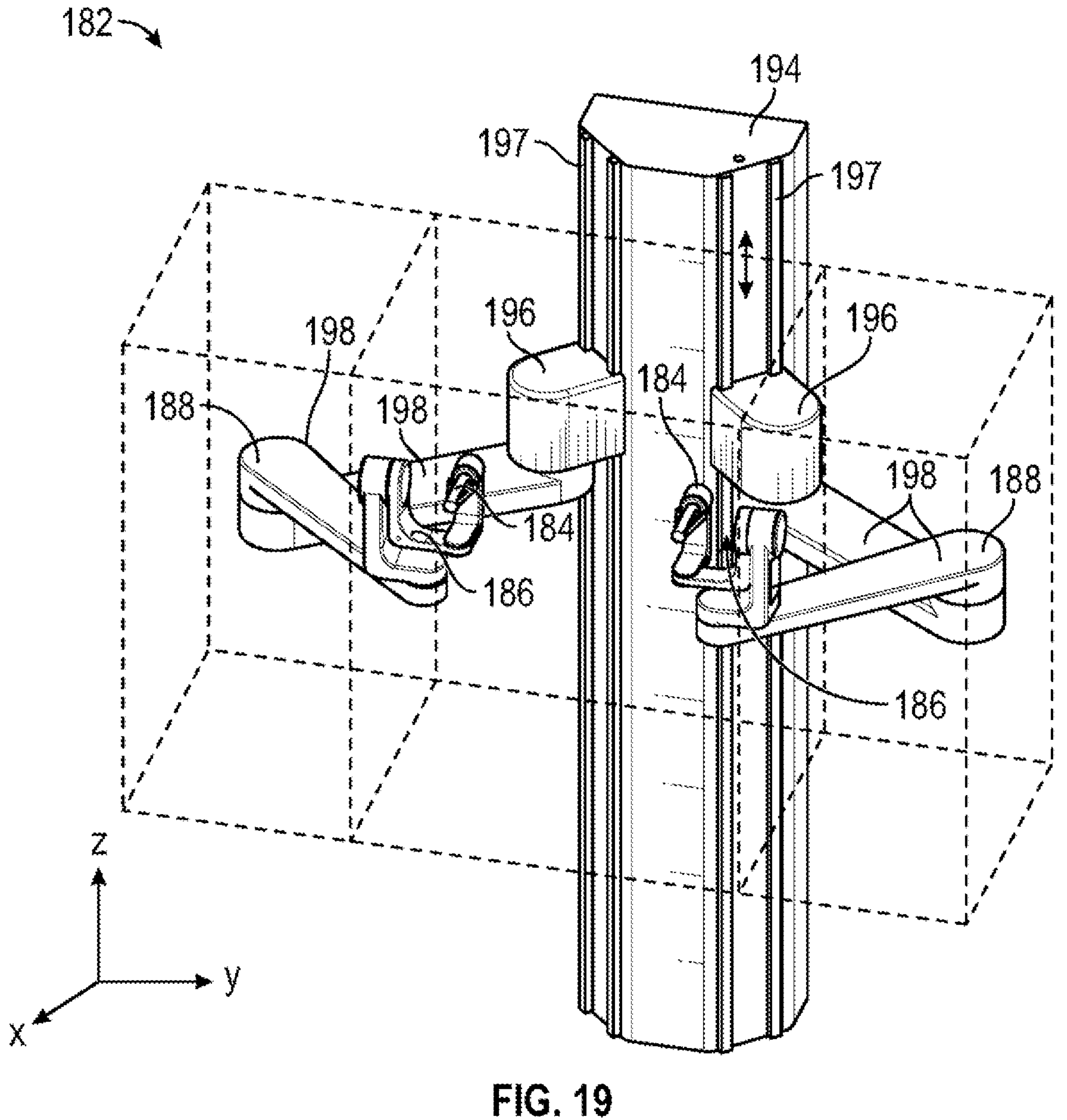
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 20:
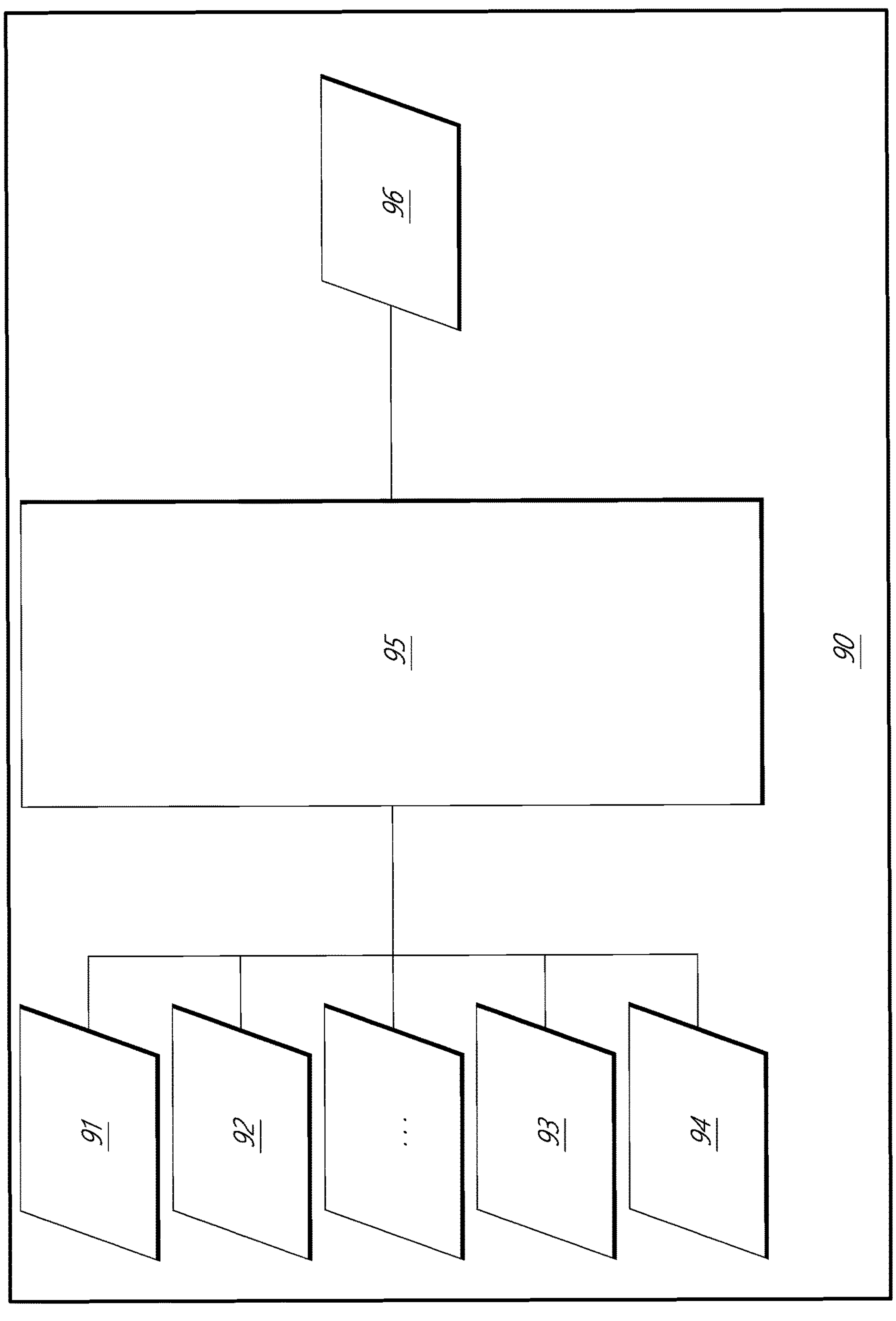
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 92. The localization module 95 may process the vision data to enable one or more vision-based location tracking. For example, the preoperative model data may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Systems, Devices, and Methods for Detecting and Responding to External Forces and/or Torques on a Robotic Arm Embodiments of the disclosure relate to systems, methods, and devices for detecting and responding to interactions with a robotic arm (e.g., inadvertent contact or collisions, direct manipulations, etc.), while teleoperation of the robotic arm is performed.

In accordance with some embodiments of the present disclosure, a robotic medical system includes one or more sensors and/or a sensor architecture, for sensing interactions on a robotic arm (e.g., on linkages, joints, etc. of the robotic arm). For example, a robotic arm may make contact with adjacent objects (e.g., patient, medical personnel, and/or accessories in the operating room) during teleoperation (e.g., surgery, diagnostic procedures, etc.). The sensors and/or sensor architecture detects and, optionally, measures interactions (e.g., forces, contact, displacement, torque, etc.) on the robotic arm.

When the measured interactions approach a safe contact limit (e.g., a safe force limit and/or torque limit) for the patient, medical personnel, and/or accessories, the robotic system must respond appropriately, to ensure that the contact force on the robotic manipulator does not go beyond a safe contact limit. In response to detecting the interactions, and in accordance with a determination of characteristic(s) (e.g., magnitude, direction, rate of change etc.) of the interactions, for example, the robotic system can enable appropriate controlled movements on the robotic arm, such as enable null space motion of the robotic arm, and/or move one or more joints and/or links of the robotic arm with a speed and/or direction (e.g., speed and/or direction requested by teleoperation, other speed and/or direction (e.g., null space motion, prohibition of motion, etc.)) that are selected in accordance with the characteristics of detected force and/or torque.

When the measured interactions approach a safe contact limit, the robotic system also provide haptic or other types of feedback to the surgeon, so that the surgeon operate the robotic system within the safe contact limits of the system. For example, the robotic system can provide feedback in the form of an output to a physician console display or as haptic feedback, in accordance with some embodiments.

A. Robotic System

Figure 21:
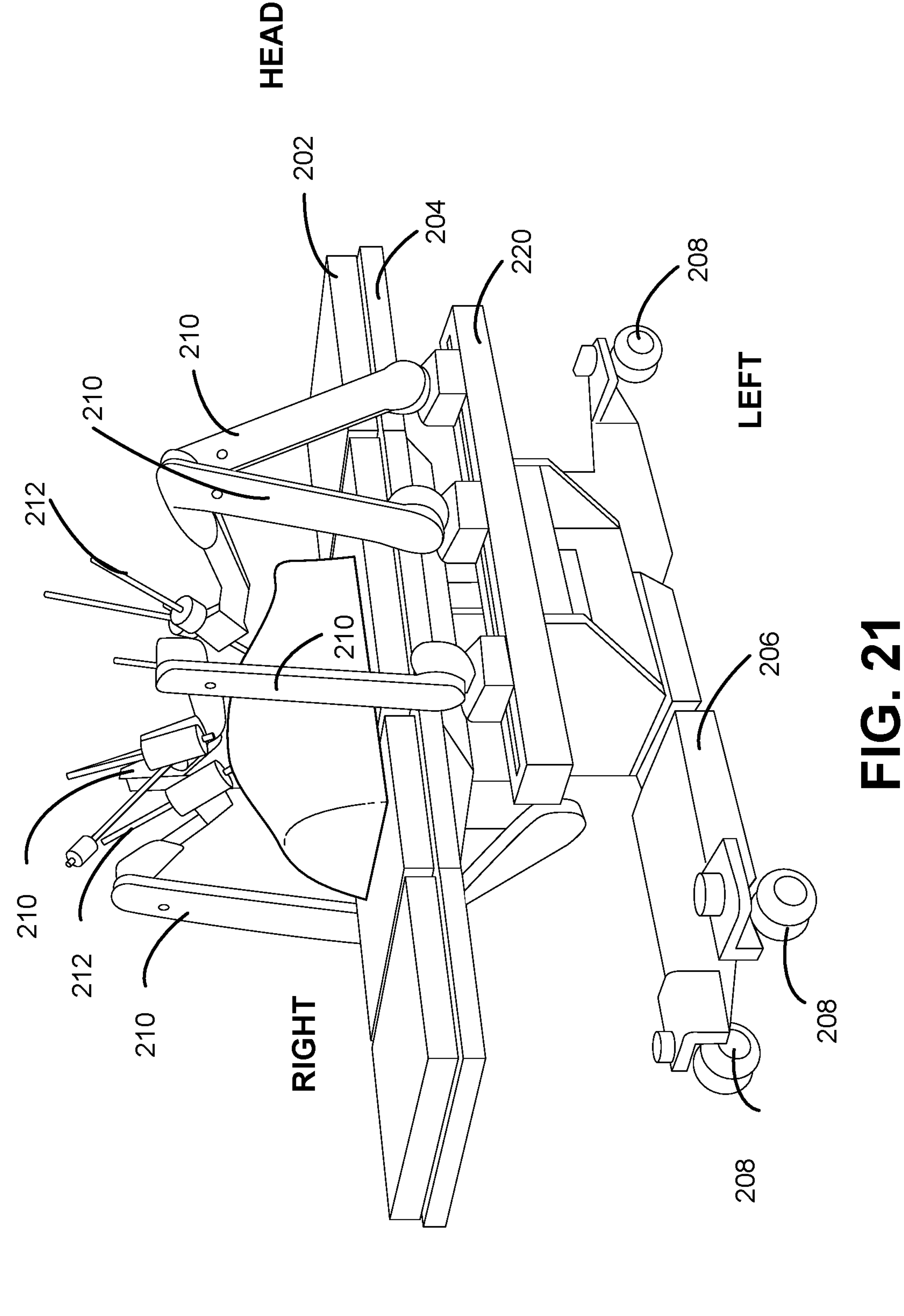
FIG. 21 illustrates an exemplary robotic system according to some embodiments.

FIG. 21 illustrates an exemplary robotic system 200 according to some embodiments. In some embodiments, the robotic system 200 is a robotic medical system (e.g., robotic surgery system). In the example of FIG. 21, the robotic system 200 includes a patient support platform 202 (e.g., a patient platform, a table, a bed, etc.). The two ends along the length of the patient support platform 202 are respectively referred to as "head" and "leg". The two sides of the patient support platform 202 are respectively referred to as "left" and "right." The patient support platform 202 includes a support 204 (e.g., a rigid frame) for the patient support platform 202.

The robotic system 200 also includes a base 206 for supporting the robotic system 200. The base 206 includes wheels 208 that allow the robotic system 200 to be easily movable or repositionable in a physical environment. In some embodiments, the wheels 208 are omitted from the robotic system 200 or are retractable, and the base 206 can rest directly on the ground or floor. In some embodiments, the wheels 208 are replaced with feet.

The robotic system 200 includes one or more robotic arms 210. The robotic arms 210 can be configured to perform robotic medical procedures as described above with reference to FIGS. 1-20. Although FIG. 21 shows five robotic arms 210, it should be appreciated that the robotic system 200 may include any number of robotic arms, including less than five or six or more.

The robotic system 200 also includes one or more bars 220 (e.g., adjustable arm support or an adjustable bar) that support the robotic arms 210. Each of the robotic arms 210 is supported on, and movably coupled to, a bar 220, by a respective base joint of the robotic arm. In some embodiments, and as described in FIG. 12, bar 220 can provide several degrees of freedom, including lift, lateral translation, tilt, etc. In some embodiments, each of the robotic arms 210 and/or the adjustable arm supports 220 is also referred to as a respective kinematic chain.

FIG. 21 shows three robotic arms 210 supported by the bar 220 that is in the field of view of the figure. The two remaining robotic arms are supported by another bar that is located across the other length of the patient support platform 202.

In some embodiments, the adjustable arm supports 220 can be configured to provide a base position for one or more of the robotic arms 210 for a robotic medical procedure. A robotic arm 210 can be positioned relative to the patient support platform 202 by translating the robotic arm 210 along a length of its underlying bar 220 and/or by adjusting a position and/or orientation of the robotic arm 210 via one or more joints and/or links (see, e.g., FIG. 23).

In some embodiments, the adjustable arm support 220 can be translated along a length of the patient support platform 202. In some embodiments, translation of the bar 220 along a length of the patient support platform 202 causes one or more of the robotic arms 210 supported by the bar 220 to be simultaneously translated with the bar or relative to the bar. In some embodiments, the bar 220 can be translated while keeping one or more of the robotic arms stationary with respect to the base 206 of the robotic medical system 200.

In the example of FIG. 21, the adjustable arm support 220 is located along a partial length of the patient support platform 202. In some embodiments, the adjustable arm support 220 may extend across an entire length of the patient support platform 202, and/or across a partial or full width of the patient support platform 202.

During a robotic medical procedure, one or more of the robotic arms 210 can also be configured to hold instruments 212 (e.g., robotically-controlled medical instruments or tools, such as an endoscope and/or any other instruments that may be used during surgery), and/or be coupled to one or more accessories, including one or more cannulas, in accordance with some embodiments.

Figure 22:
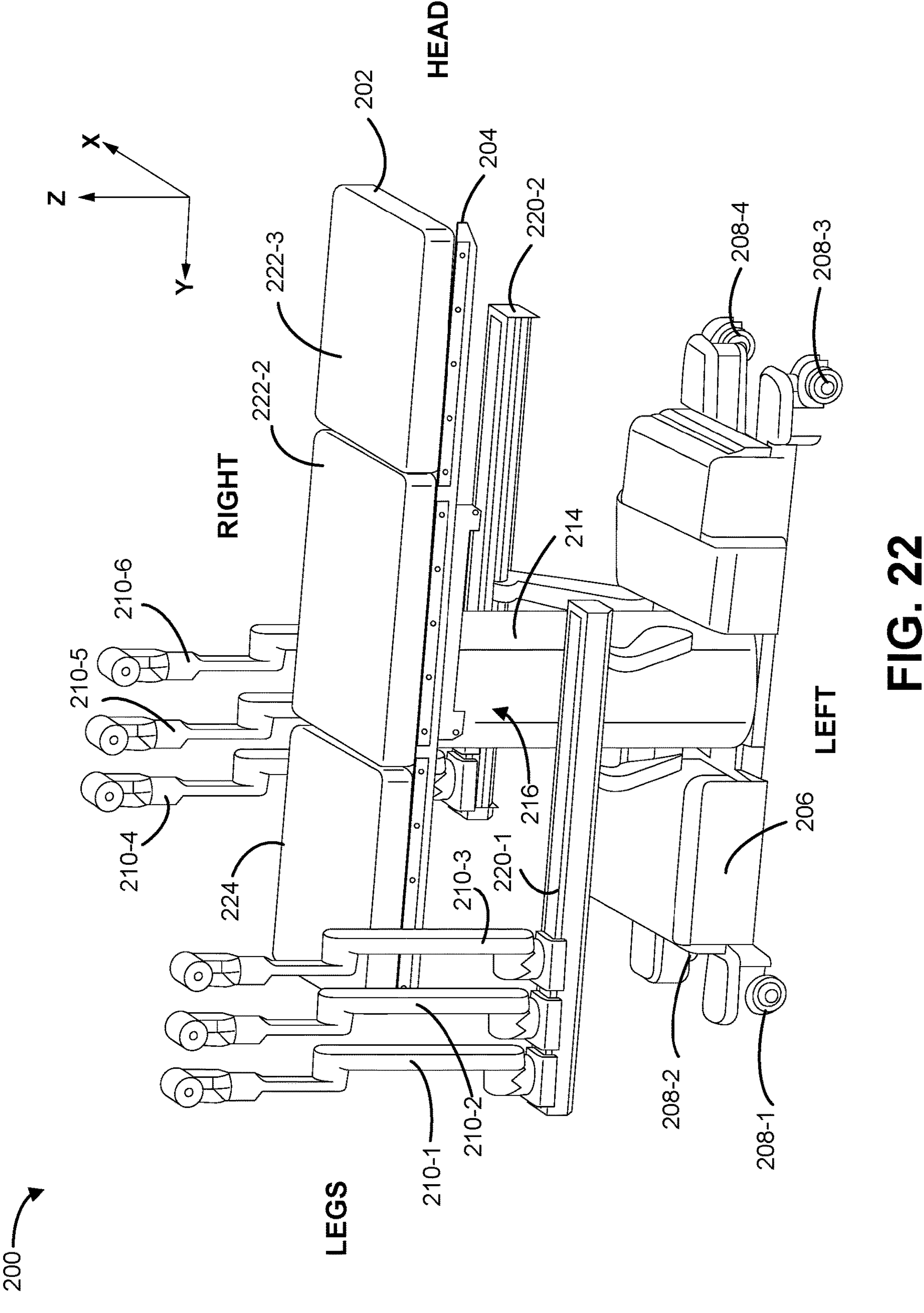
FIG. 22 illustrates another view of an exemplary robotic system according to some embodiments.

FIG. 22 illustrates another view of the exemplary robotic system 200 in FIG. 21 according to some embodiments. In this example, the robotic medical system 200 includes six robotic arms 210-1, 210-2, 210-3, 210-4, 210-5, and 210-6. The patient platform 202 is supported by a column 214 that extends between the base 206 and the patient platform 202. In some embodiments, the patient platform 202 includes a tilt mechanism 216. The tilt mechanism 216 can be positioned between the column 214 and the patient platform 202 to allow the patient platform to pivot, rotate, or tilt relative to the column 214. The tilt mechanism 216 can be configured to allow for lateral and/or longitudinal tilt of the patient platform 202. In some embodiments, the tilt mechanism 216 allows for simultaneous lateral and longitudinal tilt of the patient platform 202.

FIG. 22 shows the patient platform 202 in an untilted state or position. In some embodiments, the untilted state or position may be a default position of the patient platform 202. In some embodiments, the default position of the patient platform 202 is a substantially horizontal position as shown. As illustrated, in the untilted state, the patient platform 202 can be positioned horizontally or parallel to a surface that supports the robotic medical system 200 (e.g., the ground or floor).

With continued reference to FIG. 22, in the illustrated example of the robotic system 200, the patient platform 202 includes a support 204. In some embodiments, the support 204 includes a rigid support structure or frame, and can support one or more surfaces, pads, or cushions 222. An upper surface of the patient platform 202 can include a support surface 224. During a medical procedure, a patient can be placed on the support surface 224.

FIG. 22 shows the robotic arms 210 and the adjustable arm supports 220 in an exemplary deployed configuration in which the robotic arms 210 reach above the patient platform 202. In some embodiments, due to the configuration of the robotic system 200, which enables stowage of different components beneath the patient platform 202, the robotic arms 210 and the arm supports 220 can occupy a space underneath the patient platform 202. Thus, in some embodiments, it may be advantageous to configure the tilt mechanism 216 to have a low-profile and/or low volume to maximize the space available for storage below.

FIG. 22 also illustrates an example, x, y, and z coordinate system that may be used to describe certain features of the embodiments disclosed herein. It will be appreciated that this coordinate system is provided for purposes of example and explanation only and that other coordinate systems may be used. In the illustrated example, the x-direction or x-axis extends in a lateral direction across the patient platform 202 when the patient platform 202 is in an untilted state. That is, the x-direction extends across the patient platform 202 from one lateral side (e.g., the right side) to the other lateral side (e.g., the left side) when the patient platform 202 is in an untilted state. The y-direction or y-axis extends in a longitudinal direction along the patient platform 202 when the patient platform 202 is in an untilted state. That is, the y-direction extends along the patient platform 202 from one longitudinal end (e.g., the head end) to the other longitudinal end (e.g., the legs end) when the patient platform 202 is in an untilted state. In an untilted state, the patient platform 202 can lie in or be parallel to the x-y plane, which can be parallel to the floor or ground. In the illustrated example, the z-direction or z-axis extends along the column 214 in a vertical direction. In some embodiments, the tilt mechanism 216 is configured to laterally tilt the patient platform 202 by rotating the patient platform 202 about a lateral tilt axis that is parallel to the y-axis. The tilt mechanism 216 can further be configured to longitudinally tilt the patient platform 202 by rotating the patient platform 202 about a longitudinal tilt axis that is parallel to the x-axis.

B. Robotic Arm

Figures 23A, 23B:
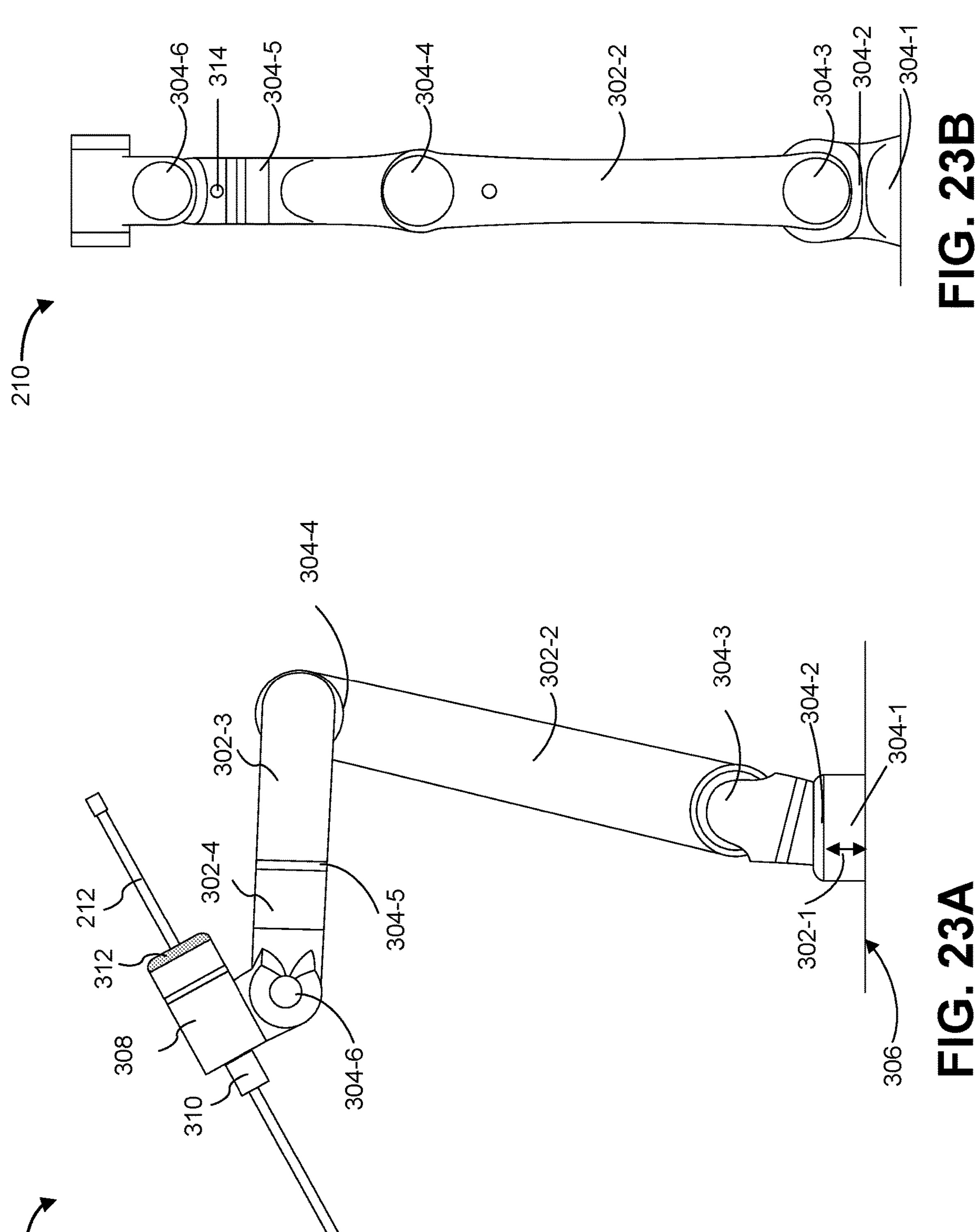
FIGS. 23A and 23B illustrate different views of an exemplary robotic arm according to some embodiments.

FIGS. 23A and 23B illustrate different views of an exemplary robotic arm 210 according to some embodiments.

FIG. 23A illustrates that the robotic arm 210 includes a plurality of links 302 (e.g., linkages). The links 302 are connected by one or more joints 304. Each of the joints 304 includes one or more degrees of freedom (DoFs).

In FIG. 23A, the joints 304 include a first joint 304-1 (e.g., a base joint or an A0 joint) that is located at or near a base 306 of the robotic arm 210. In some embodiments, the base joint 304-1 comprises a prismatic joint that allows the robotic arm 210 to translate along the bar 220 (e.g., along the y-axis). The joints 304 also include a second joint 304-2 (e.g., an A1 joint). In some embodiments, the second joint 304-2 rotates with respect to the base joint 304-1. The joints 304 also include a third joint 304-3 (e.g., an A2 joint) that is connected to one end of link 302-2. In some embodiments, the joint 304-3 includes multiple DoFs and facilitates both tilt and rotation of the link 302-2 tilt with respect to the joint 304-3.

FIG. 23A also shows a fourth joint 304-4 (e.g., an A3 joint) that is connected to the other end of the link 302-2. In some embodiments, the joint 304-4 comprises an elbow joint that connects the link 302-2 and the link 302-3. The joints 304 further include a pair of joints 304-5 (e.g., a wrist roll joint or an A4 joint) and 304-6 (e.g., a wrist pitch joint or an A5 joint), which is located on a distal portion of the robotic arm 210.

A proximal end of the robotic arm 210 may be connected to a base 306 and a distal end of the robotic arm 210 may be connected to an advanced device manipulator (ADM) 308 (e.g., a tool driver, an instrument driver, or a robotic end effector, etc.). The ADM 308 may be configured to control the positioning and manipulation of a medical instrument 212 (e.g., a tool, a scope, etc.).

The robotic arm 210 can also include a cannula sensor 310 for detecting presence or proximity of a cannula to the robotic arm 210. In some embodiments, the robotic arm 210 is placed in a docked state (e.g., docked position) when the cannula sensor 310 detects presence of a cannula (e.g., via one or more processors of the robotic system 200). In some embodiments, when the robotic arm 210 is in a docked position, the robotic arm 210 can execute null space motion to maintain a position and/or orientation of the cannula, as discussed in further detail below. Conversely, when no cannula is detected by the cannula sensor 310, the robotic arm 210 is placed in an undocked state (e.g., undocked position).

In some embodiments, and as illustrated in FIG. 23A, the robotic arm 210 includes an input or button 312 (e.g., a donut-shaped button, or other types of controls, etc.) that can be used to place the robotic arm 210 in an admittance mode (e.g., by depressing the button 312). The admittance mode is also referred to as an admittance scheme or admittance control. In the admittance mode, the robotic system 210 measures forces and/or torques (e.g., imparted on the robotic arm 210) and outputs corresponding velocities and/or positions. In some embodiments, the robotic arm 210 can be manually manipulated by a user (e.g., during a set-up procedure, or in between procedures, etc.) in the admittance mode. In some instances, by using admittance control, the operator need not overcome all of the inertia in the robotic system 200 to move the robotic arm 210. For example, under admittance control, when the operator imparts a force on the arm, the robotic system 200 can measure the force and assist the operator in moving the robotic arm 210 by driving one or more motors associated with the robotic arm 210, thereby resulting in desired velocities and/or positions of the robotic arm 210.

In some embodiments, the links 302 may be detachably coupled to the medical tool 212 (e.g., to facilitate ease of mounting and dismounting of the medical tool 212 from the robotic arm 210). The joints 304 provide the robotic arm 210 with a plurality of degrees of freedom (DoFs) that facilitate control of the medical tool 212 via the ADM 308.

FIG. 23B illustrates a front view of the robotic arm 210. In some embodiments, the robotic arm 210 includes a second input or button 314 (e.g., a push button) that is distinct from the button 312 in FIG. 23A, for placing the robotic arm 210 in an impedance mode (e.g., by a single press or continuous press and hold of the button 314). In this example, the button 314 is located between the A4 joint 304-5 and the A5 joint 304-6. The impedance mode is also referred to as impedance scheme or impedance control. In the impedance mode, the robotic system 200 measures displacements (e.g., changes in position and velocity) and outputs forces to facilitate manual movement of the robotic arm. In some embodiments, the robotic arm 210 can be manually manipulated by a user (e.g., during a set-up procedure) in the impedance mode. In some embodiments, under the impedance mode, the operator's movement of one part of a robotic arm 210 may back drive other parts of the robotic arm 210.

In some embodiments, for admittance control, a force sensor or load cell can measure the force that the operator is applying to the robotic arm 210 and move the robotic arm 210 in a way that feels light. Admittance control may feel lighter than impedance control because, under admittance control, one can hide the perceived inertia of the robotic arm 210 because motors in the controller can help to accelerate the mass. In contrast, with impedance control, the user is responsible for most if not all mass acceleration, in accordance with some embodiments.

In some circumstances, depending on the position of the robotic arm 210 relative to the operator, it may be inconvenient to reach the button 312 and/or the button 314 to activate a manual manipulating mode (e.g., the admittance mode and/or the impedance mode). Accordingly, under these circumstances, it may be convenient for the operator to trigger the manual manipulation mode other than by buttons.

In some embodiments, the robotic arm 210 includes a single button that can be used to place the robotic arm 210 in the admittance mode and the impedance mode (e.g., by using different presses, such as a long press, a short press, press and hold etc.). In some embodiments, the robotic arm 210 can be placed in impedance mode by a user pushing on arm linkages (e.g., the links 302) and/or joints (e.g., the joints 304) and overcoming a force threshold.

During a medical procedure, it can be desirable to have the ADM 308 of the robotic arm 210 and/or a remote center of motion (RCM) of the tool 212 coupled thereto kept in a static pose (e.g., position and/or orientation). An RCM may refer to a point in space where a cannula or other access port through which a medical tool 212 is inserted is constrained in motion. In some embodiments, the medical tool 212 includes an end effector that is inserted through an incision or natural orifice of a patient while maintaining the RCM. In some embodiments, the medical tool 212 includes an end effector that is in a retracted state during a setup process of the robotic medical system.

In some circumstances, the robotic system 200 can be configured to move one or more links 302 of the robotic arm 210 within a "null space" to avoid collisions with nearby objects (e.g., other robotic arms), while the ADM 308 of the robotic arm 210 and/or the RCM are maintained in their respective poses (e.g., positions and/or orientations). The null space can be viewed as the space in which a robotic arm 210 can move that does not result in movement of the ADM 308 and/or RCM, thereby maintaining the position and/or the orientation of the medical tool 212 (e.g., within a patient). In some embodiments, a robotic arm 210 can have multiple positions and/or configurations available for each pose of the ADM 308.

For a robotic arm 210 to move the ADM 308 to a desired pose in space, in certain embodiments, the robotic arm 210 may have at least six DoFs—three DoFs for translation (e.g., X, Y, and Z positions) and three DoFs for rotation (e.g., yaw, pitch, and roll). In some embodiments, each joint 304 may provide the robotic arm 210 with a single DoF, and thus, the robotic arm 210 may have at least six joints to achieve freedom of motion to position the ADM 308 at any pose in space. To further maintain the ADM 308 of the robotic arm 210 and/or the remote center or motion in a desired pose, the robotic arm 210 may further have at least one additional "redundant joint." Thus, in certain embodiments, the system may include a robotic arm 210 having at least seven joints 304, providing the robotic arm 210 with at least seven DoFs. In some embodiments, the robotic arm 210 may include a subset of joints 304 each having more than one degree of freedom thereby achieving the additional DoFs for null space motion. However, depending on the embodiment, the robotic arm 210 may have a greater or fewer number of DoFs.

Furthermore, as described in FIG. 12, the bar 220 (e.g., adjustable arm support) can provide several degrees of freedom, including lift, lateral translation, tilt, etc. Thus, depending on the embodiment, a robotic medical system can have many more robotically controlled degrees of freedom beyond just those in the robotic arms 210 to provide for null space movement and collision avoidance. In a respective embodiment of these embodiments, the end effectors of one or more robotic arms (and any tools or instruments coupled thereto) and a remote center along the axis of the tool can advantageously maintain in pose and/or position within a patient.

A robotic arm 210 having at least one redundant DoF has at least one more DoF than the minimum number of DoFs for performing a given task. For example, a robotic arm 210 can have at least seven DoFs, where one of the joints 304 of the robotic arm 210 can be considered a redundant joint, in accordance with some embodiments. The one or more redundant joints can allow the robotic arm 210 to move in a null space to both maintain the pose of the ADM 308 and a position of an RCM and avoid collision(s) with other robotic arms or objects.

In some embodiments, the robotic system 200 can be configured to perform collision avoidance to avoid collision(s), e.g., between adjacent robotic arms 210, by taking advantage of the movement of one or more redundant joints in a null space. For example, when a robotic arm 210 collides with or approaches (e.g., within a defined distance of) another robotic arm 210, one or more processors of the robotic system 200 can be configured to detect the collision or impending collision (e.g., via kinematics). Accordingly, the robotic system 200 can control one or both of the robotic arms 210 to adjust their respective joints within the null space to avoid the collision or impending collision. In an embodiment including at least a pair of robotic arms, a base of one of the robotic arms and its end effector can stay in its pose, while links or joints therebetween move in a null space to avoid collisions with an adjacent robotic arm.

C. Sensors

FIGS. 24A-24H illustrate sensors of a robotic arm 210 according to some embodiments. In some embodiments, each of the robotic arms 210 includes different sensors that can be used to detect contact between the robotic arm 210 and one or more external objects. Depending on the amount of force, torque etc. detected, the robotic system 200 can enable controlled movements on the robotic arm 210 in accordance with the amount and/or direction of detected contact force or torque, in accordance with some embodiments.

In some embodiments, the sensors are part of a sensor architecture. The sensor architecture may include other components for communicating sensor data, e.g., sensor attributes or parameters (e.g., force, contact, moment, displacement, movement, position, etc.) and values (e.g., location, magnitude, timing, duration, etc.) from the sensors to one or more processors of the robotic system 200, in accordance with some embodiments.

Figure 24A:
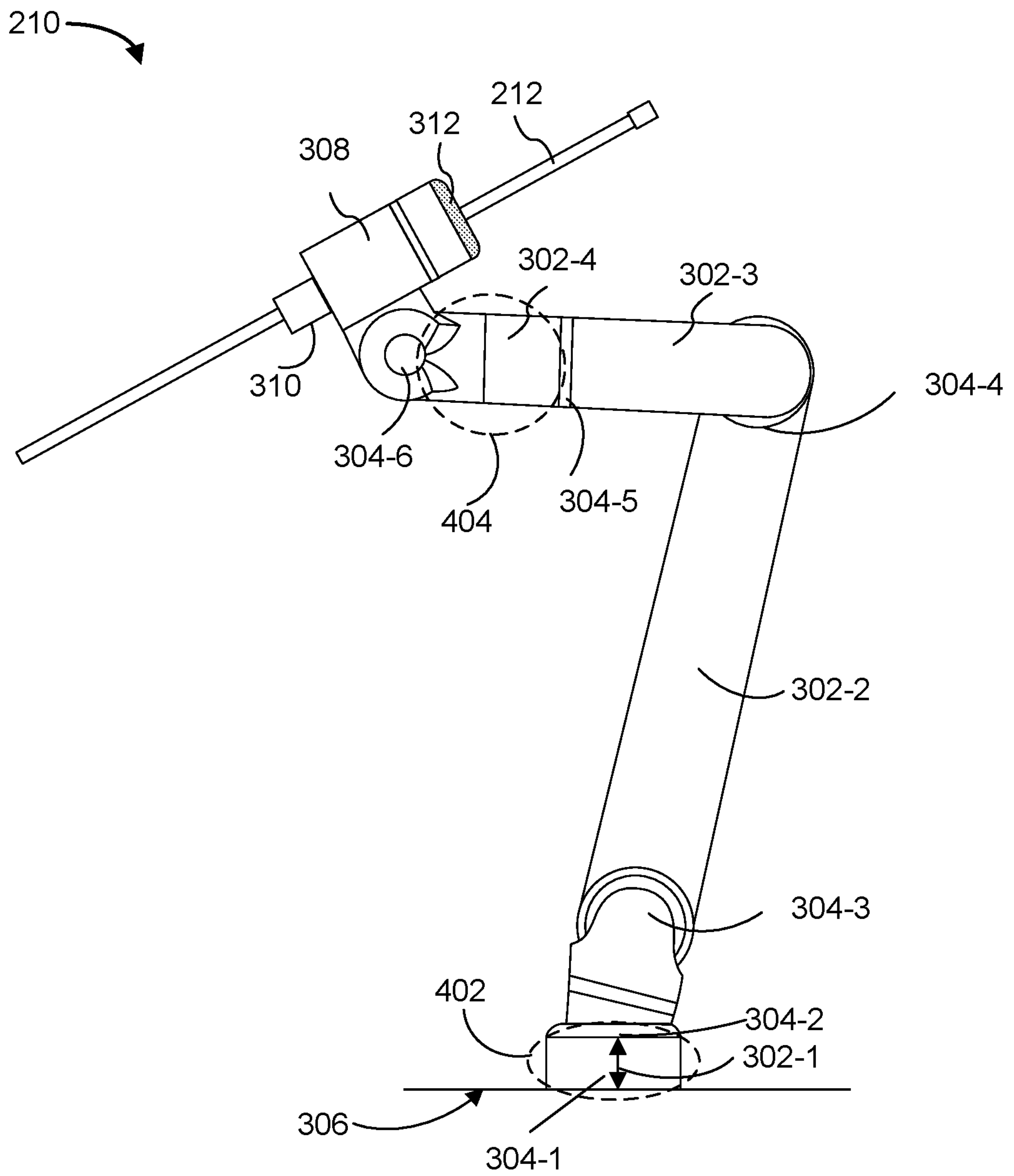

In some embodiments, the sensors comprise one or more joint sensors (e.g., joint based sensors). FIG. 24A illustrates a joint sensor 402 (e.g., an A0 joint sensor) that is located on the joint 304-1 (e.g., base joint or A0 joint), near the base 306 of the robotic arm 210. In some embodiments the A0 joint sensor 402 comprises a force sensor that allows interaction forces to be detected on a proximal end of the robotic arm 210. In some embodiments, the A0 joint sensor 402 serves as activation detection for transitioning the robotic arm 210 from a position control mode to a manual manipulation mode (e.g., an impedance mode, an admittance mode, a grab-and-go mode, etc.).

In some embodiments, the sensors include other joint based sensors that are located on other joints of the robotic arm 210 (e.g., sensors that are located on the A1 joint 304-2, the A2 joint 304-3, the A3 joint 304-4 etc.).

In some embodiments, the sensors comprise one or more non-joint based sensors. The non-joint based sensors can be located along a length of a link 302 of the robotic arm 210 and/or on the ADM 308. The sensors (both joint based and non-joint based) detect interactions between the robotic arm 210 and an external object (e.g., an operator, a patient another robotic arm, a surgical tool, and/or an underlying bar 220).

In some embodiments, and as illustrated in FIG. 24A, the sensors also comprise a six-axis load cell 404. The six-axis load cell 404 is a force and moment sensor that can sense forces and moments (e.g., torque) in multiple directions (e.g., it can measure forces along the X, Y, and Z axes, as well as the moments about each axis). In FIG. 24A, the six-axis load cell 404 is located between a pair of joints on a distal portion of the arm 210 (e.g., between the A4 joint 304-5 and the A5 joint 304-6). The six-axis load cell 404 can serve as a support mount for a tool driver (e.g., the ADM 308). Accordingly, the six-axis load cell 404 can measure forces and/or moments to be detected on a distal of the robotic arm 210 (e.g., by the tool driver). In some embodiments, the six-axis load cell 404 is located directly between the A4 joint 304-5 and the A5 joint 304-6 without a link (e.g., without the link 302-4).

Figure 24B:
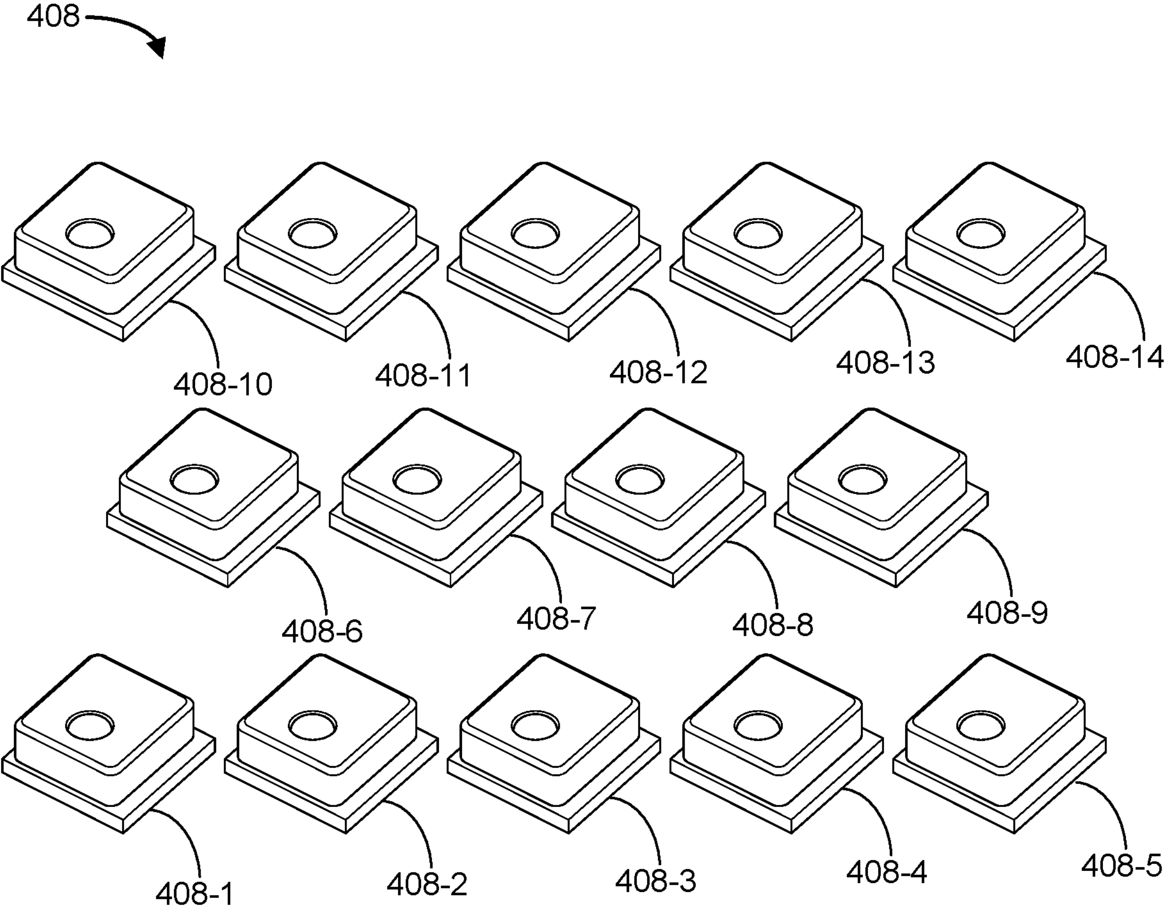

In some embodiments, the robotic arm 210 also includes contact sensors 408 (e.g., shell sensors). Although the example of FIG. 24B illustrates fourteen contact sensors (e.g., 408-1 to 408-14), it should be appreciated the robotic arm 210 can include any number of contact sensors 408. In some embodiments, the contact sensors 408 comprise force and/or moment sensors and can detect (e.g., sense and/or measure) forces and/or moments in multiple directions. In some embodiments, the contact sensors 408 are positioned on a joint 304 of the robotic arm. In some embodiments, the contact sensors are located along a length of a link 302, such as a link on a proximal portion and/or a link on a distal portion of the robotic arm 210.

Figure 24C:
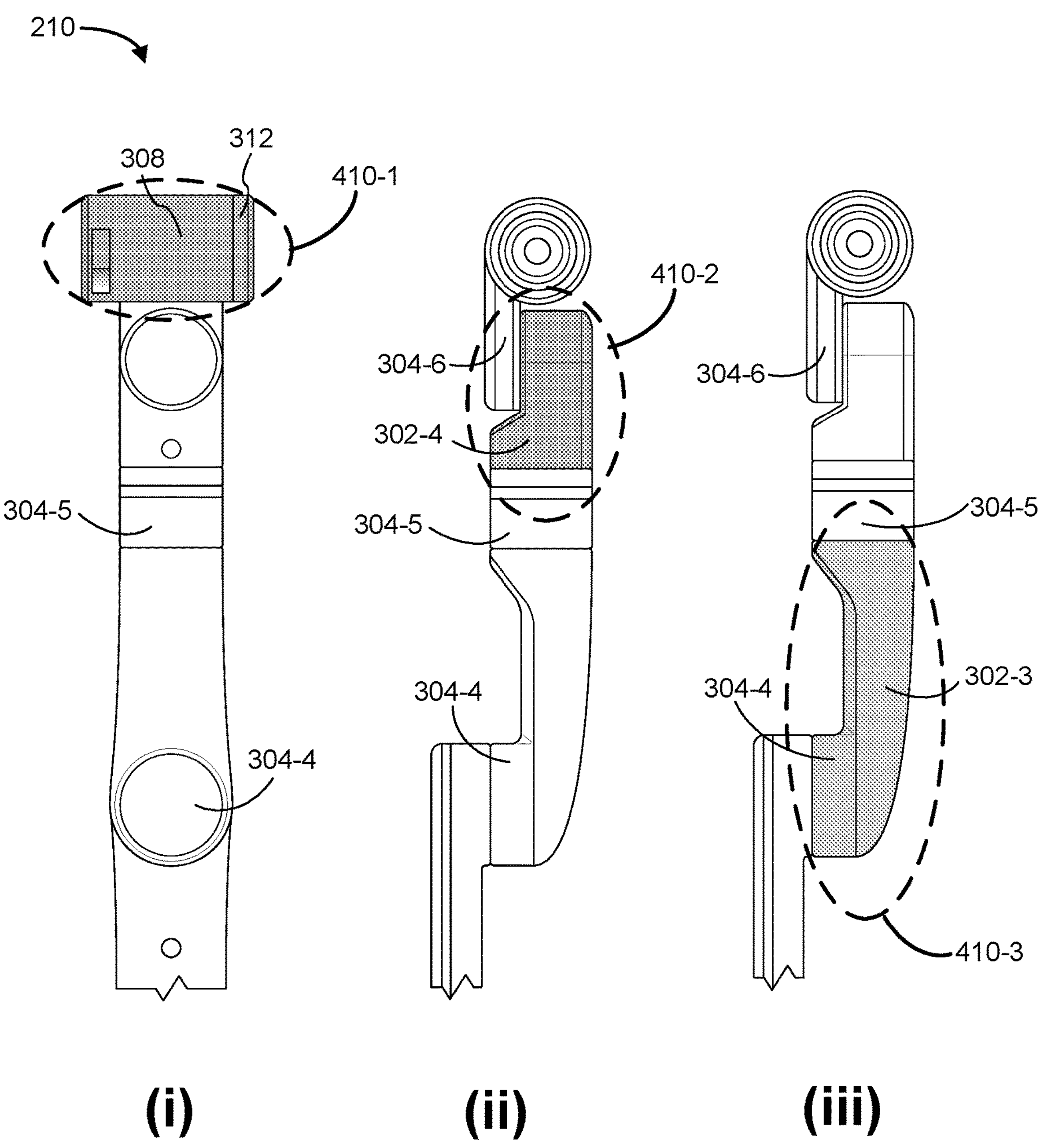
Figure 24D:
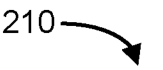

In some embodiments, the contact sensors 408 are located in areas of the robotic arm 210 that are known to regularly collide with a patient or medical personnel during surgery. FIG. 24C illustrates three views of a distal portion of the robotic arm 210, in which regions 410 that have a relatively higher likelihood of colliding with a patient are shaded. FIG. 24D illustrates three views of a proximal portion of the robotic arm 201 (e.g., proximal to the distal portion the robotic arm 210 in FIG. 24C), in which regions 412 that have a relatively higher likelihood of colliding with a patient or medical personnel are shaded.

Using the region 410-1 in FIG. 24C(i) as an example, in some embodiments, the ADM 308 includes one or more contact sensors 408 that detect interactions at or proximate to the ADM 308. In some embodiments, in accordance with a determination that a magnitude of the measured force and/or moment is between a lower contact force and/or torque limit and an upper contact force and/or torque limit, the robotic system 200 can enable controlled movement(s) on the robotic arm 210 in accordance with the detected contact force or torque. For example, the controlled movements may comprise movement of the robotic arm 210 in accordance with a user's command via a preset control mechanism (e.g., teleoperation, button control, etc.), in accordance with some embodiments. The controlled movements may also include movement of one or more joints and/or links of the robotic arm 210 to reduce the detected contact force or torque on the robotic arm, in accordance with some embodiments. The controlled movements may also include null space motion of the robotic arm 210, in accordance with some embodiments.

Additionally and/or alternatively, in some embodiments, interactions with the ADM (e.g., force and moment) may be detected by the six-axis load cell 404 on which the ADM is mounted (either directly or indirectly).

Figure 24E:
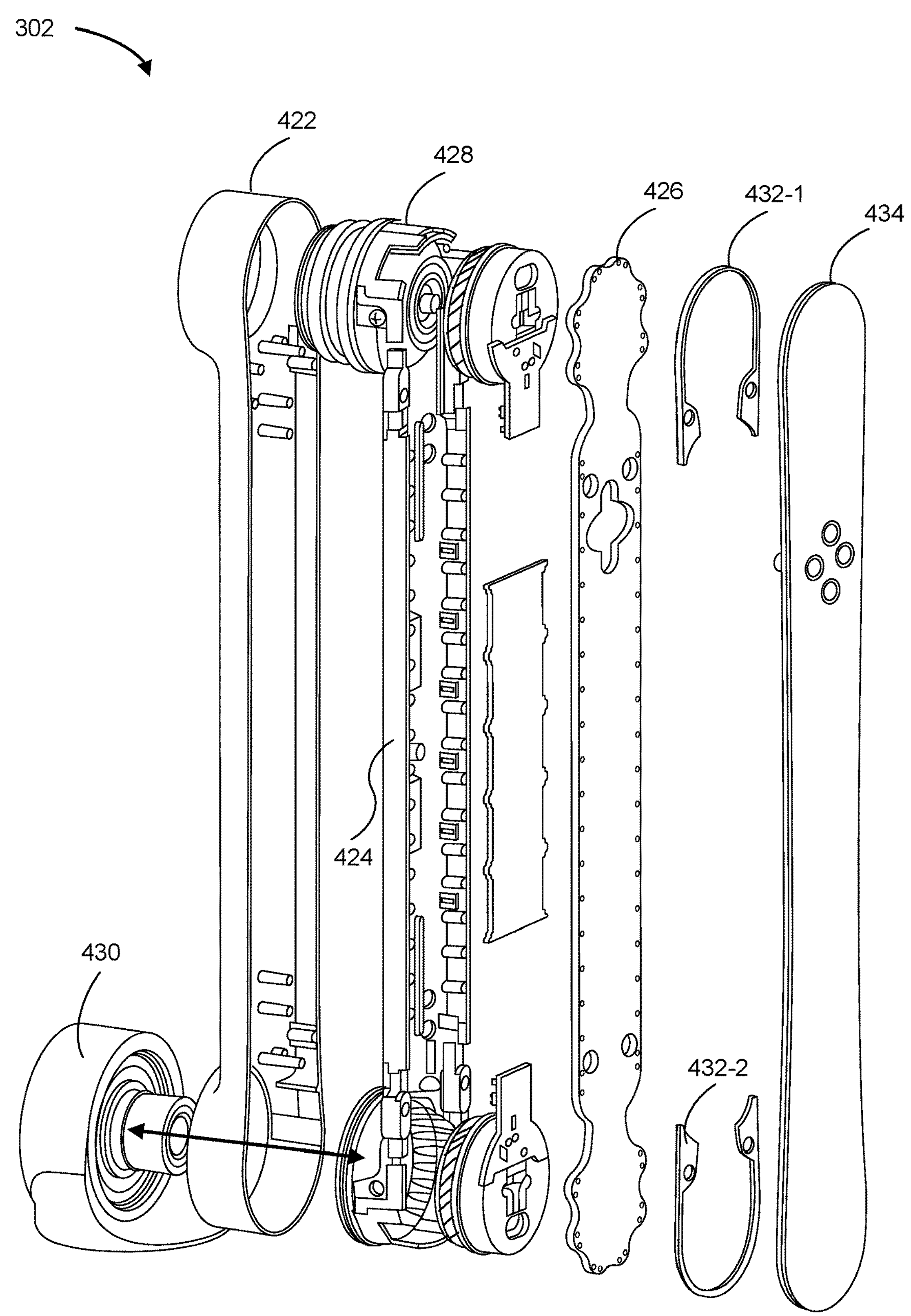

In some embodiments, the contact sensors 408 can have a suspended "shell" around an outside of a robotic arm link. FIG. 24E illustrates an exemplary link 302 of a robotic arm 210 according to some embodiments.

In some embodiments, and as illustrated in FIG. 24E, the link 302 comprises a rigid shell 422, a structural link 424, a structural cover 426, a first joint 430 (e.g., the A2 joint 304-3 in FIGS. 23A and 23B), a second joint 428 (e.g., the A3 joint 304-4 in FIGS. 23A and 23B), a pair of reaction paddles 432, and a shell cover 434 (e.g., a cosmetic cover). The structural cover 426 can be attached to the structural link 424 to house components of the structural link 424 and form an internal structural connection between the first joint 430 and the second joint 428, in accordance with some embodiments.

In some embodiments, the shell 422 is used for detecting contact on the robotic arm 210 (e.g., by an external object). For example, the shell 422 together with the shell cover 434 are suspended from and surround the structural link 424, in accordance with some embodiments. The relative motion between the shell 422 and inner components/members of the link 302 (e.g., the structural link 424 and the structural cover 426) can be detected using one or more sensors (e.g., the contact sensors 408) disposed along a length of the link 302 to determine contact with an external object, in accordance with some embodiments.

In some embodiments, one or more of the contact sensors 408 (e.g., shell sensors) are strategically disposed at various locations along a length of the link 302, between the structural link 424 and the shell 422 of the link 302. For example, the shell 422 can be suspended over the structural link 424 via the contact sensors 408.

In some embodiments, the contact sensors 408 are distributed uniformly along the length of the link 302. In some embodiments, the contact sensors 408 can be distributed randomly along the length of the link 302. Alternatively, in some embodiments, a higher number of sensors 408 may be located in particular areas of the link 302 (e.g., in areas that are known to have more contact with external objects, such as the areas 410 in FIG. 24C and the areas 412 in FIG. 24D). In some embodiments, regardless of the distribution of the sensors 408, because the shell 422 surrounds the structural link 424, when the link 302 contacts an external object, the object will come into contact with the shell 422. Thus, the force- and/or moment-sensing contact sensors 408 can detect contact between the shell 422 and the external object. The sensors 408 can also measure changes in the force and/or torque in all directions between the shell 422 and the structural link 504 that are caused by the link 302 coming into contact with an external object.

In some embodiments, one or more traditional load cells, force sensing resistors, and/or any component capable of sensing force, moment, and/or displacement (e.g., when combined with a spring) may be used instead of (or in addition to) the contact sensors 408, for detecting interactions with an external object.

As used herein, the shell 422 and shell cover 434 may collectively be referred to simply as the "shell" 422, while the structural link 424 and structural cover 426 may collectively be referred to simply as the structural link 424 or a manipulatable link (e.g., the link 302), unless the context clearly indicates otherwise.

Figure 24F:
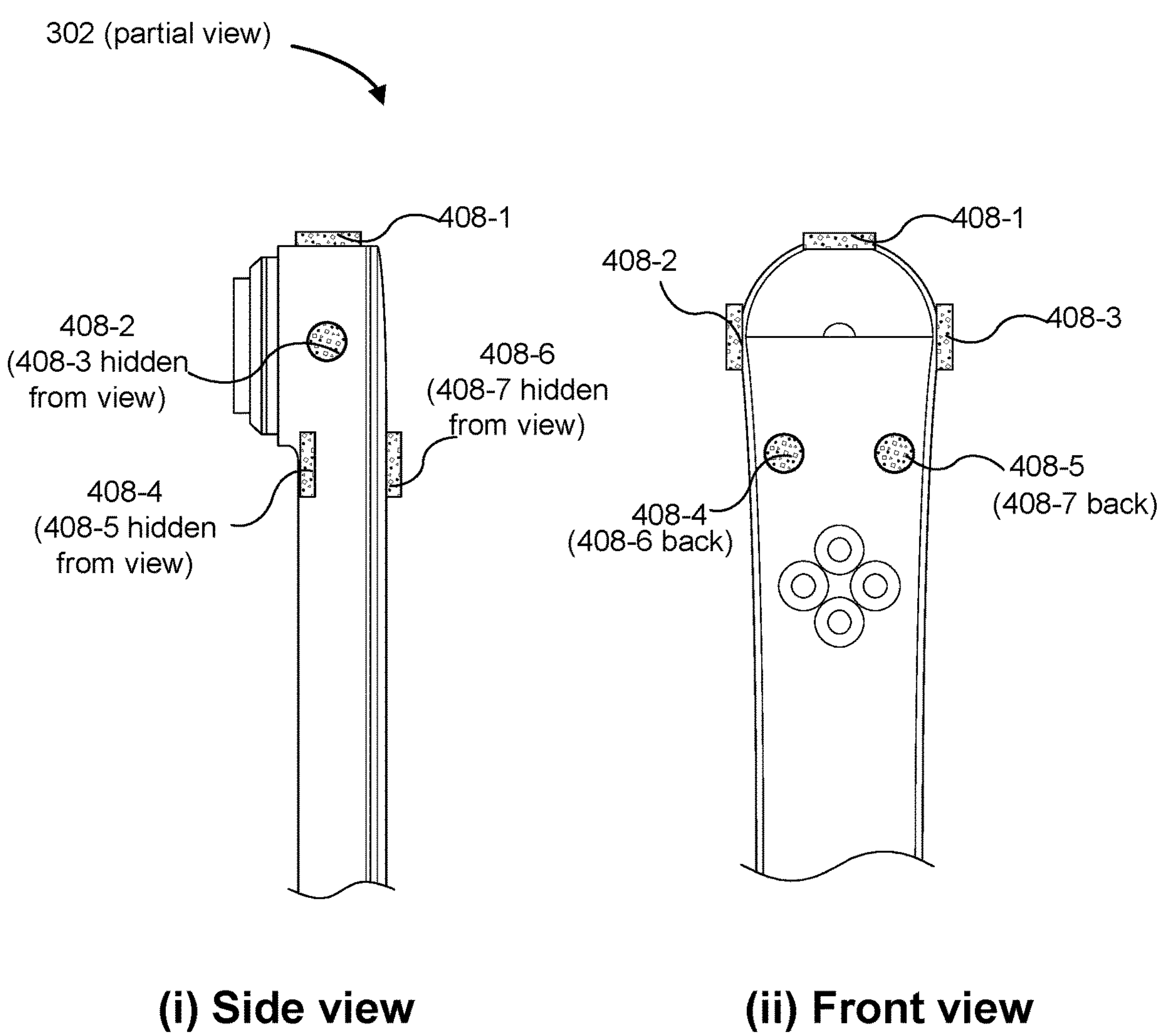
Figure 24G:
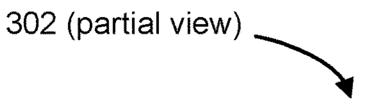
Figure 24G:
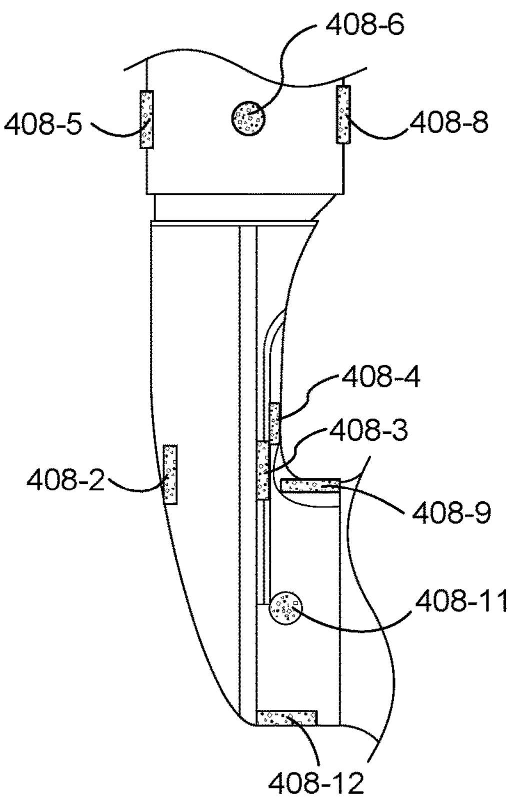
Figure 24G:
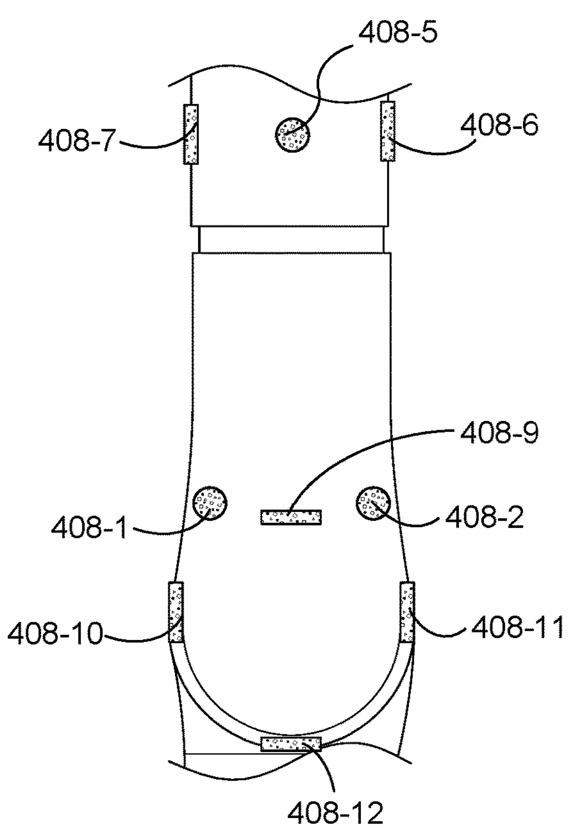

FIGS. 24F and 24G illustrate sensor distributions along a link 302 of a robotic arm 210 according to some embodiments.

FIGS. 24F(i) and 24F(ii) show, respectively, an exemplary side view and a front view of a one end of a link 302 according to some embodiments. In some embodiments, the link 302 corresponds to a proximal link of the robotic arm 210 (e.g., link 302-2 in FIGS. 23A and 23B). In this example, the one end of the link 302 includes seven contact sensors (e.g., 408-1 to 408-7). In some embodiments, because the link 302 (e.g., the link 302-2) may be substantially symmetric at both ends, therefore there are a total of fourteen sensors 408 in the link 302.

FIGS. 24G(i) and 24G(ii) show, respectively, an exemplary side view and a front view of a link 302 according to some embodiments. In some embodiments, the link 302 corresponds to a distal link of the robotic arm 210 (e.g., the link 302-3 in FIGS. 23A and 23B). In this example, twelve contact sensors 408 are included in the link 302, in accordance with some embodiments.

In FIGS. 24F and 24G, the sensors 408 are oriented in different directions, in accordance with some embodiments. In some embodiments, each of the sensors 408 is an individual force sensor (e.g., a single axis force sensor) and the robotic system 200 combine all the sensors to output a lumped (e.g., combined or aggregated) force and/or moment value. Thus, by positioning the sensors in the various orientations as illustrated in FIGS. 24F and 24G, forces and/or moments in all directions can be detected, in accordance with some embodiments.

Although FIGS. 24F and 24G illustrate embodiments of a link 302 that each include a plurality of contact sensors 408, in some embodiments, a link 302 can include a single sensor configured to sense force and/or torque and/or displacement between the structural link 424 and the shell 422 in multiple directions. In some embodiments, using signals received from the sensor(s) 408, the robotic system 200 can detect a direction of the contact between the shell 422 and the external object. The robotic system 200 can also measure a magnitude of a force resulting from the contact between the shell 422 and the external object based on the signal from the sensor(s) 408, in accordance with some embodiments. Based on the placement of the sensors 408, the robotic system 200 can also detect a torque (e.g., a moment) applied to the link 302, in accordance with some embodiments. For example, if a force is applied to the shell 422, certain contact sensors 408 (e.g., on one end of the link 302-2 or the link 302-3) may be compressed, in accordance with some embodiments. Based on the positions of and forces sensed by the sensors 408 being compressed, the robotic system 200 can determine a torque applied to the link 302, in accordance with some embodiments.

FIGS. 24H(i) and 24H(ii) illustrate a robotic arm 210 that includes one or more contact sensing shrouds 436 (e.g., represented by the shaded regions) according to some embodiments. FIG. 24H(i) shows a contact sensing shroud 436-1 on a proximal link of the robotic arm 210 (e.g., link 302-2 in FIGS. 23A and 23B) and a contact sensing shroud 436-2 on a distal link (e.g., link 302-3 in FIGS. 23A and 23B) of the robotic arm 210. Each of the proximal and distal links includes contact sensor(s) 408. FIG. 24H(ii) shows a contact sensing shroud 436-3 on a distal end of the robotic arm, in accordance with some embodiments. A six-axis load cell 404 can also be provided on a distal portion of the robotic arm. FIG. 24H(ii) also shows a remote center motion (RCM) 438. The RCM 438 is a point of intersection of a cannula and a patient's body, in accordance with some embodiments.

In some embodiments, for each sensing shroud on either the distal link or the proximal link of the robotic arm (e.g., the sensing shrouds 436-1 and 436-2), a combined external contact force measurement (e.g., Fc) (e.g., a linear force measurement) and a combined external torque (e.g., moment) measurement (e.g., Mc) acting on any point (e.g., a centroid of the link, a centroid of the robotic arm, a base, a joint, a position on a link, and/or a remote center position) of the robotic arm 210 can be determined (e.g., using the contact sensors 408 and/or any other types of sensors that are capable of detecting force and/or moment).

In some embodiments, the robotic system 200 uses only the force measurement (e.g., Fc), and not the torque measurement (e.g., Mc), to determine whether the robotic system 200 should respond so that the contact force and/or torque does not go beyond the safe force and/or torque limit. The robotic system 200 uses both the force measurement (e.g., Fc) and the torque measurement (e.g., Mc) to determine a direction of movement of the robotic arm 210, in accordance with some embodiments.

In some embodiments, the robotic system 200 uses only the torque measurement (e.g., Mc), and not the force measurement (e.g., Fc), to determine whether the robotic system 200 should take any action. The robotic system 200 uses the torque measurement (e.g., Mc) and/or the force measurement (e.g., Fc) to determine a direction of movement of the robotic arm 210, in accordance with some embodiments.

In some embodiments, the robotic system 200 uses both the force measurement (e.g., Fc) and the torque measurement (e.g., Mc) to determine whether the robotic system 200 should respond. The robotic system 200 also uses the force measurement (e.g., Fc) and/or the torque measurement (e.g., Mc) to determine a direction of movement of the robotic arm 210, in accordance with some embodiments.

In some embodiments, for any external contact force (e.g., F) with the distal end of the robotic manipulator (e.g., the area denoted by the contact sensing shroud 436-3 in FIG. 26H(ii)), it can be shown that the force F is guaranteed to be smaller than a force limit $F_{limit}$ if the induced torque (e.g., $\tau_{RCM}$) at the RCM 438 is smaller than some torque limit $\tau_{limit}$. In some embodiments, the induced torque (e.g., $\tau_{RCM}$) is detected by the six-axis load cell 404, or any other sensors located at or proximate to the distal end. Therefore, by monitoring the induced torque $\tau_{RCM}$ at the RCM 438, the contact force on the distal end of the robotic manipulator can be limited, in accordance with some embodiments.

Figure 25A:
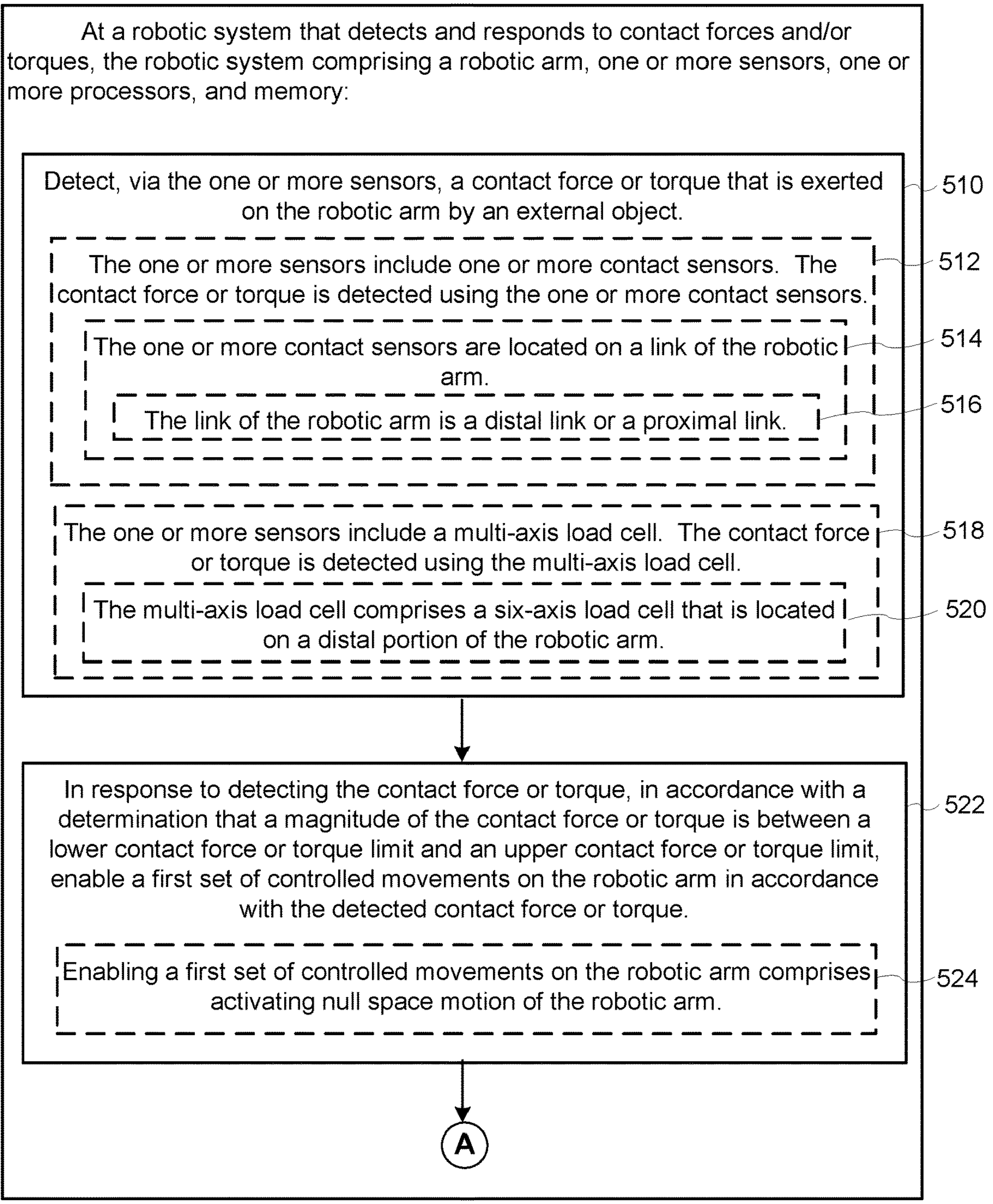
Figure 25C:
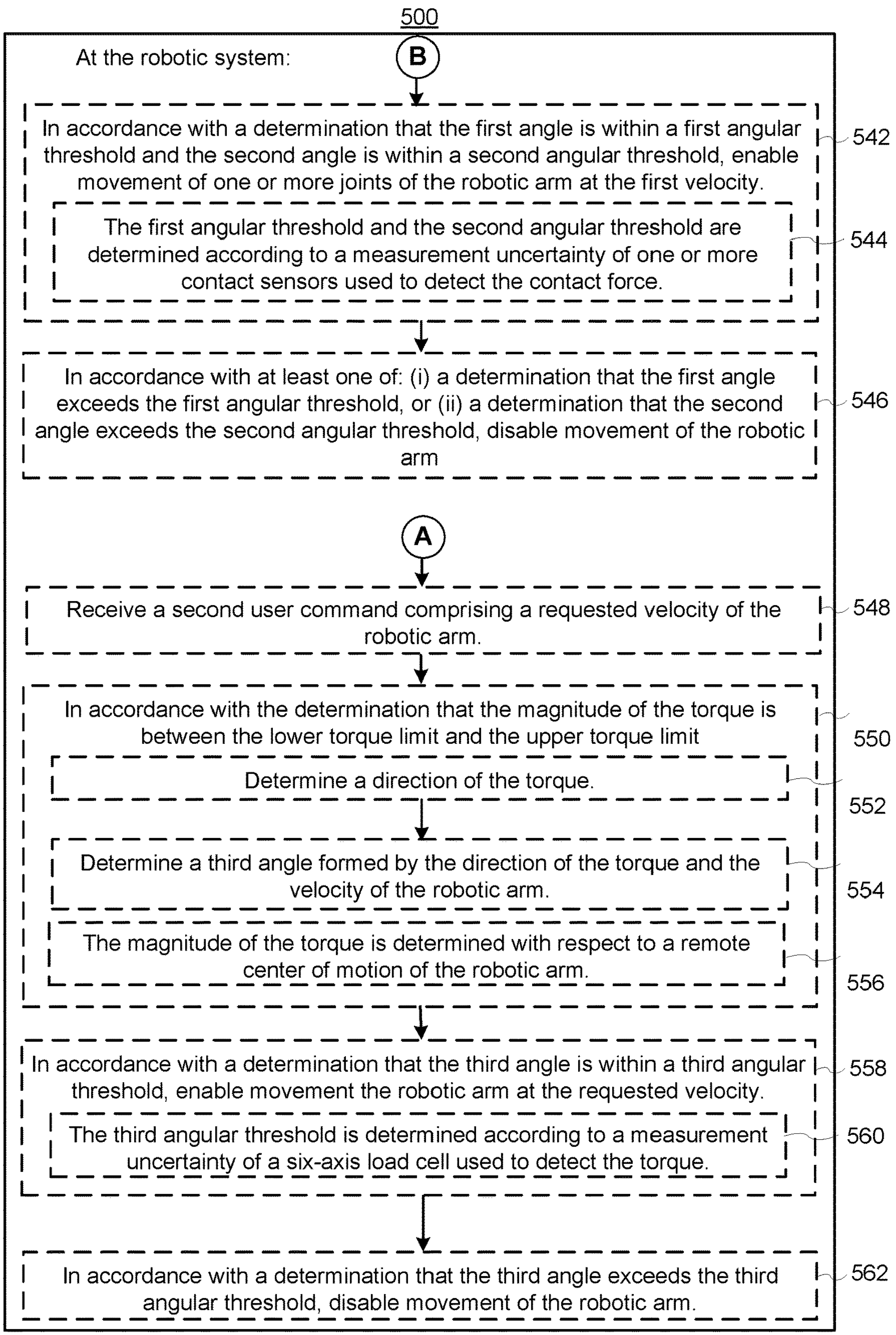

D. Example Methods and Systems of Detecting and Responding to Contact Forces and/or Torques on a Robotic Arm FIGS. 25A to 25C illustrate a flowchart diagram for a method 500 for detecting and responding to contact forces and/or torques according to some embodiments. In accordance with some embodiments of the present disclosure, the method 500 is performed by one or more processors of a robotic system (e.g., the robotic medical system 200 as illustrated in FIGS. 21 and 22, or a robotic surgery platform).

The robotic system includes a robotic arm (e.g., the robotic arm 210 in FIGS. 21, 22, 23A, 23B, 24A, and 24H). In some embodiments, the robotic arm is a first robotic arm of two or more robotic arms of the robotic system (see, e.g., FIGS. 21 and 22).

In some embodiments, the robotic system includes a single robotic arm. The robotic system also includes one or more sensors (e.g., sensors 402 and 404 in FIG. 24A, contact sensors 408 in FIGS. 24B, 24F, and 24G, and/or other sensors described herein).

In some embodiments, the one or more sensors are integrated with (e.g., affixed to, part of, included within, on the surface of, attached to, embedded under the surface of, installed between portions (e.g., between adjacent links, between adjacent joints, etc.) of, installed at the end(s) of, on or within a link of, and/or on or within a joint of, etc.) the robotic arm 210. In some embodiments, the one or more sensors are part of a sensor architecture. In some embodiments, the sensor architecture includes other components for communicating sensor data, e.g., sensor attributes or parameters (e.g., force, contact, moment, displacement, movement, position, etc.) and values (e.g., location, magnitude, timing, duration, etc.) from the sensors to one or more processors of the robotic system.

In some embodiments, the one or more sensors include one or more non-joint based sensors that are located on or within a link (e.g., link 302, FIGS. 23A and 23B) of the robotic arm, between two adjacent joints (e.g., the A4 and A5 joints, two adjacent joints that do not have a link between them, etc.), between a joint and an adjacent end effector, etc. of the robotic arm, or on a portion of the robotic arm that is not a joint of the robotic arm. In some embodiments, the non-joint based sensors include one or more force sensors, one or more moment sensors, and/or one or more force and moment sensors.

In some embodiments, the one or more sensors include one or more joint-based sensors. For example, a joint-based sensor may be located on a proximal end of the robotic arm (e.g., near a base of the robotic arm) (e.g., the A0 joint sensor 402), or on a joint between two adjacent links (e.g., a sensor in the A3 joint 304-4 between two adjacent links 302-2 and 302-3). In some embodiments, the joint-based sensor is a force sensor, a moment sensor, or a combined force and moment sensor.

Referring back to FIG. 25A, the robotic system (e.g., using the one or more processors) detects (510) (e.g., senses and measures), via the one or more sensors, a contact force (e.g., Fc or F) or torque (e.g., Mc or $\tau_{rcm}$) (e.g., an induced torque) that is exerted on the robotic arm by an external object. In some embodiments, the contact force (e.g., Fc or F) and the torque (e.g., Mc or $\tau_{rcm}$) are detected via a sensing shroud 436 on the robotic arm 210 (e.g., the sensing shrouds 436-1, 436-2 and/or 436-3 in FIG. 24H). For example, the contact force or torque may be any force or moment other than that caused by gravity. The contact force or torque may be in at least one direction, in accordance with some embodiments.

In some embodiments, the one or more sensors include (512) one or more contact sensors (e.g., contact sensors 408, FIG. 24B). The contact force (e.g., Fc) or torque (e.g., moment) (e.g., Mc) is detected (e.g., sensed and measured) using the one or more contact sensors 408, in accordance with some embodiments.

In some embodiments, the one or more contact sensors 408 are located (514) on a link of the robotic arm. For example, the contact sensors 408 may be positioned on regions of the robotic arm that are known to regularly collide with a patient during surgery, such as regions 410 in FIG. 24C and regions 412 in FIG. 24D, in accordance with some embodiments. In some embodiments, and as illustrated in FIG. 24E, the contact sensors can have a suspended "shell" around an outside of a robotic arm link 302 (e.g., a proximal link or a distal link). In some embodiments, the contact sensors are force sensors that can sense forces in multiple directions. In some embodiments, the contact sensors are force and moment sensors that can sense forces and moments in multiple directions.

In some embodiments, the link of the robotic arm is (516) a distal link (e.g., distal link 302-3, FIG. 24B) or a proximal link (e.g., proximal link 302-2, FIG. 24A).

In some embodiments, the one or more sensors include (518) a multi-axis load cell. The contact force (e.g., F) or torque (e.g., $\tau_{RCM}$) is detected (e.g., sensed and measured) using the multi-axis load cell.

In some embodiments, the multi-axis load cell includes (520) a six-axis load cell (e.g., six-axis load cell 404, FIG. 24A) that is located on a distal portion of the robotic arm. For example, in FIG. 24A, the six-axis load cell 404 is located on a distal portion of the robotic arm 210, between the A4 joint 304-5 (e.g., a wrist roll joint) and the A5 joint 304-6 (e.g., a wrist pitch joint).

In some embodiments, in response (522) to detecting the contact force or torque, in accordance with a determination that a magnitude of the contact force or torque is between a lower contact force (e.g., Fr) or torque limit (e.g., $\tau_r$) and an upper contact force (e.g., $F_{limit}$) or torque limit (e.g., $\tau_{limit}$), the robotic system enables a first set of controlled movements on the robotic arm in accordance with the detected contact force or torque. For example, the one or more processors may enable the first set of controlled movements on the robotic arm in accordance with the location, direction, magnitude, rate of change in direction and/or magnitude of the detected contact force or torque.

In some embodiments, the magnitude of the contact force or torque may comprise a currently detected value of the contact force or torque, or an average value of the contact force or torque across a preset time window and/or at a preset region of the robotic arm. In some embodiments, the magnitude of the contact force or torque may comprise an aggregated value of the contact force or torque across a preset time window or across a preset region of the robotic arm.

In some embodiments, the lower contact force Fr or the lower torque limit $\tau_r$ comprises a first threshold level of force or torque at which the robotic arm starts to move in reaction to the detected force (e.g., Fc or F) or torque (e.g., Mc or $\tau_{rcm}$). In some embodiments, the lower contact force or torque limit is also referred to as the reaction force or torque limit. For example, the lower contact force limit (e.g., Fr) may be any value between 15 N (e.g., Newtons) and 25 N. The lower torque limit $\tau_r$ may be any value from 2 Nm to 4 Nm.

In some embodiments, the upper contact force $F_{limit}$ or torque limit $\tau_{limit}$ is a second threshold level of force or torque beyond which it may be unsafe or undesirable to move the robotic arm in response to the detected force or torque. In some embodiments, the upper contact force or torque limit is also referred to as the safety force or torque limit. For example, the upper contact force $F_{limit}$ may be any value from 45 N to 60 N, in accordance with some embodiments. The upper torque limit $\tau_{limit}$ may be any value from 7 Nm to 9 Nm, in accordance with some embodiments.

In some embodiments, the contact force or torque is determined to be between the lower contact force or torque limit and the upper contact force or torque limit when its value is equal to the lower contact force limit or the upper contact force limit.

In some embodiments, for any external contact force (e.g., F) with the distal end of the robotic arm 210 (e.g., denoted by the shroud 436-3 in FIG. 24H), the contact force is guaranteed to be smaller than a force limit $F_{limit}$ if the induced torque $\tau_{rcm}$ at the remote center motion is smaller than some torque limit $T_{limit}$. Therefore, by monitoring $\tau_{rcm}$, one can limit the magnitude of the contact force on the distal end of the robotic arm 210, in accordance with some embodiments.

In some embodiments, enabling the first set of controlled movements on the robotic arm includes moving one or more joints (e.g., joints 304, FIGS. 23A and 23B) and/or links (e.g., links 302, FIGS. 23A and 23B) of the robotic arm. The one or more joints and/or links may be selected in accordance with the location, direction, magnitude, and/or rate of change of the detected contact force or torque. Enabling the first set of controlled movements may also include moving one or more joints and/or links of the robotic arm with speeds, directions, etc. that are selected in accordance with the location, magnitude, direction, and/or rate of change of the detected contact force or torque, in accordance with some embodiments.

In some embodiments, enabling the first set of controlled movements on the robotic arm includes executing movement of the robotic arm in accordance with a user's command via a preset control mechanism (e.g., a teleoperation, button control, etc.). For example, a user's command may be a surgeon's command to move a robotic arm (e.g., a link and/or joint of the robotic arm) during teleoperation, in accordance with some embodiments.

In some embodiments, enabling the first set of controlled movements on the robotic arm includes executing (e.g., automatically and without user intervention) null space movement of the robotic arm. For example, the one or more processors can execute null space motion to maintain a position and/or orientation of the cannula. In some embodiments, the null space movement of the robotic arm may be executed in addition to movements of the robotic arm requested by a user via a preset control mechanism.

In some embodiments, enabling the first set of controlled movements on the robotic arm includes executing movement(s) that reduce the detected contact force Fc or torque Tran on the robotic arm (e.g., to ensure that the robotic arm continues to operate within the safe limits).

In some embodiments, the robotic system, while enabling the first set of controlled movements on the robotic arm, restricts a second set of controlled movements on the robotic arm, distinct from the first set of controlled movements. In some embodiments, the first set of controlled movements and the second set of controlled movements collectively constitute a full set of controlled movements that are implemented or supported by the robotic system on the robotic arm. For example, the full set of controlled movements may include different combinations of translation and/or rotation of various joints and links of the robotic arm in the physical environment, in accordance with some embodiments.

In some embodiments, restricting the second set of controlled movements on the robotic arm includes restricting one or more directions of movement, one or more angular ranges of movement, and/or one or more ranges of velocities of movement, etc. of the robotic arm. For example, the robotic system (e.g., through the one or more processors) may restrict some form of controlled movement on the robotic arm, including restricting a respective direction of movement, a respective angle of movement, and/or a respective velocity etc., of one or more joints and/or one or more links of the robotic arm.

In some embodiments, when the detected contact force or torque is between a lower contact force or torque limit and an upper contact force or torque limit, the robotic system permits controlled movements but imposes some restriction on the controlled movements of the robotic arm. For example, the robotic system may modify the direction and/or speed of the movement of the robotic arm that is requested by the user, to reduce the contact force or torque, in accordance with some embodiments. Accordingly, the robotic system provides feedback to the user without interrupting or completely prohibiting the movements requested by the user, in accordance with some embodiments. In some embodiments, when the detected contact force or torque is approaching the upper contact force or torque limit, the robotic system provides stronger feedback (e.g., haptic or visual) to the user by actively adjusting the movement speed and direction of the movement of the robotic arm in accordance with the characteristic values of the detected contact force and/or torque.

Referring back to FIG. 25, in some embodiments, enabling (524) a first set of controlled movements on the robotic arm comprises activating null space motion of the robotic arm. For example, in some circumstances, the contact force may come from contact between the robotic arm and a patient during surgery. In some embodiments, the robotic system may automatically (e.g., without user intervention) activate null space motion of the robotic arm to reduce the contact force exerted against the patient by the robotic arm, without interrupting the surgery.

In some embodiments, in response (526) to detecting the contact force or torque, in accordance with a determination that the contact force or torque exceeds the upper contact force or torque limit, the robotic system (e.g., through the one or more processors) disables movement of a part of the robotic system. For example, the one or more processors may disable motion of all joints and/or links of the robotic arm that were previously started, in accordance with some embodiments. The one or more processors may also prevent the movements from starting or continuing in response to user commands, and in response to the detected contact force or torque on the robotic arm, in accordance with some embodiments. In some embodiments, the one or more processors may also disable movement of the table top or adjustable arm supports of the robotic system, in accordance with some embodiments.

In some embodiments, in response (528) to detecting the contact force or torque, in accordance with a determination that the contact force or torque is less than the lower contact force or torque, the robotic system forgoes enabling the first set of controlled movements on the robotic arm in accordance with the detected contact force or torque. For example, if the contact force or torque is very low, the robotic system will not activate movement to reduce contact force or torque, in accordance with some embodiments. The robotic arm may be stationary or may be controlled normally via other active control mechanisms, in accordance with some embodiments. For example, a user can control the robotic arm as the user typically would during surgery, such as via teleoperation, button control, and/or impedance mode control. In some embodiments, in response to detecting the contact force or torque, and in accordance with a determination that the contact force or torque is less than the lower contact force or torque, the robotic system also forgoes restricting the second set of controlled movements on the robotic arm.

In some embodiments, the robotic system receives (530) a first user command comprising a first velocity (e.g., $\dot{x}_{req}$) of the robotic arm. In some embodiments, the first velocity (e.g., $\dot{x}_{req}$) includes a first direction of motion of the robotic arm and/or a first magnitude of movement (e.g., speed) of the robotic arm. For example, the first velocity of the robotic arm may be the velocity of an end effector (e.g., ADM 308, FIG. 23A) of the robotic arm. In some embodiments, the first user command is a velocity command in the form of Cartesian coordinates. After receiving the first user command, the robotic system calculates the necessary (e.g., corresponding) joint speed that matches the first user command, in accordance with some embodiments.

In some embodiments, in accordance with (532) the determination that the magnitude of the contact force (e.g., $\|Fc\|$) (e.g., measured by the contact sensors on the link of the robotic arm) is between a lower contact force limit (e.g., Fr) and an upper contact force limit (e.g., $F_{limit}$), the robotic system (a) determines (534) a direction of the contact force (e.g., $\theta_F$); (b) determines (536) a direction of the torque (e.g. $\theta_\omega$); (c) determines (538) a first angle formed by a translational velocity of the robotic arm (e.g., the translational velocity of the robotic arm link where contact occurs) and the direction of the contact force; and (d) determines (540) a second angle formed by a rotational velocity of the robotic arm and the direction of the torque.

For example, in some embodiments, the first angle formed by the translational velocity of the robotic arm and the direction of the contact force can be represented by:

$$\theta_1 = \cos^{-1}\frac{V_C \cdot Fc}{\|V_C\|\,\|F_C\|} \tag{1}$$

wherein $V_C$ is the translational velocity vector of the robotic arm (e.g., a link of the robotic arm) with respect to its centroid (or any other position of the robotic arm) $F_C$ is the contact force vector, $\|V_C\|$ is the norm (e.g., magnitude) of the vector $V_C$, and $\|F_C\|$ is the norm (e.g., magnitude) of the vector $F_C$, in accordance with some embodiments.

The second angle formed by the rotational velocity of the robotic arm and the direction of the torque can be represented by:

$$\theta_2 = \cos^{-1}\frac{\omega_C \cdot M_C}{\|\omega_C\|\,\|M_C\|} \tag{2}$$

wherein $\omega_C$ is the rotational velocity vector of the robotic arm (e.g., rotational velocity of a link of the robotic arm) with respect to its centroid (or any other position of the robotic arm), $M_C$ is the torque vector (e.g., detected by the contact sensors 408) with respect to a centroid of a link (or any other position of the robotic arm), $\|\omega_C\|$ is the norm (e.g., magnitude) of the vector $\omega_C$, and $\|M_C\|$ is the norm (e.g., magnitude) of the vector $M_C$.

$$\begin{bmatrix} V_C \\ \omega_C \end{bmatrix} = J_c(q)\dot{q}_{req},$$

where $J_C(q)$ is the Jacobian of link centroid, in accordance with some embodiments.

With continued reference to FIG. 25, in some embodiments, in accordance with (542) a determination that the first angle is within (e.g., less than or equal to, does not exceed) a first angular threshold (e.g., $\theta_1 \leq \theta_{limit,f}$) and the second angle is within (e.g., less than or equal to, does not exceed) a second angular threshold (e.g., $\theta_2 \leq \theta_{limit,\omega}$), the robotic system enables movement of the joint of the robotic arm (e.g., $\dot{q}_{cmd}$) at the first velocity (e.g., $\dot{q}_{req}$)

In some embodiments, the first angular threshold (e.g., $\theta_{limit,f}$) and the second angular threshold (e.g., $\theta_{limit,\omega}$) are (544) determined according to a measurement uncertainty of one or more contact sensors (e.g., contact sensors 408, FIG. 24B) used to detect the contact force. For example, the contact sensors 408 may be located in the regions indicated by the sensing shroud 436-1 or the sensing shroud 436-2 in FIG. 24H(i), in accordance with some embodiments.

In some embodiments, in accordance with (546) at least one of: (i) a determination that the first angle exceeds the first angular threshold (e.g., $\theta_1 > \theta_{limit,f}$), or (ii) a determination that the second angle exceeds the second angular threshold (e.g., $\theta_2$>θlimit,ω), the robotic system disables movement of the robotic arm (e.g., $\dot{q}_{cmd}=0$).

Figure 26:
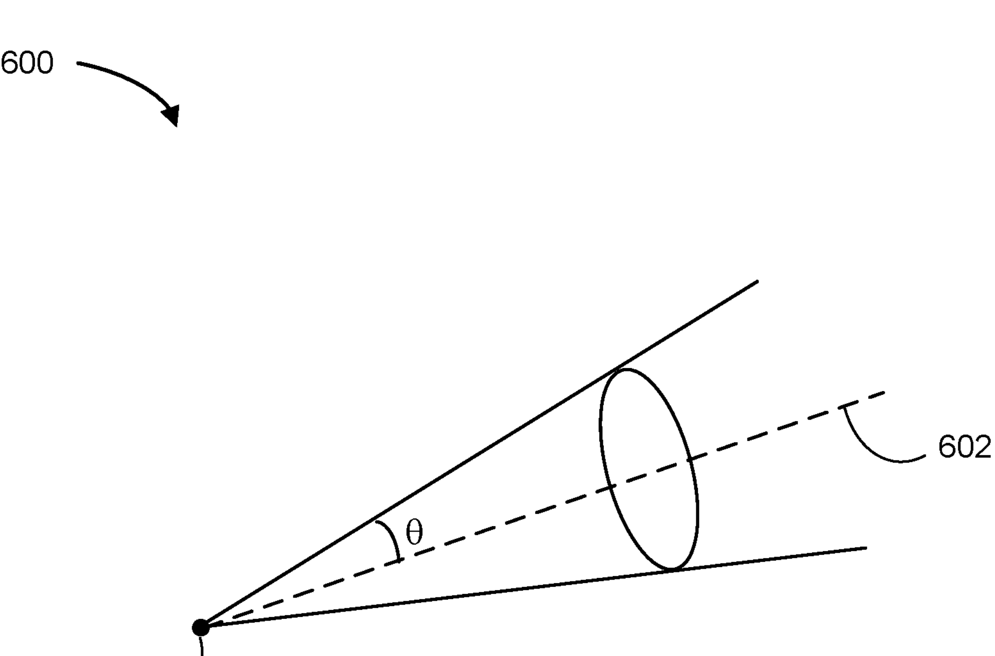
FIG. 26 illustrates allowed movements of a robotic arm in space.

In some embodiments, the allowed movements of the robotic arm in space can be represented by a cone 600 (e.g., an angular range), as illustrated in FIG. 26. The cone 600 comprises an axis 602, which represents the direction of the contact force (e.g., Fc) or moment (e.g., Mc). The cone 600 also includes an apex 604 that is representative of the collision point of the contact, while the volume in the cone represents the neighborhood of allowed next movement of the robotic arm in three-dimensional space. As the robotic arm reacts and moves away from the previous collision point, the contact force Fc is expected to reduce, in accordance with some embodiments. In some embodiments, if Fc is still above the reaction force limit Fr, a new cone, determined by the new contact condition, defines the new allowed movement. In some embodiments, a representative value for $F_{limit}$ can be 110 N. In some embodiments, the reaction force limit Fr for such reaction behavior can be set (e.g., predefined) at 80 N.

In some embodiments, the robotic system receives (548) a second controlled command comprising a requested velocity of the robotic arm (e.g., a requested angular velocity, $\omega_{req}$) For example, the requested velocity of the robotic arm may comprise a requested angular velocity of a link of the robotic arm (e.g., link 302) or a requested angular velocity of a joint (e.g., 304) of the robotic arm, in accordance with some embodiments. In some embodiments, the angular velocity of the robotic arm includes magnitude (e.g., speed) and direction (e.g., the angular velocity of the robotic arm is a vector). In some embodiments, the angular velocity of the robotic arm (e.g., $\omega_{req}$) is an angular velocity that is requested from a surgeon during teleoperation of the robotic arm.

In some embodiments, in accordance with (550) the determination that the magnitude of the contact torque (e.g., $\|\tau_{RCM}\|$) (e.g., contact moment or induced torque) (e.g., measured by the multi-axis load cell(s) on the between links or on the distal ends of the robotic arm, such as the six-axis load cell 404 in FIG. 24A and FIG. 24H(ii)) is between the lower reaction torque limit (e.g., $\tau_R$) and the upper torque limit (e.g., $\tau_{limit}$), the robotic system determines (552) a direction of the torque. The robotic system also determines (554) a third angle formed by the direction of the torque and the angular velocity of the robotic arm, in accordance with some embodiments.

In some embodiments, the lower reaction torque limit (e.g., $\tau_R$) is the minimum measured torque required at the RCM (e.g., RCM 438) for the robotic arm to react to the contact.

In some embodiments, the third angle formed by the direction of the torque and the angular velocity of the robotic arm can be represented by:

$$\theta_3 = \cos^{-1}\frac{\omega_{req} \cdot \tau_{RCM}}{\|\omega_{req}\|\,\|\tau_{RCM}\|} \tag{3}$$

wherein $\omega_{req}$ is the angular velocity vector of the robotic arm, $\tau_{RCM}$ is the torque vector that is measured by the six-axis load cell, $\|\omega_{req}\|$ is the norm (e.g., magnitude) of the torque vector $\omega_{req}$, and $\|\tau_{RCM}\|$ is the norm (e.g., magnitude) of the torque vector $\tau_{RCM}$.

In some embodiments, the magnitude of the torque is (556) determined with respect to a remote center of motion of the robotic arm (e.g., RCM 438, FIG. 24H(ii)).

In some embodiments, in accordance with a determination that the third angle is within (e.g., less than or equal to, does not exceed) a third angular threshold (e.g., 03 the robotic system enables (558) movement of the robotic arm at the requested velocity (e.g., the requested angular velocity, $\omega_{req}$).

In some embodiments, the third angular threshold is (560) determined according to a measurement uncertainty of a six-axis load cell (e.g., six axis load cell 404) used to detect the torque.

In some embodiments, in accordance with (562) a determination that the third angle exceeds the third angular threshold (e.g., $\theta_3 > \theta_{limit}$), the robotic system disables movement of the robotic arm.

Figure 27A:
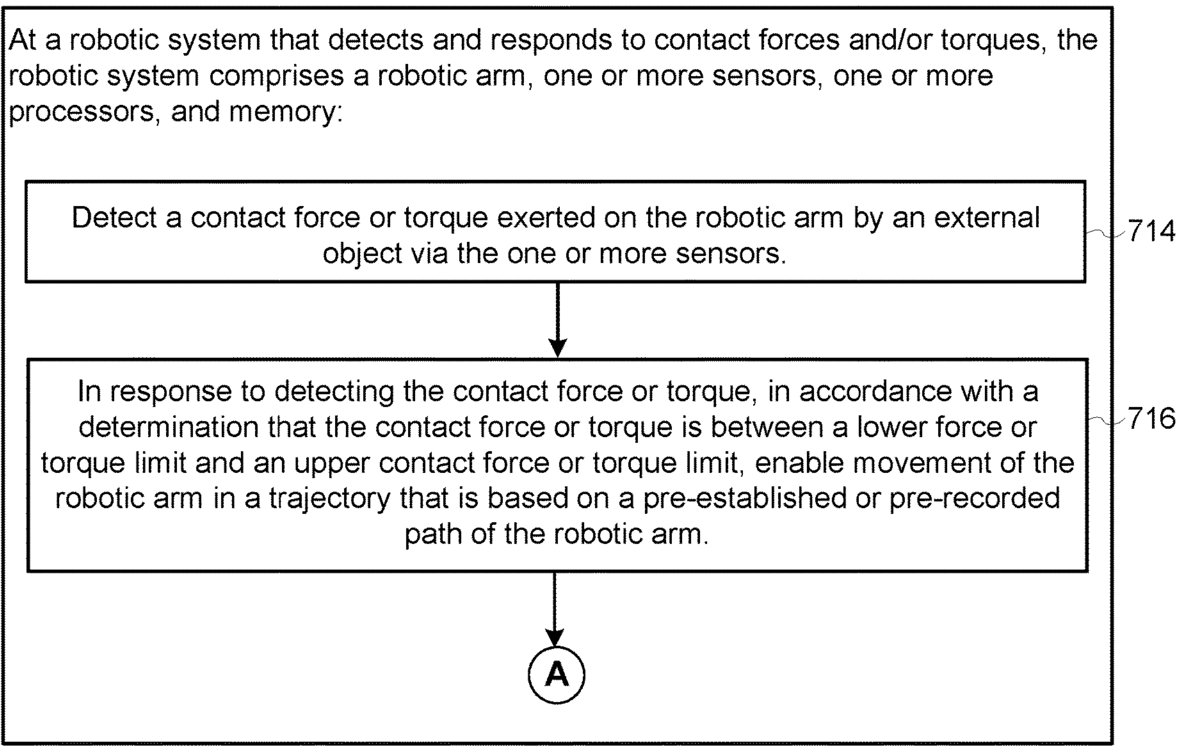

FIGS. 27A to 27B are a flowchart diagram for a method 700 for detecting and responding to contact forces and/or torques according to some embodiments. In some embodiments, the method 700 is performed by one or more processors of a robotic system (e.g., the robotic medical system 200 as illustrated in FIGS. 21 and 22, or a robotic surgery platform).

The robotic system includes a robotic arm (e.g., the robotic arm 210 in FIGS. 21, 22, 23A, 23B, 24A, and 24H). The robotic system also includes one or more sensors (e.g., sensors 402 and 404 in FIG. 24A, contact sensors 408 in FIGS. 24B, 24F, and 24G, and/or other sensors described herein). In some embodiments, the one or more sensors include one or more contact sensors (e.g., contact sensors 408). In some embodiments, the one or more sensors include a six-axis load cell (e.g., six-axis load cell 404, FIG. 24A and FIG. 24H). The robotic system also includes one or more processors and memory. The memory stores instructions that are executed by the one or more processors.

In accordance with some embodiments of the present disclosure, the robotic system detects (714) a contact force (e.g., Fc or F) or torque (e.g., $M_C$ or $\tau_{rcm}$) exerted on the robotic arm by an external object via the one or more sensors.

In some embodiments, in response (716) to detecting the contact force or torque, in accordance with a determination that the contact force or torque (e.g., a magnitude of the contact force or torque) is between a lower force (e.g., Fr) or torque limit (e.g., $\tau_r$) and an upper contact force (e.g., $F_{limit}$) or torque limit (e.g., $\tau_{limit}$), the robotic system enables movement of the robotic arm in a trajectory that is based on a pre-established or pre-recorded path of the robotic arm.

In some embodiments, the trajectory corresponds to a reversal of a previous movement path executed prior to the detection of the force or torque.

In some embodiments, the contact force or torque is determined to be between the lower contact force or torque limit and the upper contact force or torque limit when its value is equal to the lower contact force limit or the upper contact force limit.

In some embodiments, the pre-established or pre-recorded path of the robotic arm comprises (718) a pre-recorded path of a link centroid of the robotic arm. In some embodiments, the pre-established or pre-recorded path of the robotic arm comprises a pre-recorded path of a joint of the robotic arm, or joint values of a plurality of joints of the robotic arm.

In some embodiments, the robotic system determines (720), from the pre-recorded path of the link centroid, a translational (e.g., $D_t$) and rotational motion direction (e.g., $D_r$) along the pre-recorded path over a configurable period. For example, the configurable period can be any time period (e.g., time duration) from 10 seconds to 100 seconds. In some embodiments, at each time instance (e.g., every second, every 2 seconds, etc.) of the configurable period, a respective transitional and rotational motion direction can be determined based on the recorded path.

In some embodiments, the robotic system receives a user command comprising a first velocity (e.g., $\dot{x}_{req}$). In some embodiments, the first velocity (e.g., $\dot{x}_{req}$) includes a direction of motion of the robotic arm and/or a magnitude of movement (e.g., speed) of the robotic arm. For example, the velocity of the robotic arm may be the velocity of an end effector (e.g., ADM 308, FIG. 23A) of the robotic arm. In some embodiments, in accordance with the determination that the magnitude of the contact force (e.g., measured by the contact sensors on the link of the robotic arm) is between the lower contact force limit (e.g., Fr) and the upper contact force limit (e.g., $F_{limit}$), the robotic system (a) determines a direction of the contact force (e.g., $\theta_F$); (b) determines a direction of the torque (e.g. $\theta_\omega$); (c) determines a first angle formed by the translational velocity of the robotic arm and the translational motion direction along the pre-recorded path; and (d) determines a second angle formed by the rotational velocity of the robotic arm and the rotational motion direction along the pre-recorded path.

For example, the first angle formed by the translational velocity of the robotic arm and the translational motion direction along the pre-recorded path can be represented by:

$$\theta_1 = \cos^{-1}\frac{V_C \cdot D_t}{\|V_C\|\,\|D_t\|} \tag{4}$$

wherein $V_C$ is the translational velocity vector of the robotic arm, $D_t$ is the translational motion vector of the robotic arm along the pre-recorded path of the link centroid over the configurable period, $\|V_C\|$ is the norm (e.g., magnitude) of the vector $V_C$, and $\|D_t\|$ is the norm (e.g., magnitude) of the vector $D_t$, in accordance with some embodiments.

The second angle formed by the rotational velocity of the robotic arm and the rotational motion direction along the pre-recorded path can be represented by:

$$\theta_2 = \cos^{-1}\frac{\omega_C \cdot D_r}{\|\omega_C\|\,\|D_r\|} \tag{5}$$

wherein $\omega_C$ is the rotational velocity vector of the robotic arm (e.g., of a link of the robotic arm) with respect to its centroid (and/or any other position of the robotic arm), $D_r$ is the rotational motion vector along the pre-recorded path of the link centroid over the configurable period, $\|\omega_C\|$ is the norm (e.g., magnitude) of the vector $\omega_C$, and $\|D_r\|$ is the norm (e.g., magnitude) of the vector $D_r$, in accordance with some embodiments.

In some embodiments, in accordance with a determination that the first angle is within (e.g., less than or equal to, does not exceed) a first angular threshold (e.g., $\theta_1 \leq \theta_1 \theta_{limit,f}$) and the second angle is within (e.g., less than or equal to, does not exceed) a second angular threshold (e.g., $\theta_2 \leq \theta_{limit,\omega}$), the robotic system enables movement of the joint of the robotic arm (e.g., $\dot{q}_{cmd}$) at the prerecorded path at the user commanded velocity.

For example, the robotic system can calculate the first and second angles at each time instance (e.g., every second, every two seconds etc.) of the configurable period to determine whether they are within their respective angular thresholds, and enables movement of the joint of the robotic arm in accordance with a determination that the first and second angles if the first angle is within (e.g., less than or equal to, does not exceed) a first angular threshold (e.g., $\theta_1 \leq \theta_{limit,f}$) and the second angle is within (e.g., less than or equal to, does not exceed) a second angular threshold (e.g., $\theta_2 \leq \theta_{limit,\omega}$) for said time instance, in accordance with some embodiments.

In some embodiments, in accordance with a determination that the first angle exceeds the first angular threshold (e.g., $\theta_1 > \theta_{limit,f}$) and/or the second angle exceeds the second angular threshold (e.g., $\theta_2 > \theta_{limit,\omega}$), the robotic system disables movement of the robotic arm.

Referring again to FIG. 27, in some embodiments, the pre-established or pre-recorded path of the robotic arm comprises (722) a pre-established or pre-recorded path of a pitch and/or yaw angle of a remote center motion of the robotic arm (e.g., RCM 438, FIG. 24H).

In some embodiments, the robotic system also determines (724), from the pre-established or pre-recorded path of the robotic arm (e.g., the pre-recorded path of the pitch/yaw angle of the RCM), an average motion direction (e.g., $\dot{d}$) along the pre-recorded path over a configurable period (e.g., 2 seconds to 100 seconds).

In some embodiments, the robotic system receives a controlled command comprising an angular velocity of the robotic arm (e.g., $\omega_{req}$). The robotic system can determine the magnitude of the torque using the multi-axis load cell(s) on the between links or on the distal ends of the robotic arm, such as the six-axis load cell 404 in FIG. 24A and FIG. 24H(ii). In some embodiments, in accordance with the determination that the magnitude of the detected torque (e.g., $|\tau_{RCM}|$) is between the lower reaction torque limit (e.g., $\tau_R$) and the upper torque limit (e.g., $\tau_{limit}$), the robotic system determines a direction of the torque. The robotic system also determines a third angle formed by the direction of the torque and the angular velocity of the robotic arm.

In some embodiments, the third angle formed by the direction of the torque and the angular velocity of the robotic arm can be represented by:

$$\theta_3 = \cos^{-1}\frac{\omega_{req}\cdot\dot{d}}{\|\omega_{req}\|\,\|\dot{d}\|} \tag{6}$$

wherein $\omega_{req}$ is the angular velocity vector of the robotic arm over the configurable period, $\dot{d}$ is the average motion direction along the pre-recorded path over a configurable period, $\|\omega_{req}\|$ is the norm (e.g., magnitude) of the vector $\omega_{req}$, and $\|\dot{d}\|$ is the norm (e.g., magnitude) of the vector d.

In some embodiments, in accordance with a determination that the third angle is within (e.g., less than or equal to, does not exceed) a third angular threshold (e.g., $\theta_3 \le \theta_{limit}$), the robotic system enables movement the robotic arm at the average motion direction (e.g., $\dot{d}$) along the pre-recorded path.

In some embodiments, in accordance with a determination that the third angle exceeds the third angular threshold, the robotic system disables movement of the robotic arm.

Figure 28:
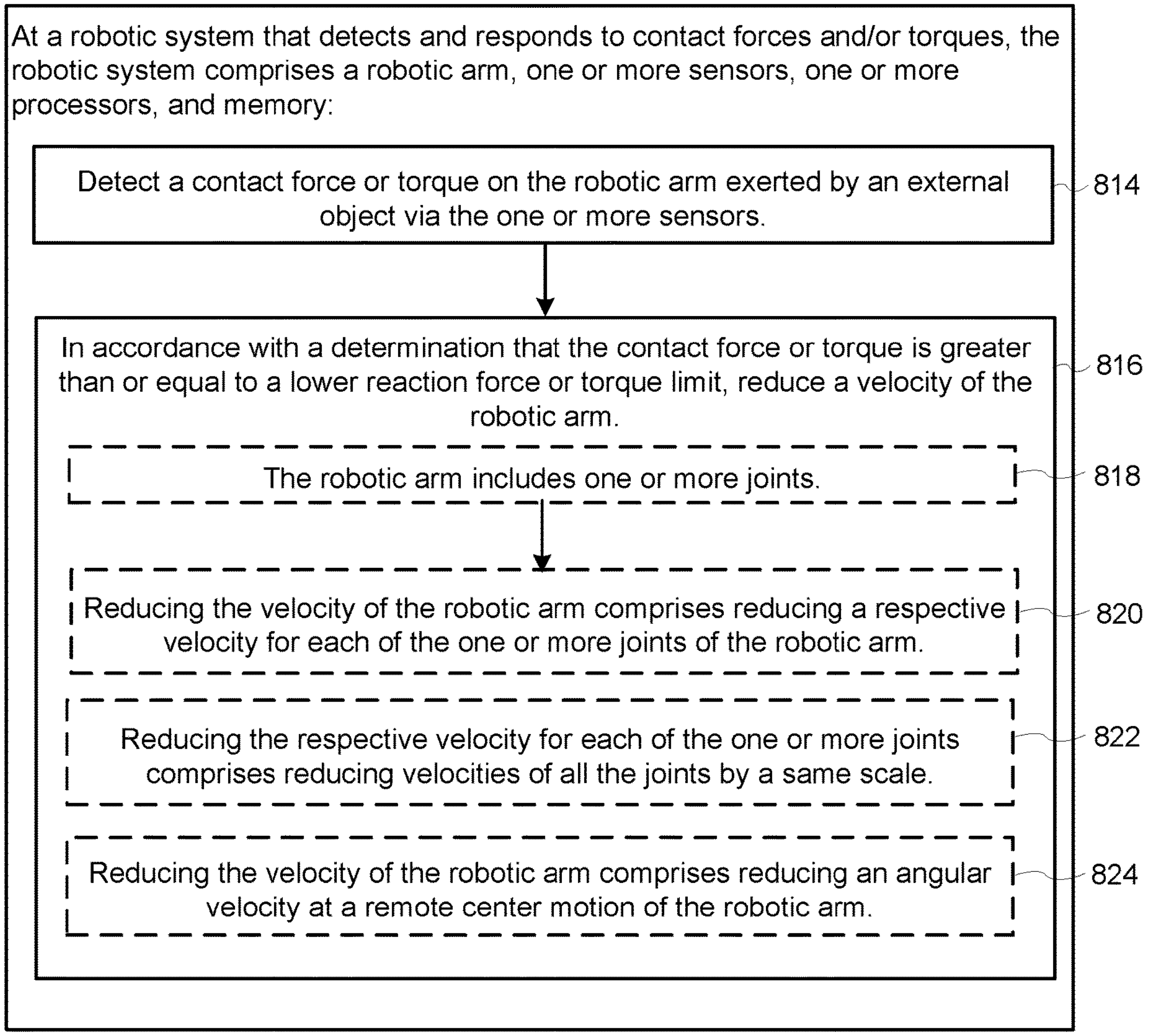
FIG. 28 illustrates a flowchart diagram of another method for detecting and responding to contact forces and/or torques according to some embodiments.

FIG. 28 is a flowchart diagram for a method 800 for detecting and responding to contact forces and/or torques according to some embodiments. In some embodiments, the method 700 is performed by one or more processors of a robotic system (e.g., the robotic medical system 200 as illustrated in FIGS. 21 and 22, or a robotic surgery platform).

The robotic system comprises a robotic arm. (e.g., the robotic arm 210 in FIGS. 21, 22, 23A, 23B, 24A, and 24H). In some embodiments, the robotic arm is a first robotic arm of two or more robotic arms of the robotic system (see, e.g., FIGS. 21 and 22). In some embodiments, the robotic system comprises a single robotic arm.

The robotic system also comprises one or more sensors (e.g., sensors 402 and 404 in FIG. 24A, contact sensors 408 in FIGS. 24B, 24F, and 24G, and/or other sensors described herein).

In some embodiments, the one or more sensors include one or more contact sensors (e.g., contact sensors 408, FIG. 24B). In some embodiments, the contact sensors are force and/or moment sensors that detect force and/or moments (e.g., torque). In some embodiments, the one or more sensors include a six-axis load cell (e.g., six-axis load cell 404).

The robotic system comprises one or more processors and memory. The memory stores instructions that are executed by the one or more processors.

The robotic system detects (814) a contact force (e.g., Fc or F) or torque (e.g., $M_C$ or $\tau_{rcm}$) on the robotic arm exerted by an external object via the one or more sensors. In some embodiments, the contact force (e.g., Fc) and the torque (e.g., $M_C$) are detected via a sensing shroud on a link of the robotic arm 210 (e.g., the sensing shrouds 436-1 and/or 436-2 in FIG. 24H). In some embodiments, the contact force (e.g., F) and the torque (e.g., $\tau_{rcm}$) are detected via a sensing shroud on a distal end of the robotic arm 210 (e.g., the sensing shroud 436-3 in FIG. 24H). For example, the contact force or torque may be any force or moment other than that caused by gravity. The contact force or torque may be in multiple directions.

In some embodiments, in accordance with (816) a determination that the contact force or torque is greater than or equal to a lower reaction force (e.g., Fr) or torque limit (e.g., $\tau_r$), the robotic system reduces a velocity of the robotic arm.

In some embodiments, the robotic arm includes (818) one or more joints. Reducing the velocity of the robotic arm comprises (820) reducing a respective velocity for each of the one or more joints of the robotic arm.

In some embodiments, reducing the respective velocity for each of the one or more joints comprises (822) reducing velocities of all the joints by a same scale (e.g., same proportion. For example, the robotic system may reduce the respective velocity for each of the joints by 1%, 2% 5%, or 10%, etc., in accordance with some embodiments.

In some embodiments, the robotic system receives a first controlled command comprising a first velocity (e.g., $\dot{x}_{req}$) (e.g., a first velocity comprises a velocity of an end effector of the robotic arm). In accordance with a determination that the contact force is less than or equal to the lower reaction force limit (e.g., Fc≤Fr), the robotic system enables movement of the robotic arm at the first velocity. In accordance with a determination that the contact force is greater than a lower reaction force limit (e.g., Fc>Fr), the robotic system enables movement of the robotic arm at a commanded velocity (e.g., $\dot{q}_{cmd}$) that is less than the first velocity, in accordance with some embodiments. For example, the commanded velocity of the robotic arm (e.g., of a joint of the robotic arm) can be represented by:

$$\dot{q}_{cmd}\begin{cases}\dot{x}_{req} & F_c \le F_r \\ \dot{x}_{req}\dfrac{F_{limit}-F_c}{F_{limit}-F_r} & F_c > F_r\end{cases} \tag{7}$$

in accordance with some embodiments.

Equation (7) shows that when the contact force Fc is greater than a lower reaction force limit (e.g., Fc>Fr), the robot joint velocity decreases as the contact force Fc increases. In this equation, $F_{limit}$ is the upper threshold level of force beyond which it may be unsafe or undesirable to move the robotic arm in response to the detected force, in accordance with some embodiments. Since ($F^{limit}$–Fr) is a constant, Equation (7) illustrates that the higher the detected contact force Fc, the lower the commanded velocity $\dot{q}_{cmd}$, in accordance with some embodiments. Furthermore, movement of the robotic arm is not allowed (e.g., disabled or stopped) when the detected contact force Fc is at least as large as $F_{limit}$ (e.g., $\dot{q}_{cmd}=0$ when $F_C \ge F_{limit}$), in accordance with some embodiments. If the contact force Fc is less than or equal to the reaction force limit reaction force limit (e.g., Fc≤Fr), the commanded joint velocity $\dot{q}_{cmd}$ is the same as that requested by a surgeon (e.g., $\dot{q}_{cmd}=\dot{x}_{req}$), in accordance with some embodiments.

In some embodiments, reducing the velocity of the robotic arm includes reducing (824) an angular velocity at a remote center motion (e.g., RCM 438, FIG. 24H) of the robotic arm.

For example, in some embodiments, the robotic system receives a second controlled command comprising a first angular velocity of the robotic arm (e.g., $\omega_{req}$). For example, the angular velocity of the robotic arm may comprise the angular velocity of a link of the robotic arm (e.g., link 302) or the angular velocity of a joint (e.g., 304) of the robotic arm, in accordance with some embodiments. In accordance with a determination that the torque is less than or equal to the lower torque limit (e.g., $\tau_{rcm}\leq\tau_r$), the robotic system enables movement of the robotic arm at the first angular velocity. In accordance with a determination that the torque is greater than a lower torque limit (e.g., $\tau_{rcm}>\tau_r$), the robotic system enables movement of the robotic arm at a commanded angular velocity (e.g., $\omega_{cmd}$) that is less than the first angular velocity $\omega_{req}$. In some embodiments, this scenario can be represented by:

$$\omega_{cmd} = \begin{cases} \omega_{req} & \tau_{rcm} \leq \tau_r \\ \omega_{req}\dfrac{\tau_{limit}-\tau_{rcm}}{\tau_{limit}-\tau_r} & \tau_{rcm} > \tau_r \end{cases} \quad (8)$$

In Equation (8), $\tau_{limit}$ is the upper threshold level of torque beyond which it may be unsafe or undesirable to move the robotic arm in response to the detected torque. Because $(\tau_{limit}-\tau_r)$ is a constant value, Equation (8) illustrates that the higher the detected torque $\tau_{rcm}$, the lower the commanded angular velocity $\omega_{cmd}$, in accordance with some embodiments. Furthermore, movement of the robotic arm is not allowed (e.g., disabled or stopped) when the detected torque $\tau_{rcm}$ is at least as large as $\tau_{limit}$ (e.g., $\omega_{cmd}=0$ when $\tau_{rcm}\geq\tau_{limit}$), in accordance with some embodiments.

In some embodiments, various aspects of the method 500 method 700, or method 800 can be used independently, or combined with respect to one or more of the robotic arms.

D. Unified Null Space Motion Control

As described earlier, a robotic arm (e.g., robotic arm 210) can include a multitude of joints (e.g., joints 304, FIGS. 23A and 23B), which result in a multitude of degrees of freedom (DoF). In some embodiments, a robotic arm can have at least seven joints, thus having seven DoFs. When a robotic arm has seven joints, one of the joints can be considered a redundant joint. Therefore, a robotic arm with at least seven joints has at least one additional DoF (e.g., additional degree of redundancy, or one redundant DoF). In some embodiments, the one or more redundant DoFs can allow the robotic arm to move in a null space to maintain the pose of the ADM 308 and/or a position of an RCM and avoid collision(s) with other robotic arms or objects. In some embodiments, while the robotic arm is moving in null space, the end effector of the robotic arm can be positioned toward a specific pose (e.g., position and/or orientation) and trajectory in space using different linkage positions and joint angles, in accordance with some embodiments. In some embodiments, movement of the end effector of the robotic arm can be via teleoperation, while in other embodiments, movement of the end effector of the robotic arm can be via manual movement or slave clutching of the robotic arm. In some embodiments, the one or more redundant DoFs enable (s) the robotic arm to position and direct a medical instrument from a desired point in space while allowing the physician to move the arm joints into a clinically advantageous position away from the patient to create greater access, while avoiding arm collisions.

In some embodiments, a robotic arm with one DoF redundancy can be commanded into a desired pose while holding its remote center (e.g., during teleoperation). The same robotic arm can concurrently (e.g., simultaneously) be used for several objectives while delivering the arm of the desired pose. The objectives can include kinematic collision (e.g., collision between arms of the robotic system, or between an arm and ground or other system components, such as the adjustable bar, bed top, etc.) avoidance, joint limit avoidance, excessive contact avoidance, admittance null space motion for manual arm repositioning, manual bar repositioning and/or bar optimization accommodation, and positioning a joint at a desired (e.g., preferred) location, in accordance with some embodiments. Each of these objectives may request a respective null space motion of the robotic arm. With only one additional (or limited) DoF of redundancy, these objectives may conflict with each other. Accordingly, there is a need to optimize the objectives simultaneously under various states of operation of a robotic arm and control the null space motion of the robotic arm in a balanced, optimal way.

Figure 29:
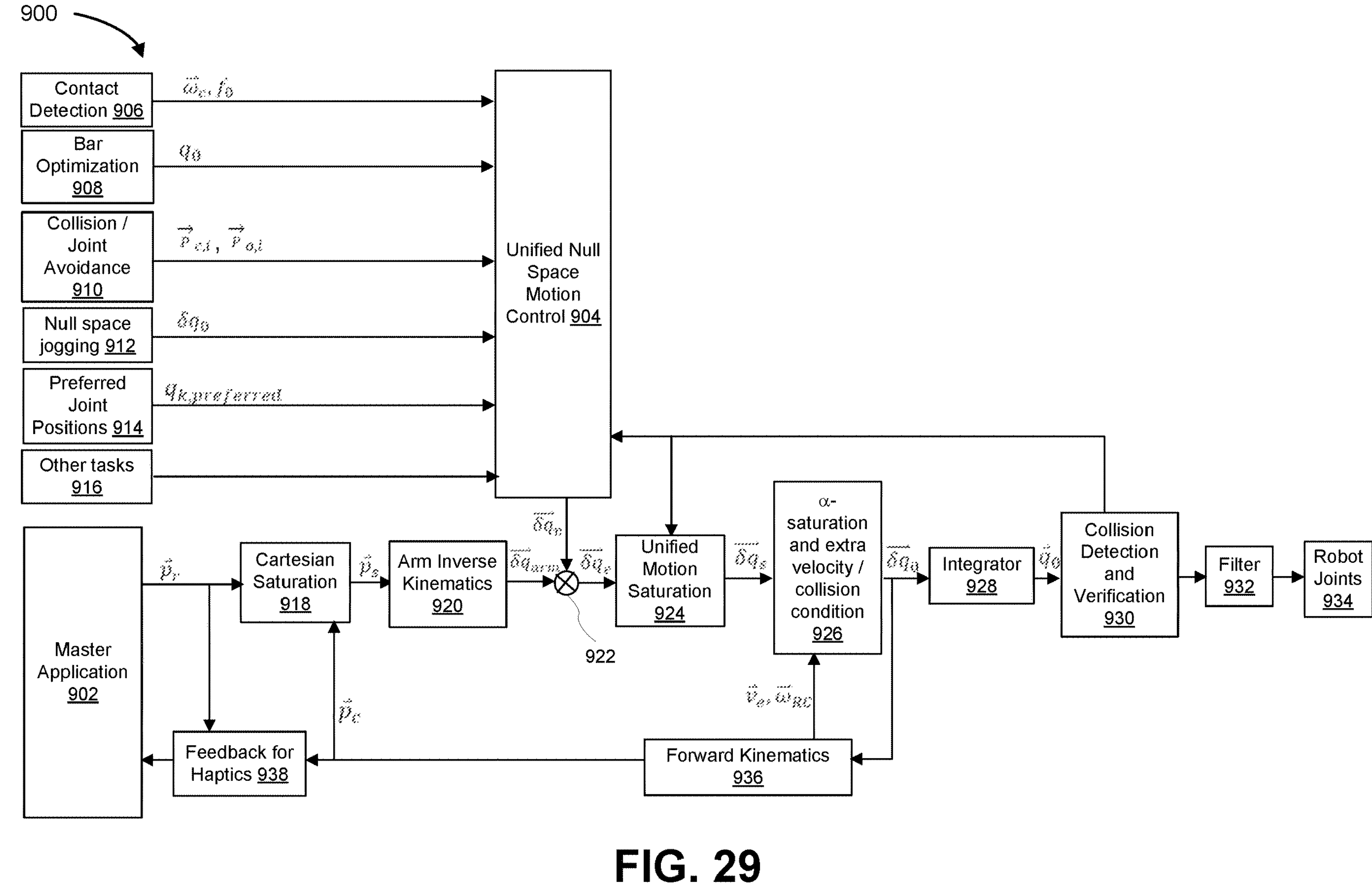
FIG. 29 illustrates a block diagram 900 of a kinematic architecture for a robotic system 200 according to some embodiments.

FIG. 29 illustrates a block diagram 900 of a kinematic architecture for a robotic system 200 according to some embodiments.

The block diagram 900 includes a master application 902. In some embodiments, the master application 902 is used by a surgeon during teleoperation to control an end effector of a robotic arm (e.g., robotic arm 210, FIGS. 21 and 22). In some embodiments, the master application 902 outputs (e.g., via a command from the surgeon) a master controller command $\vec{P}_r$ (e.g., an end effector trajectory), which is a vector that comprises a pose (e.g., a position and/or orientation) of the end effector about the RCM. In some embodiments, the master application 902 is initiated when a surgeon teleoperatively controls a robotic arm or instrument at a surgeon console, as described above.

FIG. 29 also shows a novel unified null space motion control module 904 in accordance with some embodiments. In some embodiments, the unified null space motion control module 904 executes concurrently (e.g., simultaneously) with the master application 902. In accordance with some embodiments of the present disclosure, the unified null space motion control module 904 manages a plurality of tasks (e.g., respective sets of operations of a plurality of task modules). In some embodiments, the plurality of tasks include contact detection 906, bar optimization 908, collision and/or joint avoidance 910, null space jogging 912, and preferred joint positions 914, among others. The plurality of tasks may also include other tasks 916, in accordance with some embodiments. In some embodiments, at least one of the plurality of tasks requires a respective null space motion of the robotic arm at a given time.

In some embodiments, the plurality of tasks includes contact detection 906. As described previously in FIGS. 23A to 24H, the robotic system includes a sensing architecture that includes one or more sensors, such as contact sensors 408, a six-axis load cell (e.g., six-axis load cell 404), a force sensor (e.g., A0 force sensor 402), and/or any other sensors (e.g., capacitive sensors) that may be located along one or more links and/or joints (e.g., links 302 and/or joints 304) of a robotic arm, in accordance with some embodiments. The robotic system detects (e.g., senses and measures) contact forces and/or torques on the robotic arm using the one or more sensors, in accordance with some embodiments. In some embodiments, based on the detected contact force and/or torque, the robotic system may determine a reaction scheme that utilizes null space motion of the robotic arm. For example, in accordance with the detected contact force and/or torque, null space control may be activated on the robotic arm to reduce the amount of contact force and/or torque, in accordance with some embodiments.

Referring again to FIG. 29, in some embodiments, the contact detection 906 module outputs two parameters $\vec{\omega}_C$ and $f_0$ to the unified null space motion control module 904, where $\vec{\omega}_C$ is a contact wrench that includes both force and torque from the contact sensors 408 and/or the six-axis load cell 404, and where $f_0$ is the force detected at the A0 joint (e.g., by the A0 force sensor 402). In some embodiments, if such forces exceed a certain threshold, null space motion may be activated on the robotic arm. For example, as described in FIGS. 25, 27, and 28, the robotic system may enable null space motion in accordance with a determination that a magnitude of the contact force or torque is between a lower contact force (e.g., Fr) or torque limit (e.g., $\tau_r$) and an upper contact force (e.g., $F_{limit}$) or torque limit (e.g., $\tau_{limit}$), in accordance with some embodiments.

In some embodiments, the plurality of tasks includes bar optimization 908. As described in FIG. 21, each of the robotic arms and/or the adjustable arm supports (e.g., bars) can be referred to as a respective kinematic chain. In some embodiments, a robotic arm and its underlying bar can be considered as one kinematic chain. For example, in FIG. 22, the robotic arm 210-1 and its underlying bar 220-1 can be part of the same kinematic chain, in accordance with some embodiments. In some embodiments, bar optimization comprises optimizing a pose (e.g., position and/or orientation) of the underlying bar (e.g., bar 220-1) that supports the robotic arm (e.g., robotic arm 210-1) while moving the robotic arm in null space so as to maintain the end effector (e.g., ADM 308) of the robotic arm 210 and/or a remote center of motion (RCM) of the tool 212 coupled thereto in a static pose. In some embodiments, the bar optimization module 908 outputs a position of the A0 joint (e.g., $q_0$) of the robotic arm to the unified null space motion control module 904. In some embodiments, the bar optimization module 908 can be extended to cover manual bar repositioning, where the resulting output (e.g., $q_0$) is integrated in the same manner.

In some embodiments, the plurality of tasks also includes collision and/or joint avoidance 910. In some circumstances, a robotic arm may collide with other objects, such as with another robotic arm, the patient support platform, and/or other objects in proximity to the robotic arm. Furthermore, in some circumstances, the joints of the robotic arm may be operating at or near their joint limits. In collision and/or joint avoidance 910, the robotic arm utilizes null space motion to avoid collisions and/or joint limits without affecting the end effector trajectory (e.g., $\vec{P}_r$), in accordance with some embodiments.

In some embodiments, the robotic system includes one or more encoders (e.g., joint encoders) that are positioned on one or more joints of the robotic arm. The joint encoders measure positions and/or angles of the joints of the robotic arm, and enable collision detection and handling in accordance with the joint encoder data, in accordance with some embodiments. In some embodiments, the robotic system creates a kinematic model based on the measured positions and/or angles of the joints. Collision and/or joint avoidance controls null space motion of the robotic arm based on a kinematic approach that uses the measurements of the robotic system (e.g., positions and/or angles of the joints of the robotic arm). Thus, the collision and/or joint avoidance 910 module is distinct from the contact detection 906 module, which uses sensor data to activate null space control.

In some embodiments, the collision and/or joint avoidance module 910 outputs two parameters $P_{c,i}$ and $P_{o,i}$ to the unified null space control module 904, where $P_{c,i}$ and $P_{o,i}$ correspond to the Cartesian coordinates of a collision control point and an obstacle point. When the robotic arm is near an obstacle (such as another robotic arm, another object of the robotic system, or an external object), one or more points on the robotic arm which are nearest to one or more corresponding points on the object can be identified, in accordance with some embodiments. The collision control points are the one or more points on the robotic arm, in accordance with some embodiments. The obstacle points are the one or more corresponding points on the obstacle of the robotic arm, in accordance with some embodiments.

In some embodiments, collision and/or joint avoidance 910 assumes that the underlying bar of the robotic arm is stationary. In some circumstances, moving a robotic arm in null space while keeping its underlying bar in a stationary position may not result in a solution. In these instances, the robotic system (e.g., using the unified null space motion control module 904) will also activate the bar optimization module 908 concurrently to enable null space motion of the robotic arm by translation (and/or rotation, and/or tilt) of the underlying bar, in accordance with some embodiments.

In some embodiments, the plurality of tasks also includes null space jogging 912 (e.g., robotic arm null space jogging and/or bar pose jogging). In null space jogging, a user can manually move a robotic arm in both directions along its underlying bar (e.g., along the positive and negative y-axis, FIG. 22) without affecting a pose of the end effector (e.g., null-space) at any time during the arm movement. In some embodiments, null space jogging can be activated by pressing a button on the robotic arm (e.g., the button 312 in FIG. 23A or other input button), or by using an external input such as a joystick, or by pushing on link(s) of the robotic arm which are equipped with built-in force, torque and/or contact sensors. In some embodiments, null space jogging includes utilizing the underlying bar's translation, which is parallel to arm base translation (e.g., along the positive and negative y-axis, FIG. 22), and enlarges the motion range of the jogging on each arm.

An example of null space jogging is admittance null space jogging. In some circumstances, when a surgeon is performing a teleoperation, a medical staff on the patient side may need to access the patient. In these situations, the medical staff can activate admittance null space jogging to manually control (e.g., manually manipulate) the null space that is available from the robotic arm itself and/or from the kinematic chain that includes the robotic arm and its underlying bar, to move the robotic arm to a pose that enables patient access. Stated another way, admittance null space jogging enables a user to manually reposition a robotic arm and/or a joint of the robotic arm at a preferred location while guaranteeing that the robotic arm moves in null space during the manual repositioning, in accordance with some embodiments. The null space jogging module 912 outputs to the unified null space motion control module 904 a velocity of the A0 joint (e.g., $\delta q_0$), in accordance with some embodiments.

FIG. 29 also shows that the plurality of tasks includes preferred joint positions 914. In some embodiments, there is a preferred value for the pose of a robotic arm. For example, some poses (e.g., positions and/orientations of joints and/or links of a robotic arm) may be preferred due to the kinematic ability of the robotic system, or because the poses are known to lead to reduced possibility of potential arm collisions during teleoperation. In the preferred joint positions 914, the robotic arm utilizes null space motion to calculate the corresponding preferred joint position(s) and move toward the preferred pose, in accordance with some embodiments. In some embodiments, the preferred joint value may be determined based on a procedure or kinematic metric (e.g. manipulability). The preferred joint positions module 914 outputs to the unified null space motion control module 904 the preferred position of a joint of the robotic arm (e.g., $q_{k,preferred}$), in accordance with some embodiments.

In some embodiments, the unified null space motion control module 902 determines (and outputs) a null space joint velocity of the robotic arm $\overrightarrow{\delta q_n}$. $\overrightarrow{\delta q_n}$ is a n×1 vector with components corresponding to the velocities of each of the joints of the robotic arm, wherein n denotes the number of joints of the robotic arm, in accordance with some embodiments. For a robotic arm that has seven joints (e.g., the robotic arm has one redundant DoF), $\overrightarrow{\delta q_n}$ is 7×1 vector.

In the block diagram 900, $\vec{P_r}$ (wherein r is the reference) is the master controller command for an end effector vector. The master application input may involve Cartesian saturation (918). By limiting the input to robot kinematic solver based on a current position of the robotic arm, any ill conditions in kinematics, such as the violation of linear assumption, singularity, robot workspace, collision detection limitation, etc., can be reduced or prevented, in accordance with some embodiments. At the same time, other proper saturations can be applied, in accordance with some embodiments. In some embodiments, the Cartesian saturation module 918 can also saturate the tool tip velocity to further ensure patient safety.

Once an initial inverse kinematic solution (e.g., $\overrightarrow{\delta q_{arm}}$) is computed and added (922) to the output (e.g., $\overrightarrow{\delta q_n}$) of the unified null space motion control module 904 and passed through a unified motion saturation module 924, the resultant inverse kinematic solution (e.g., $\overrightarrow{\delta q_s}$) is Checked Against (e.g., Via the α-Saturation and Extra Velocity/Collision Condition Module 926) velocity constraints on different arm body locations and joint speed limits, in accordance with some embodiments. At this point, the joint speed ($\overrightarrow{\delta q_o}$) is integrated (928) to determine joint position commands (e.g., $\overrightarrow{q_o}$). After a collision detection and verification module 930, a filter (932) is also applied to the joint position commands (e.g., $\overrightarrow{q_o}$) to generate a smooth signal to the commands, in accordance with some embodiments.

Figure 30A:
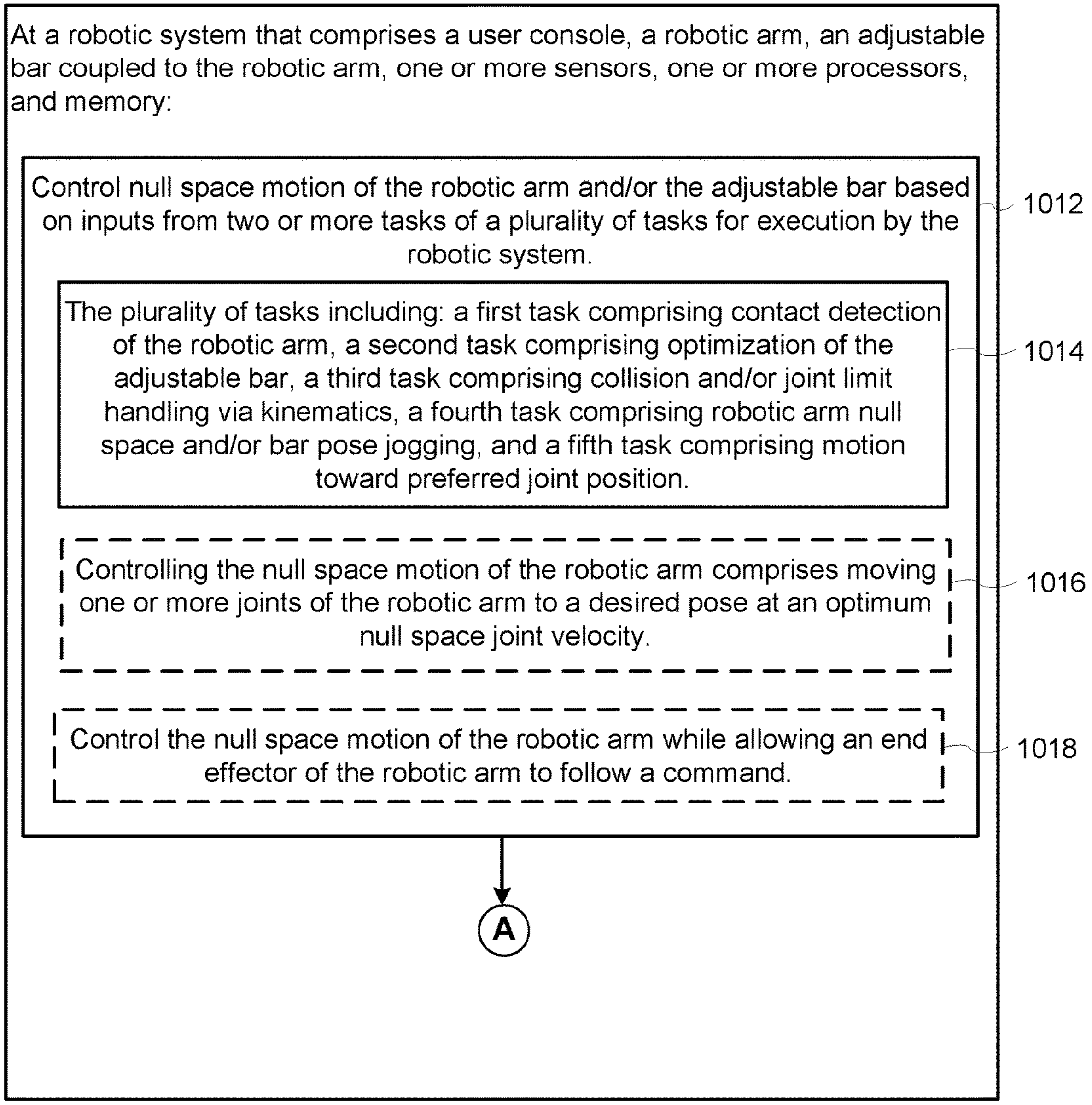
Figure 30C:
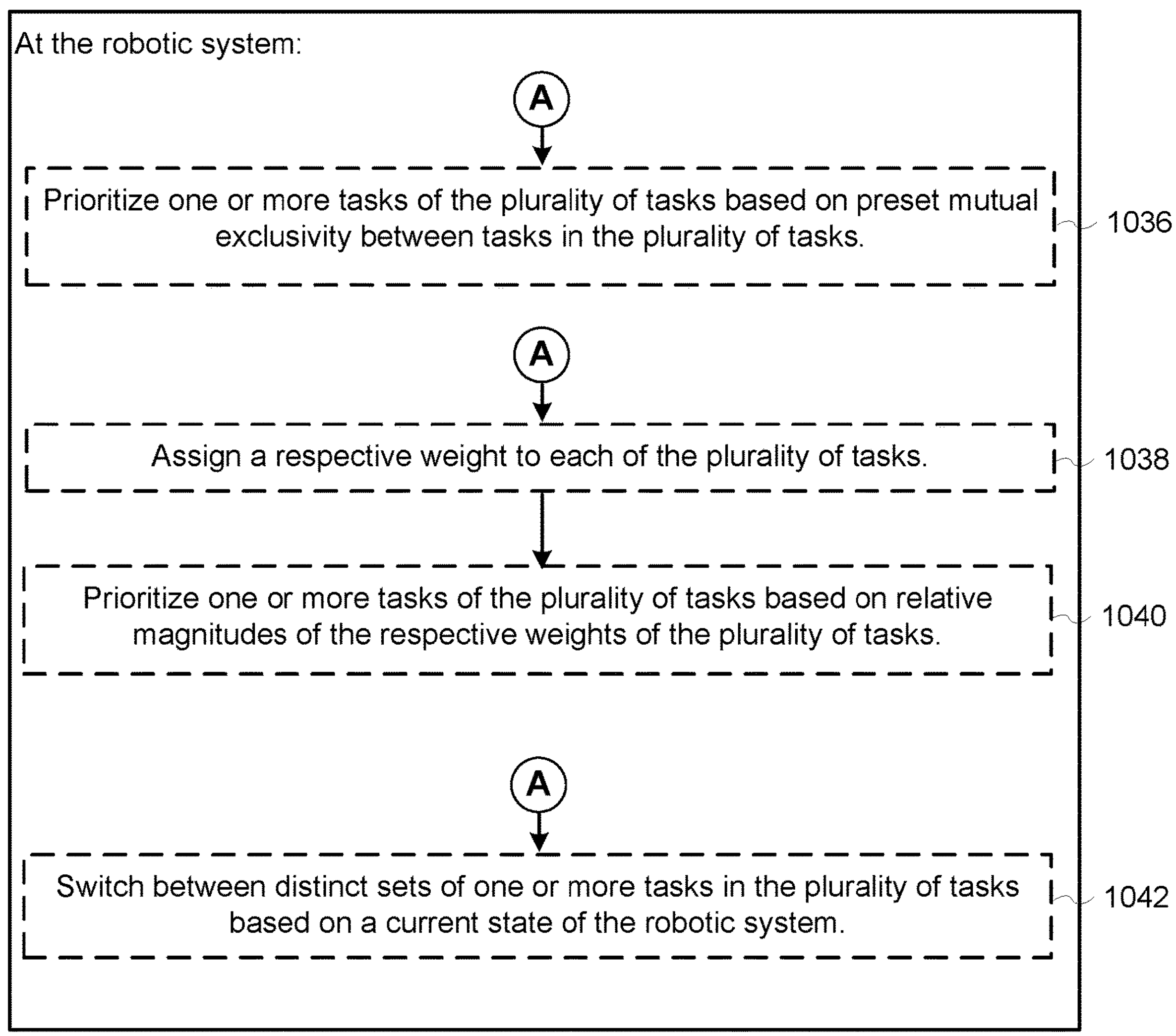

FIGS. 30A to 30C illustrate a flowchart diagram of a method 1000 of controlling null space motion of a robotic arm according to some embodiments. In accordance with some embodiments of the present disclosure, the method 1000 is performed by one or more processors of a robotic system (e.g., the robotic medical system 200 as illustrated in FIGS. 21 and 22, or a robotic surgery platform).

The robotic system includes a user console (e.g., a physician console for performing teleoperation and other operations of the robotic system). The robotic system also includes (1004) a robotic arm (e.g., the robotic arm 210 in FIGS. 21, 22, 23A, 23B, 24A, and 24H). In some embodiments, the robotic arm is a first robotic arm of two or more robotic arms of the robotic system (see, e.g., FIGS. 21 and 22). In some embodiments, the robotic system includes a single robotic arm. In some embodiments, the robotic arm has at least one degree of freedom of redundancy. For example, in some embodiments, a robotic arm can have at least seven joints (e.g., joints 304, FIG. 23), thus resulting in at least seven DoFs (e.g., at least one redundant DoF). A robotic arm 210 with at least seven DoFs has at least one more DoF than the minimum number of DoFs (e.g., six DoFs) for performing a given task, in accordance with some embodiments. When a robotic arm has seven joints, one of the joints can be considered a redundant joint, in accordance with some embodiments. The one or more redundant joints can allow the robotic arm 210 to move in null space to both maintain the pose of the ADM 308 and a position of an RCM and avoid collision(s) with other robotic arms or objects, in accordance with some embodiments. The robotic system also includes an adjustable bar (e.g., bar 220, FIGS. 21 and 22) coupled to the robotic arm. The robotic system further includes one or more processors and memory. The memory stores instructions that are executed by the one or more processors.

The robotic system controls (1012) null space motion of the robotic arm 210 and/or the adjustable bar 220 based on inputs from two or more tasks of a plurality of tasks for execution by the robotic system, in accordance with some embodiments.

In some embodiments, and as illustrated in FIG. 29, the plurality of tasks includes (1014) a first task comprising contact detection of the robotic arm (e.g., contact detection 906), a second task comprising optimization of the adjustable bar (e.g., bar optimization 908), a third task comprising collision and/or joint limit handling via kinematics (e.g., collision/joint avoidance 910), a fourth task comprising robotic arm null space and/or bar pose jogging (e.g., null space jogging 912), and a fifth task comprising motion toward preferred joint position (e.g., preferred joint positions 916). In some embodiments, each of the plurality of tasks requires a respective null space motion of the robotic arm. In some embodiments, the robotic system comprises a null space motion control system (e.g., unified null space motion control module 904) that controls the null space motion of the robotic arm in a way that optimizes the execution of the tasks.

In some embodiments, the plurality of tasks are related to a plurality of objectives, such as kinematic collision avoidance, joint limit avoidance, excessive contact avoidance, and admittance null space motion for manual arm repositioning.

In some embodiments, controlling the null space motion of the robotic arm comprises moving (1016) one or more joints of the robotic arm to a desired pose (e.g., position and orientation) at an optimum null space joint velocity.

For example, in FIG. 29, the master application 902 outputs a master controller command $\vec{P}_r$ that comprises a pose (e.g., a position and/or orientation) of an end effector of the robotic arm, in accordance with some embodiments. The unified null space motion control module 904 outputs a null space joint velocity vector $\overrightarrow{\delta q_n}$ having components corresponding to the velocities of the joints of the robotic arm, in accordance with some embodiments.

In some embodiments, the robotic system controls the null space motion of the robotic arm while allowing (1018) an end effector of the robotic arm to follow a command. In some embodiments, the command can be generated via teleoperation of a robotic arm by a surgeon. In other embodiments, the command can be generated via manual manipulation of the robotic arm, such as via slave clutch.

For example, in FIG. 29, the unified null space motion control module 904 controls the null space motion of the robotic arm. The unified null space motion control module 904 can execute concurrently with the master application 902, which controls a pose of the end effector of the robotic arm.

In some embodiments, the robotic system further includes (1020) one or more force sensors that are positioned on the robotic arm.

In some embodiments, the one or more force sensors include (1022) a contact sensor (e.g., contact sensor 408) that is positioned on a link of the robotic arm. For example, as described in FIGS. 24B, 24C, 24D, 4E, 24F, and 24G, the contact sensor 408 is a force sensor that can be positioned on a link 302 of the robotic arm.

In some embodiments, the one or more force sensors include (1024) a contact sensor that is positioned on a joint or distal end of the robotic arm. For example, in some embodiments, the contact sensors 408 in FIG. 24B can be positioned on a joint 304 of the robotic arm 210. The contact sensors 408 can also be located along a length of a link 302, such as a link on a proximal portion and/or a link on a distal portion of the robotic arm 210. FIG. 24G also illustrates the contact sensors 408 positioned on a distal end of the robotic arm.

In some embodiments, the first task (e.g., contact detection 906) further includes (1026) using the one or more force sensors to detect contact on the robotic arm.

For example, the robotic system includes a sensing architecture that includes one or more sensors, such as contact sensors 408, a six-axis load cell (e.g., six-axis load cell 404), a force sensor (e.g., A0 force sensor 402), and/or any other sensors (e.g., capacitive sensors) that may be located along one or more links and/or joints (e.g., links 302 and/or joints 304) of a robotic arm, in accordance with some embodiments. These sensors detect contact on the robotic arm. For example, the contact sensors 408 are force sensors (or force and moment sensors), in accordance with some embodiments. The six-axis load cell 404 is a force and moment sensor, in accordance with some embodiments.

In some embodiments, the robotic system further includes (1028) one or more force sensors that are positioned on a joint of the robotic arm. The second task includes (1030) using forces sensed on one or more sensors to adjust a pose (e.g., position and/or orientation) of the adjustable bar relative to the robotic arm 210, in accordance with some embodiments.

For example, as illustrated in FIG. 24A, the robotic system includes a force sensor 402 that is positioned on the A0 joint 304-1 of the robotic arm, in accordance with some embodiments. The bar optimization 908 task includes using forces sensed on the A0 force sensor to adjust a pose (e.g., position and/or orientation) of the underlying bar of the robotic arm, in accordance with some embodiments.

For example, the robotic arm and its underlying adjustable bar form one kinematic chain (or are part of the same kinematic chain), in accordance with some embodiments. In some embodiments, bar optimization comprises optimizing a pose (e.g., position and/or orientation) of the underlying bar (e.g., bar 220-1) that supports the robotic arm (e.g., robotic arm 210-1) while moving the robotic arm in null space so as to maintain the end effector (e.g., ADM 308) of the robotic arm and/or a remote center of motion (RCM) of a tool coupled thereto in a static pose.

In some embodiments, the robotic system further includes (1032) one or more encoders (e.g., joint encoders) positioned on a joint of the robotic arm (e.g., for measuring a position and/or angle of the robotic arm). The third task (e.g., joint collision/avoidance 910) comprises (1034) using the one or more encoders to detect collision and mitigate the collision via kinematics control, in accordance with some embodiments.

Unlike the first task (e.g., contact detection 906), which activates null space motion according to data from one or more sensors of the robotic arm, the third task (e.g., joint collision/avoidance 910) uses positions and/or angles of the joints measured by the joint encoders to build a kinematic model and mitigate joint collision using null space kinematics control, in accordance with some embodiments.

In some embodiments, the robotic system prioritizes null space motion of the various tasks based on exclusivity, weighting, and/or switching.

In some embodiments, the robotic system prioritizes (1034) one or more tasks of the plurality of tasks based on preset mutual exclusivity between tasks in the plurality of tasks.

For example, when the robotic system executes certain task(s), certain other task(s) are disabled (e.g., by setting their weights to zero), in accordance with some embodiments. In one example, when bar optimization 908 is enabled, link/joint collision avoidance 910 disabled, in accordance with some embodiments. In another example, when null space jogging 912 is used, all other tasks (e.g., contact detection 906, bar optimization 908, link/joint collision avoidance 910, and preferred joint positions 914) are disabled, in accordance with some embodiments.

In some embodiments, the robotic system assigns (1038) a respective weight to each of the plurality of tasks.

For example, in some embodiments, the robotic system may assign a respective weight to each of the plurality of tasks based on a relative importance of the task, with more important tasks given higher respective weights than less important tasks. In some embodiments, the weights are dynamically adjustable weights that are calculated on the fly based on currently detected sensor data and/or joint encoder data, and/or a current state of the robotic system (e.g., idle, in surgery, in set-up, etc.).

In some embodiments, the robotic system also prioritizes (1040) one or more tasks of the plurality of tasks based on relative magnitudes of the respective weights of the plurality of tasks. For example, the tasks that are prioritized have the highest weights amongst the plurality of tasks. Unlike the other prioritization schemes such as exclusivity or switching (see below), wherein one or more tasks might be disabled, and therefore not considered in the determination of the null space motion of the robotic arm, in the weighting scheme, all the tasks are considered based on a relative importance that is determined by their respective assigned weights, in accordance with some embodiments.

In some embodiments, the robotic system switches (1042) between distinct sets of one or more tasks in the plurality of tasks based on a current state of the robotic system.

Switching enables different tasks to be enabled at different times, in accordance with some embodiments. Switching depends on the state of the robotic system (e.g., during set-up, surgery, in impedance mode, in admittance mode etc.) to produce the desired outcome in each state, in accordance with some embodiments.

In some instances, a user may activate impedance mode during a setup procedure to manually manipulate the robotic arm. When the robotic arm is in impedance mode, collision and/or joint limit handling (e.g., collision/joint avoidance (910)), contact detection (906), and null space jogging (912) are switched off, in accordance with some embodiments. Bar optimization (908) can be activated to facilitate configuration of the robotic arm/adjustable bar kinematic chain to an optimized pose for surgery, in accordance with some embodiments.

In another example, collision and/or joint avoidance (910) assumes that the underlying bar of the robotic arm is stationary, in accordance with some embodiments. In some circumstances, moving a robotic arm in null space while keeping its underlying bar in a stationary position may not result in a solution, in accordance with some embodiments. In these instances, the robotic system (e.g., using the unified null space motion control module 904) will also activate the bar optimization module 908 concurrently to enable null space motion of the robotic arm by translation (and/or rotation, and/or tilt) of the underlying bar, in accordance with some embodiments.

In some embodiments, the preferred joint positions module 914 is disabled by default and is only activated as an auxiliary feature upon user command. When activated, the robotic system switched to a different state where a cost function (see, e.g., FIG. 31) is augmented with preferred-joint positions and other tasks are disabled or enabled with potentially different weights.

Figure 31A:
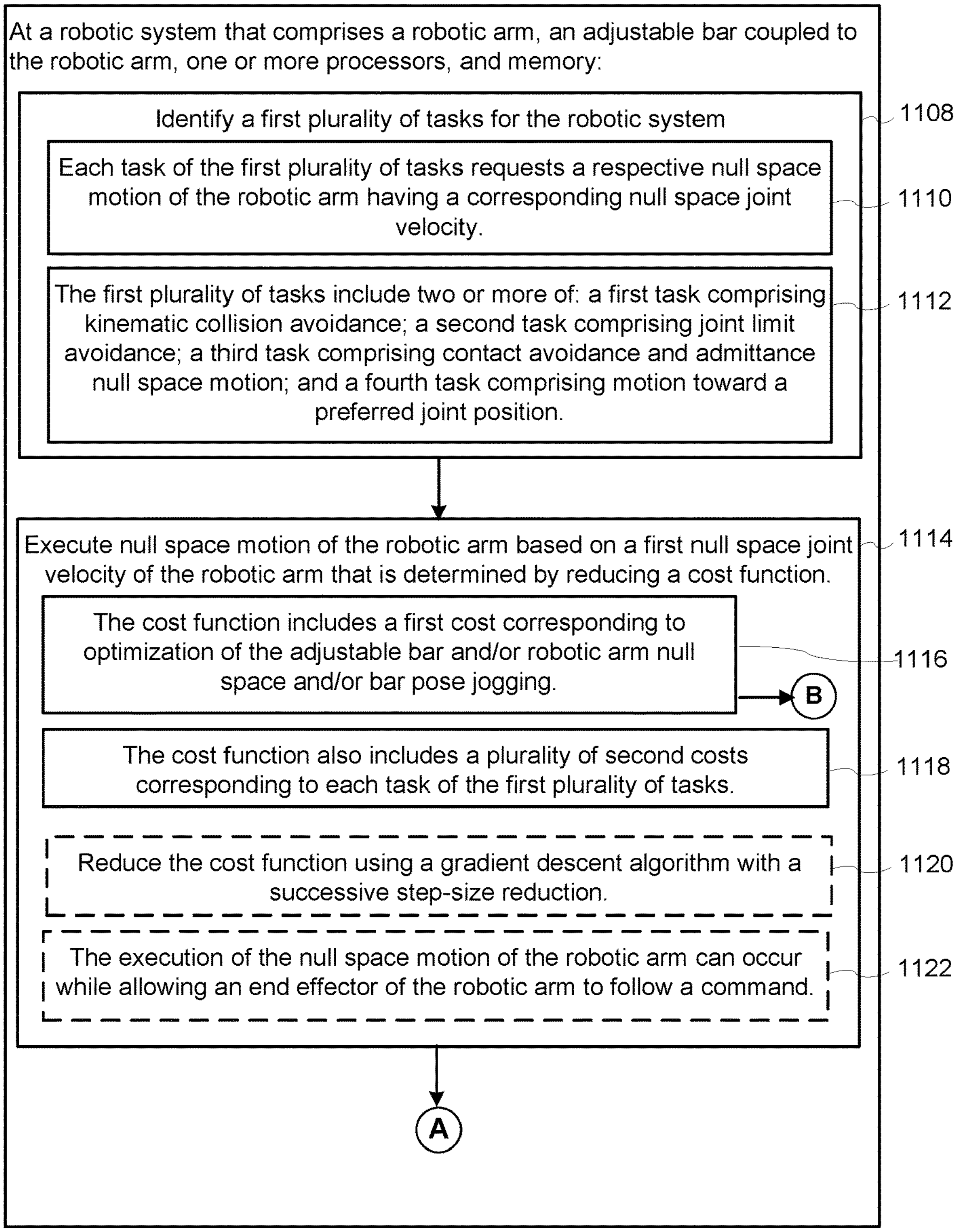
FIGS. 31A and 31B illustrate a flowchart diagram of a method for determining a null space joint velocity of a robotic arm according to some embodiments.
Figure 31B:
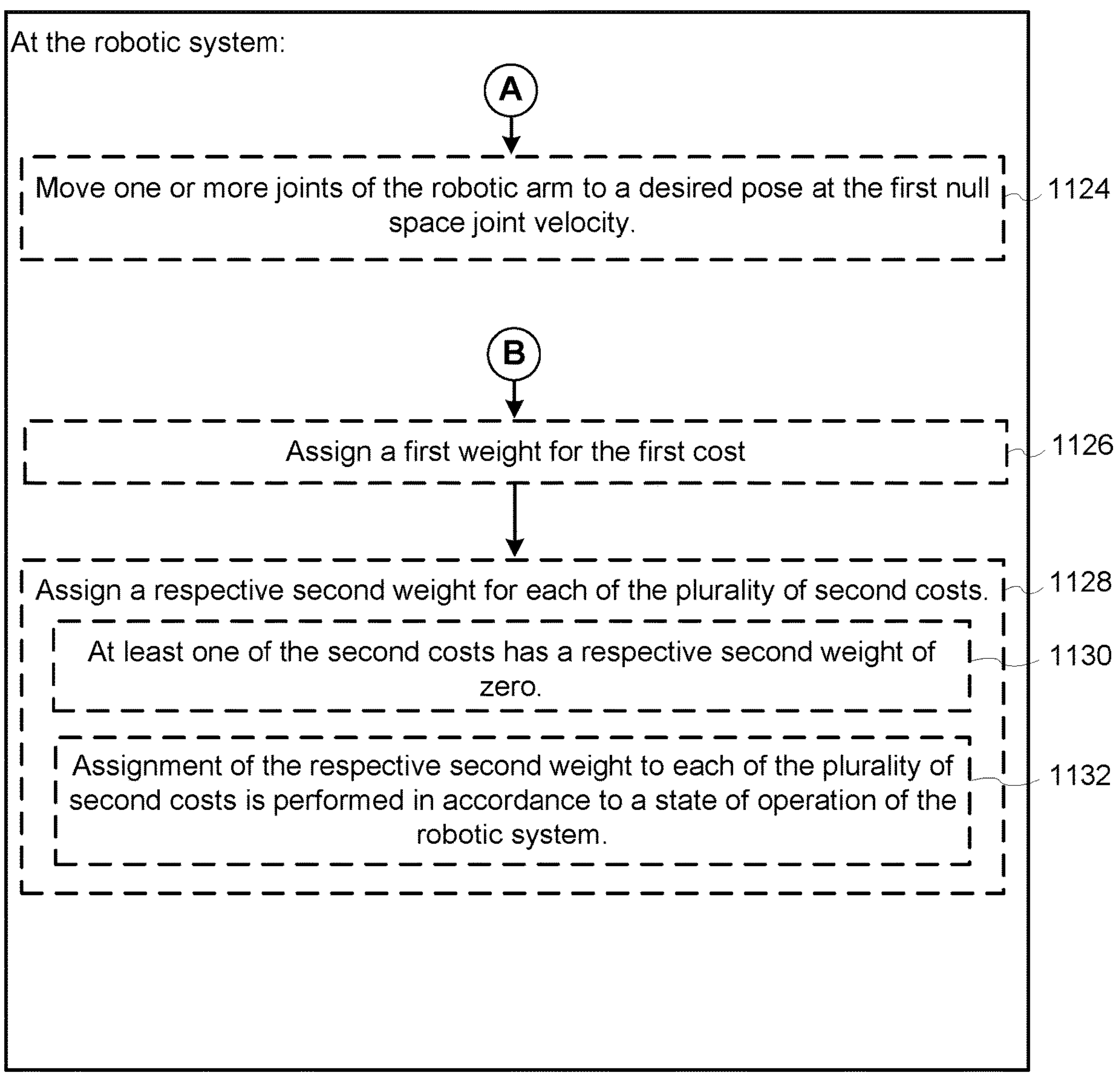

In accordance with another aspect of the present disclosure, the null space joint velocity $\overrightarrow{\delta q_n}$ (e.g., the output of the null space motion control module 902) can be determined by optimization, in accordance with some embodiments. FIGS. 31A and 31B illustrate a flowchart diagram of a method 1100 for determining a null space joint velocity of a robotic arm according to some embodiments. In accordance with some embodiments of the present disclosure, the method 1100 is performed by one or more processors of a robotic system (e.g., the robotic medical system 200 as illustrated in FIGS. 21 and 22, or a robotic surgery platform).

The robotic system comprises a robotic arm (e.g., the robotic arm 210 in FIGS. 21, 22, 23A, 23B, 24A, and 24H). In some embodiments, the robotic arm is a first robotic arm of two or more robotic arms of the robotic system (see, e.g., FIGS. 21 and 22). In some embodiments, the robotic system includes a single robotic arm. The robotic system also includes an adjustable bar (e.g., bar 220, FIGS. 21 and 22) coupled to the robotic arm. The robotic system also includes one or more processors, and memory. The memory stores one or more programs configured for execution by the one or more processors.

The robotic system identifies (1108) a first plurality of tasks (e.g., S) for the robotic system, in accordance with some embodiments. In some embodiments, the first plurality of tasks comprises objectives (e.g., goals) of the robotic system (e.g., objectives to be met by a (e.g., single, each) robotic arm of the robotic system). For example, the first plurality of tasks (e.g., objectives) include kinematic collision avoidance, joint limit avoidance, excessive contact avoidance, admittance null space motion for manual arm repositioning, and positioning a robot joint at a preferred location, in accordance with some embodiments. In some embodiments, the first plurality of tasks include tasks that are depicted in the block diagram 900. For example, the first plurality of tasks include contact detection (906), bar optimization (908), collision/joint avoidance (910), null space jogging (912), preferred joint positions (914), and/or other tasks 916, in accordance with some embodiments.

In some embodiments, each task (e.g., $s_i \subseteq S$) of the first plurality of tasks (e.g., S) requests (1110) a respective (e.g., a distinct) null space motion of the robotic arm having a corresponding null space joint velocity (e.g., $\dot{q}_n$)

In some embodiments, the first plurality of tasks include (1112) two or more of: a first task comprising kinematic collision avoidance, a second task comprising joint limit avoidance, a third task comprising contact avoidance and admittance null space motion, and a fourth task comprising motion toward a preferred joint position.

In some embodiments, the first task comprising kinematic collision avoidance corresponds to the collision/joint avoidance task (910) that is described in FIG. 29. In some embodiments, the first task can be represented by:

$$s_1 = \frac{\|p_{c,i} - p_{o,i}\| - d_{trigger}}{d_{stop} - d_{trigger}} \subseteq S \tag{9}$$

wherein $p_{c,i}$ are the Cartesian coordinates of the control point i, $p_{o,i}$ are the Cartesian coordinates of the obstacle point i, $\|P_{c,i}-P_{o,i}\|$ is the norm (e.g., magnitude) of the difference vector $(p_{c,i}-P_{o,i})$, $d_{trigger}$ is a threshold distance above which null space movement of a joint is triggered, and $d_{stop}$ is the upper limit in which null space movement of a joint is stopped. As described with respect to the collision and/or joint avoidance module 910, when the robotic arm is near an obstacle such as another robotic arm, another object of the robotic system, or an external object etc., a point on the robotic arm that is nearest to a corresponding point on the object can be identified, in accordance with some embodiments. The control point i, $p_{o,i}$ (or the collision control point) refers to the point on the robotic arm whereas the obstacle point is the corresponding point on the obstacle of the robotic arm, in accordance with some embodiments.

In some embodiments, the second task comprising joint limit avoidance corresponds to the collision/joint avoidance task (910) that is described in FIG. 29. In some embodiments, the second task can be represented by:

$$s_2 = \frac{\|q_{,i} - q_{lim,i}\| - q_{free,i}}{q_{stop,i} - q_{free,i}} \subseteq S \tag{10}$$

wherein $q_{,i}$ is a current joint value of joint i, $q_{lim,i}$ is a limit (e.g., a constant value) of the joint i, $\|_{q,i}-q_{lim,i}\|$ is the norm (e.g., magnitude) of the vector difference $(q_{,i}-q_{lim,i})$, $q_{free,i}$ is the free limit value for joint i in which null space movement of the joint i is triggered, and $g_{stop,i}$ is the upper limit value for joint i in which null space movement of the joint i is stopped.

In some embodiments, the second task is activated (e.g., by the robotic system, e.g., by the unified null space motion control module 902) when the current joint value $q_{,i}$ is between the free limit value (e.g., $q_{free,i}$) and the upper limit value $(g_{stop,i})$.

In some embodiments, the third task comprising contact avoidance and admittance null space motion corresponds to the contact detection task (906) and the null space jogging task (912) in FIG. 29. In some embodiments, the third task can be represented by:

$$s_3 = \frac{|f_1| - f_{min}}{f_{max} - f_{min}} \subseteq S \tag{11}$$

wherein $|f_1|$ is the magnitude of an external force $f_1$ detected by a force sensor, a contact sensor, and/or a six-axis load cell that is located on the A0 joint. In some embodiments, $f_1$ in Equation (11) is the same as the output $f_0$ from the contact detection module 906), and $f_{min}$ and $f_{max}$ are the lower and upper force threshold limits in which null space motion will be enabled. For example, as described in FIGS. 25, 27, and 28, the robotic system may enable null space motion in accordance with a determination that a magnitude of the contact force (e.g., $|f_1|$) is between a lower contact force (e.g., Fr) limit and an upper contact force limit (e.g., $F_{limit}$), in accordance with some embodiments.

In some embodiments, the fourth task comprising motion toward the preferred joint position corresponds to the preferred joint positions task (914) in FIG. 29. In some embodiments, the fourth task can be represented by:

$$s_4 = \frac{q_k - q_{k,preferred}}{q_{k,max} - q_{k,mim}} \subseteq S \tag{12}$$

wherein $q_k$ is a current value of the joint k, $q_{k,\ preferred}$ is the preferred position of the joint k, ($q_{k,max}$-$q_{k,min}$) is the range of motion of the joint k. For a robotic system with seven joints (e.g., seven DoF), k has integer values ranging from 1 to 7 inclusive.

In Equations (9) to (12), $s_i$ (wherein i=1 to 4) is a non-negative value and represents a respective normalized "severity" of a corresponding null space motion request. For example, if a joint is at the configured joint limit, the null space motion request from this event will have normalized severity s=1, and if the same joint is away from joint limit by a configured amount, S=1, in accordance with some embodiments. Using the fourth task as an example, if a joint is currently at its preferred joint position, the current joint value $q_k$ in Equation (12) is $q_{k,preferred}$, and accordingly $s_4$=0, meaning that there is no "severity" because the joint is already at its preferred joint position, in accordance with some embodiments.

Referring again to FIG. 31, in some embodiments, the robotic system executes (1114) null space motion of the robotic arm based on a first null space joint velocity of the robotic arm that is determined by reducing (e.g., optimizing) a cost function (e.g., H(q)). The cost function H(q) includes (1116) a first cost corresponding to optimization of the adjustable bar and/or robotic arm null space and/or bar pose jogging. The cost function also includes (1118) a plurality of second costs corresponding to each task of the first plurality of tasks, in accordance with some embodiments.

In some embodiments, the cost function H(q) can be written as:

$$H(q) = \frac{1}{2}\sum w_i s_i^2 + w_m n_J^T q \tag{13}$$

The cost function H(q) has a first cost $w_m n_j^T q$, corresponding to optimization of the adjustable bar and/or robotic arm null space and/or bar pose jogging. $W_m$ is the weight for bar optimization and/or robotic arm null space and/or bar pose jogging. $n_j$ is the null-space basis vector of the robotic arm Jacobian, in accordance with some embodiments. In some embodiments, q is the null space velocity corresponding to the first cost. In some embodiments, the first cost corresponds to the bar optimization task (908) and the null space jogging task (912) in FIG. 29.

The cost function H(q) has second costs $$\frac{1}{2}\sum w_i s_i^2,$$

wherein $s_i \subseteq S$ for i=1 to 4, as defined in Equations (9) to (12) above, in accordance with some embodiments. As described above, $s_i$ is a respective normalized "severity" of a corresponding null space motion request, and $w_i$ is a respective weight for the corresponding $S_i$, in accordance with some embodiments. As defined herein, the cost function H(q) is a scalar function and each of the first cost and the second costs has a non-negative value (e.g., each of the terms in H(q) has a value that is zero or positive), in accordance with some embodiments.

In some embodiments, the robotic system reduces (1120) the cost function using a gradient descent algorithm with a successive step-size reduction.

In some embodiments, H(q) is optimized using a Gradient Descent formulation that is given by:

$$\overrightarrow{\delta q_n} = -\alpha \nabla H(q) \tag{14}$$

The solution of the gradient descent formulation is $\overrightarrow{\delta q}_n$, which is the null space joint velocity of the robotic arm, in accordance with some embodiments. $\overrightarrow{\delta q}_n$ is also the output of the unified null space motion control module 902 in FIG. 29, in accordance with some embodiments. The step size a can be a constant or variable parameter updated using algorithms such as Armijo's rule, in accordance with some embodiments. In some embodiments, a closed-form solution after solving ∇H(q) can be written as $$\overrightarrow{\delta q_n} = -\alpha\left(w_l \sum k_i s_i J_{c,i}^T \frac{p_{c,i} - p_{o,i}}{\|p_{c,i} - p_{o,i}\|} + w_j \sum k_j s_j e_j + w_f k_f s_f f_1 + w_p k_p s_p e_k + w_m n_J\right) \tag{15}$$

wherein k are functions of avoidance range $d_{stop}$–$d_{trigger}$ for kinematic collision avoidance and $g_{stop,j}$–$q_{free,j}$ for joint limit avoidance and $$\text{etc., } J_{c,i}^T$$

is the Jacobian of the collision point of the i-th collision event, and $e_j$ is the standard basis of the j-th dimension.

In some embodiments, the robotic arm executes (1122) the null space motion of the robotic arm while allowing an end effector of the robotic arm to follow a command, such as during teleoperation of the robotic arm and/or during manual manipulation of a robotic arm (e.g., via slave clutch).

For example, in FIG. 29, the unified null space motion control module 904 controls the null space motion of the robotic arm, in accordance with some embodiments. The unified null space motion control module 904 executes concurrently with the master application 902, which controls a pose of the end effector of the robotic arm, in accordance with some embodiments.

In some embodiments, the robotic system moves (1124) one or more joints of the robotic arm to a desired pose (e.g., position and orientation) at the first null space joint velocity.

In some embodiments, the robotic system assigns (1126) a first weight for the first cost. The robotic system also assigns (1128) a respective second weight for each of the plurality of second costs, in accordance with some embodiments.

For example, referring to Equation (13), the robotic system assigns a first weight $w_m$ for the first cost, in accordance with some embodiments. The robotic system also assigns a respective second weight $w_i$, wherein i=1 to 4 (e.g., or another number that corresponds to the number of tasks involved in the prioritization and unification scheme), for each of the plurality of second costs, in accordance with some embodiments.

Reducing the cost function comprises minimizing the cost function H(q), in accordance with some embodiments. In some embodiments, the cost function is minimized based on the exclusivity scheme that is described in FIG. 30. For example, in some embodiments, whenever the first cost is used (i.e. $w_m$ is not zero), the second costs are all ignored (e.g., $w_1$, $w_2$, $w_3$, and $w_4$ are all zero). This scenario applies to a situation when the robotic arm receives a bar optimization command, in accordance with some embodiments. In this instance, the robotic arm uses the null space motion for that purpose only, in accordance with some embodiments.

In some embodiments, at least one of the second costs has (1130) a respective second weight of zero.

In some embodiments, assignment of the respective second weight to each of the plurality of second costs is performed in accordance with a state of operation of the robotic system.

For example, $w_1$, $w_2$, $w_3$, and $w_4$ can represent weights used for setting the priorities for a respective null space motion request for each task (e.g., $s_i \subseteq S$) of the first plurality of tasks (e.g., S), in accordance with some embodiments. In some embodiments, the actual values of the weights $w_1$ to $w_4$ can vary depending on the state of operation of the robotic system or functions of null space motion request severity (e.g., $s_i$). For example, in coordinated table motion, higher weights are assigned to the kinematic collision avoidance (e.g., $s_1$) and joint limit avoidance (e.g., $s_2$) tasks than to the preferred joint position task (e.g., $s_4$), in accordance with some embodiments. That is to say, the weight $w_1$ corresponding to the kinematic collision avoidance task $s_1$ and the weight $w_2$ corresponding to the joint limit avoidance task $s_2$ have larger values than the weight $w_4$ corresponding to the preferred joint position task $s_4$, in accordance with some embodiments.

In some embodiments, in the bar optimization task, only preferred joint position is allowed. Accordingly, a user can set $w_4$ to an appropriate weight and disable all other requests that are represented by the second cost by setting the weights $w_1$, $w_2$ and $w_3$ to zero, in accordance with some embodiments. As another example of request severity dependent weights, when admittance null space motion/contact avoidance request appears or when $s_3>0$, $w_1$, $w_2$ and $w_4$ can all be set to zero so that the user take full control of the robotic arm achieve the user's objectives, in accordance with some embodiments.

3. Implementing Systems and Terminology

Embodiments disclosed herein provide systems, methods and apparatus for detecting and responding to interactions with a robotic arm while teleoperation is performed using the robotic arm.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The functions for transitioning to a manual manipulation mode described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the scope of the invention. For example, it will be appreciated that one of ordinary skill in the art will be able to employ a number of corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the embodiments shown herein but is to be accorded the widest scope consistent with the principles and novel features disclosed herein.

Some embodiments or implementations are described with respect to the following clauses:

Clause 1. A robotic system, comprising:

a robotic arm;

one or more sensors;

one or more processors; and memory storing instructions that, when executed by the one or more processors, cause the one or more processors to:

detect, via the one or more sensors, a contact force or torque that is exerted on the robotic arm by an external object; and in response to detecting the contact force or torque, in accordance with a determination that a magnitude of the contact force or torque is between a lower contact force or torque limit and an upper contact force or torque limit, enable a first set of controlled movements on the robotic arm in accordance with the detected contact force or torque.

Clause 2. The robotic system of clause 1, wherein enabling a first set of controlled movements on the robotic arm comprises activating null space motion of the robotic arm.

Clause 3. The robotic system of clause 1 or 2, wherein the memory further includes instructions that, when executed by the one or more processors, cause the one or more processors to:

in response to detecting the contact force or torque, in accordance with a determination that the contact force or torque exceeds the upper contact force or torque limit, disable movement of a part of the robotic system.

Clause 4. The robotic system of any of clauses 1-3, wherein the memory further includes instructions that, when executed by the one or more processors, cause the one or more processors to:

in response to detecting the contact force or torque, in accordance with a determination that the contact force or torque is less than the lower contact force or torque, forgo enabling the first set of controlled movements on the robotic arm in accordance with the detected contact force or torque.

Clause 5. The robotic system of any of clauses 1-4, wherein:

the one or more sensors include one or more contact sensors; and the contact force or torque is detected using the one or more contact sensors.

Clause 6. The robotic system of clause 5, wherein the one or more contact sensors are located on a link of the robotic arm.

Clause 7. The robotic system of clause 6, wherein the link of the robotic arm is a distal link or a proximal link.

Clause 8. The robotic system of any of clauses 1-7, wherein:

the one or more sensors include a multi-axis load cell; and the contact force or torque is detected using the multi-axis load cell.

Clause 9. The robotic system of clause 8, wherein the multi-axis load cell includes a six-axis load cell that is located on a distal portion of the robotic arm.

Clause 10. The robotic system of any of clauses 1-9, wherein the memory further includes instructions that, when executed by the one or more processors, cause the one or more processors to:

receive a first user command comprising a first velocity of the robotic arm;

in accordance with the determination that the magnitude of the contact force is between a lower contact force limit and an upper contact force limit:

determine a direction of the contact force;

determine a direction of the torque;

determine a first angle formed by a translational velocity of the robotic arm and the direction of the contact force; and determine a second angle formed by a rotational velocity of the robotic arm and the direction of the torque;

in accordance with a determination that the first angle is within a first angular threshold and the second angle is within a second angular threshold, enable movement of one or more joints of the robotic arm at the first velocity; and in accordance with at least one of: (i) a determination that the first angle exceeds the first angular threshold, or (ii) a determination that the second angle exceeds the second angular threshold, disable movement of the robotic arm.

Clause 11. The robotic system of clause 10, wherein the first angular threshold and the second angular threshold are determined according to a measurement uncertainty of one or more contact sensors used to detect the contact force.

Clause 12. The robotic system of any of clauses 1-9, wherein the memory further includes instructions that, when executed by the one or more processors, cause the one or more processors to:

receive a second user command comprising a requested velocity of the robotic arm; in accordance with the determination that the magnitude of the torque is between the lower torque limit and the upper torque limit:

determine a direction of the torque;

determine a third angle formed by the direction of the torque and the requested velocity of the robotic arm;

in accordance with a determination that the third angle is within a third angular threshold, enable movement the robotic arm at the requested velocity; and in accordance with a determination that the third angle exceeds the third angular threshold, disable movement of the robotic arm.

Clause 13. The robotic system of clause 12, wherein the magnitude of the torque is determined with respect to a remote center of motion of the robotic arm.

Clause 14. The robotic system of clause 12 or 13, wherein the third angular threshold is determined according to a measurement uncertainty of a six-axis load cell used to detect the torque.

Clause 15. A robotic system, comprising:

a robotic arm;

one or more sensors;

one or more processors; and memory storing instructions that, when executed by the one or more processors, cause the one or more processors to:

detect a contact force or torque exerted on the robotic arm by an external object via the one or more sensors; and in response to detecting the contact force or torque, in accordance with a determination that the contact force or torque is between a lower force or torque limit and an upper contact force or torque limit, enable movement of the robotic arm in a trajectory that is based on a pre-established or pre-recorded path of the robotic arm.

Clause 16. The robotic system of clause 15, wherein the one or more sensors include one or more contact sensors.

Clause 17. The robotic system of clause 15 or 16, wherein the one or more sensors include a six-axis load cell.

Clause 18. The robotic system of any of clauses 15-17, wherein the pre-established or pre-recorded path of the robotic arm comprises a pre-recorded path of a link centroid of the robotic arm.

Clause 19. The robotic system of clause 18, wherein the memory further includes instructions that, when executed by the one or more processors, cause the one or more processors to: determine, from the pre-recorded path of the link centroid, a translational and rotational motion direction along the pre-recorded path over a configurable period.

Clause 20. The robotic system of any of clauses 15-19, wherein the pre-established or pre-recorded path of the robotic arm comprises a pre-established or pre-recorded path of a pitch and/or yaw angle of a remote center motion of the robotic arm.

Clause 21. The robotic system of clause 20, wherein the memory further includes instructions that, when executed by the one or more processors, cause the one or more processors to: determine, from the pre-established or pre-recorded path of the robotic arm, an average motion direction along the pre-recorded path over a configurable period.

Clause 22. A robotic system, comprising:

a robotic arm;

one or more sensors;

one or more processors; and memory storing instructions that, when executed by the one or more processors, cause the one or more processors to:

detect a contact force or torque on the robotic arm exerted by an external object via the one or more sensors; and in accordance with a determination that the contact force or torque is greater than or equal to a lower reaction force or torque limit, reduce a velocity of the robotic arm.

Clause 23. The robotic system of clause 22, wherein:

the robotic arm includes one or more joints; and reducing the velocity of the robotic arm comprises reducing a respective velocity for each of the one or more joints of the robotic arm.

Clause 24. The robotic system of clause 23, wherein reducing the respective velocity for each of the one or more joints comprises reducing velocities of all the joints by a same scale.

Clause 25. The robotic system of any of clauses 22-24, wherein reducing the velocity of the robotic arm comprises reducing an angular velocity at a remote center motion of the robotic arm.

Clause 26. The robotic system of any of clauses 22-25, wherein the one or more sensors include one or more contact sensors.

Clause 27. The robotic system of any of clauses 22-26, wherein the one or more sensors include a six-axis load cell.

What is claimed is:

1. A robotic system, comprising:

a robotic arm;

one or more sensors;

one or more processors; and memory storing instructions that, when executed by the one or more processors, cause the one or more processors to:

detect, via the one or more sensors, a contact force or torque that is exerted on the robotic arm by an external object;

in response to detecting the contact force or torque, in accordance with a determination that a magnitude of the contact force or torque is between a lower contact force or torque limit and an upper contact force or torque limit, enable a first set of controlled movements on the robotic arm in accordance with the detected contact force or torque;

receive a first user command comprising a first velocity of the robotic arm;

in accordance with the determination that the magnitude of the contact force is between the lower contact force limit and the upper contact force limit:

a) determine a direction of the contact force;

b) determine a direction of the torque;

c) determine a first angle formed by a translational velocity of the robotic arm and the direction of the contact force; and d) determine a second angle formed by a rotational velocity of the robotic arm and the direction of the torque;

in accordance with a determination that the first angle is within a first angular threshold and the second angle is within a second angular threshold, enable movement of one or more joints of the robotic arm at the first velocity; and in accordance with at least one of:

(i) a determination that the first angle exceeds the first angular threshold, or (ii) a determination that the second angle exceeds the second angular threshold, disable movement of the robotic arm.

2. The robotic system of claim 1, wherein enabling a first set of controlled movements on the robotic arm comprises activating null space motion of the robotic arm.

3. The robotic system of claim 1, wherein the memory further includes instructions that, when executed by the one or more processors, cause the one or more processors to:

in response to detecting the contact force or torque, in accordance with a determination that the contact force or torque exceeds the upper contact force or torque limit, disable movement of a part of the robotic system.

4. The robotic system of claim 1, wherein the memory further includes instructions that, when executed by the one or more processors, cause the one or more processors to:

in response to detecting the contact force or torque, in accordance with a determination that the contact force or torque is less than the lower contact force or torque, forgo enabling the first set of controlled movements on the robotic arm in accordance with the detected contact force or torque.

5. The robotic system of claim 1, wherein:

the one or more sensors include one or more contact sensors; and the contact force or torque is detected using the one or more contact sensors.

6. The robotic system of claim 5, wherein the one or more contact sensors are located on a link of the robotic arm.

7. The robotic system of claim 6, wherein the link of the robotic arm is a distal link or a proximal link.

8. The robotic system of claim 1, wherein:

the one or more sensors include a multi-axis load cell; and the contact force or torque is detected using the multi-axis load cell.

9. The robotic system of claim 8, wherein the multi-axis load cell comprises a six-axis load cell that is located on a distal portion of the robotic arm.

10. The robotic system of claim 1, wherein the first angular threshold and the second angular threshold are determined according to a measurement uncertainty of one or more contact sensors used to detect the contact force.

11. The robotic system of claim 1, wherein the memory further includes instructions that, when executed by the one or more processors, cause the one or more processors to:

receive a second user command comprising a requested velocity of the robotic arm;

in accordance with the determination that the magnitude of the torque is between the lower torque limit and the upper torque limit:

determine a direction of the torque;

determine a third angle formed by the direction of the torque and the requested velocity of the robotic arm;

in accordance with a determination that the third angle is within a third angular threshold, enable movement the robotic arm at the requested velocity; and in accordance with a determination that the third angle exceeds the third angular threshold, disable movement of the robotic arm.

12. The robotic system of claim 11, wherein the magnitude of the torque is determined with respect to a remote center of motion of the robotic arm.

13. The robotic system of claim 11, wherein the third angular threshold is determined according to a measurement uncertainty of a six-axis load cell used to detect the torque.

14. The robotic system of claim 1, wherein the magnitude of the contact force or torque is determined with respect to a remote center of motion of the robotic arm, and wherein the first set of controlled movements are based on the remote center of motion.

15. A robotic system, comprising:

a robotic arm;

one or more sensors;

one or more processors; and memory storing instructions that, when executed by the one or more processors, cause the one or more processors to:

detect a contact force or torque on the robotic arm exerted by an external object via the one or more sensors; and in accordance with a determination that the contact force or torque is greater than or equal to a lower reaction force or torque limit, reduce a velocity of the robotic arm, wherein the reduced velocity is of a null space motion of the robotic arm.

16. The robotic system of claim 15, wherein:

the robotic arm includes one or more joints; and reducing the velocity of the robotic arm comprises reducing a respective velocity for each of the one or more joints of the robotic arm.

17. The robotic system of claim 16, wherein reducing the respective velocity for each of the one or more joints comprises reducing velocities of all the joints by a same scale.

18. The robotic system of claim 15, wherein reducing the velocity of the robotic arm comprises reducing an angular velocity at a remote center of motion of the robotic arm.

19. The robotic system of claim 15, wherein the one or more sensors include one or more contact sensors.

20. The robotic system of claim 15, wherein the one or more sensors include a six-axis load cell.

21. A robotic system, comprising:

a robotic arm;

one or more sensors;

one or more processors; and memory storing instructions that, when executed by the one or more processors, cause the one or more processors to:

detect, via the one or more sensors, a contact force or torque that is exerted on the robotic arm by an external object; and in response to detecting the contact force or torque, in accordance with a determination that a magnitude of the contact force or torque is between a lower contact force or torque limit and an upper contact force or torque limit, enable a first set of controlled movements on the robotic arm in accordance with the detected contact force or torque;

receive a second user command comprising a requested velocity of the robotic arm;

in accordance with the determination that the magnitude of the torque is between the lower torque limit and the upper torque limit:

determine a direction of the torque;

determine a third angle formed by the direction of the torque and the requested velocity of the robotic arm;

in accordance with a determination that the third angle is within a third angular threshold, enable movement the robotic arm at the requested velocity; and in accordance with a determination that the third angle exceeds the third angular threshold, disable movement of the robotic arm.

22. The robotic system of claim 21, wherein the magnitude of the torque is determined with respect to a remote center of motion of the robotic arm.

23. The robotic system of claim 21, wherein the third angular threshold is determined according to a measurement uncertainty of a six-axis load cell used to detect the torque.

* * * * *